United States Patent
Belhocine et al.

(10) Patent No.: US 11,932,899 B2
(45) Date of Patent: *Mar. 19, 2024

(54) METHODS AND SYSTEMS FOR CHARACTERIZING NUCLEIC ACID MOLECULES

(71) Applicant: 10X Genomics, Inc., Pleasanton, CA (US)

(72) Inventors: Kamila Belhocine, Fremont, CA (US); Michael Schnall-Levin, San Francisco, CA (US); Andrew D. Price, Hayward, CA (US)

(73) Assignee: 10X GENOMICS, INC., Pleasanton, CA (US)

(*) Notice: Subject to any disclaimer, the term of this patent is extended or adjusted under 35 U.S.C. 154(b) by 820 days.

This patent is subject to a terminal disclaimer.

(21) Appl. No.: 16/434,068

(22) Filed: Jun. 6, 2019

(65) Prior Publication Data

US 2019/0376118 A1  Dec. 12, 2019

Related U.S. Application Data

(60) Provisional application No. 62/682,119, filed on Jun. 7, 2018.

(51) Int. Cl.
*C12Q 1/68* (2018.01)

(52) U.S. Cl.
CPC ......... *C12Q 1/68* (2013.01); *C12Q 2537/164* (2013.01); *C12Q 2563/149* (2013.01); *C12Q 2563/185* (2013.01)

(58) Field of Classification Search
CPC .............. C12Q 1/68; C12Q 2537/164; C12Q 2563/149; C12Q 2563/185; C12Q 1/6827; C12Q 2563/159; C12Q 2563/179

See application file for complete search history.

(56) References Cited

U.S. PATENT DOCUMENTS

| | | | |
|---|---|---|---|
| 4,124,638 A | 11/1978 | Hansen | |
| 5,137,829 A | 8/1992 | Nag et al. | |
| 5,185,099 A | 2/1993 | Delpuech et al. | |
| 5,270,183 A | 12/1993 | Corbett et al. | |
| 5,478,893 A | 12/1995 | Ghosh et al. | |
| 5,736,330 A | 4/1998 | Fulton | |
| 5,756,334 A | 5/1998 | Perler et al. | |
| 5,846,719 A | 12/1998 | Brenner et al. | |
| 5,900,481 A | 5/1999 | Lough et al. | |
| 5,942,609 A | 8/1999 | Hunkapiller et al. | |
| 5,965,443 A | 10/1999 | Reznikoff et al. | |
| 5,994,056 A | 11/1999 | Higuchi | |
| 6,033,880 A | 3/2000 | Haff et al. | |
| 6,057,149 A | 5/2000 | Burns et al. | |
| 6,123,798 A | 9/2000 | Gandhi et al. | |
| 6,171,850 B1 | 1/2001 | Nagle et al. | |
| 6,172,218 B1 | 1/2001 | Brenner | |
| 6,176,962 B1 | 1/2001 | Soane et al. | |
| 6,207,384 B1 | 3/2001 | Mekalanos et al. | |
| 6,294,385 B1 | 9/2001 | Goryshin et al. | |
| 6,306,590 B1 | 10/2001 | Mehta et al. | |
| 6,327,410 B1 | 12/2001 | Walt et al. | |
| 6,379,929 B1 | 4/2002 | Burns et al. | |
| 6,406,848 B1 | 6/2002 | Bridgham et al. | |
| 6,409,832 B2 | 6/2002 | Weigl et al. | |
| 6,492,118 B1 | 12/2002 | Abrams et al. | |
| 6,524,456 B1 | 2/2003 | Ramsey et al. | |
| 6,586,176 B1 | 7/2003 | Trnovsky et al. | |
| 6,632,655 B1 | 10/2003 | Mehta et al. | |
| 6,915,679 B2 | 7/2005 | Chien et al. | |
| 7,041,481 B2 | 5/2006 | Anderson et al. | |
| 7,115,400 B1 | 10/2006 | Adessi et al. | |
| 7,129,091 B2 | 10/2006 | Ismagilov et al. | |
| 7,138,267 B1 | 11/2006 | Jendrisak et al. | |
| 7,262,056 B2 | 8/2007 | Wooddell et al. | |
| 7,268,167 B2 | 9/2007 | Higuchi et al. | |
| 7,282,370 B2 | 10/2007 | Bridgham et al. | |
| 7,294,503 B2 | 11/2007 | Quake et al. | |
| 7,323,305 B2 | 1/2008 | Leamon et al. | |

(Continued)

FOREIGN PATENT DOCUMENTS

| | | |
|---|---|---|
| EP | 1019496 B1 | 9/2004 |
| EP | 1841879 A2 | 10/2007 |

(Continued)

OTHER PUBLICATIONS

Caen et al, Microfluidics as a Strategic Player to Decipher Single-Cell Omics?, Trends in Biotechnology, 2017, 35, pp. 713-727 (Year: 2017).*

Nisisako, T. et al. "Droplet Formation in a Microchannel on PMMA Plate"Abstract. 2001 Kluwer Academic Publishers. p. 137-138.

Nisisako, T. et al., Microfluidics large-scale integration on a chip for mass production of monodisperse droplets and particles, The Royal Society of Chemistry: Lab Chip, (Nov. 23, 2007) 8:287-293.

Novak, R. et al., "Single cell multiplex gene detection and sequencing using microfluidicallygenerated agarose emulsions" Angew. Chem. Int. Ed. Engl. (2011) 50(2):390-395.

Perrott, Jimmy. Optimization and Improvement of Emulsion PCR for the Ion Torrent Next-Generation Sequencing Platform. (2011) Thesis.

(Continued)

*Primary Examiner* — Narayan K Bhat

(74) *Attorney, Agent, or Firm* — Wilson Sonsini Goodrich & Rosati

(57) ABSTRACT

Provided herein are methods and systems for characterizing a nucleic acid molecule from a single cell. A method for characterizing a nucleic acid molecule from a single cell may comprise providing a partition (e.g., droplets or wells) comprising a single cell and a single bead. The single bead may comprise a nucleic acid barcode molecule. A nucleic acid molecule from the single cell and the nucleic acid barcode molecule may be used to generate a barcoded nucleic acid molecule for sequencing, which may be used to determine an epigenetic state or characteristic of the nucleic acid molecule as being associated with the single cell.

21 Claims, 18 Drawing Sheets

(56) References Cited

U.S. PATENT DOCUMENTS

| | | |
|---|---|---|
| 7,544,473 B2 | 6/2009 | Brenner |
| 7,608,434 B2 | 10/2009 | Reznikoff et al. |
| 7,622,076 B2 | 11/2009 | Davies et al. |
| 7,622,280 B2 | 11/2009 | Holliger et al. |
| 7,645,596 B2 | 1/2010 | Williams et al. |
| 7,708,949 B2 | 5/2010 | Stone et al. |
| 7,772,287 B2 | 8/2010 | Higuchi et al. |
| 7,776,927 B2 | 8/2010 | Chu et al. |
| 7,842,457 B2 | 11/2010 | Berka et al. |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,968,287 B2 | 6/2011 | Griffiths et al. |
| 8,053,192 B2 | 11/2011 | Bignell et al. |
| 8,133,719 B2 | 3/2012 | Drmanac et al. |
| 8,168,385 B2 | 5/2012 | Brenner |
| 8,268,564 B2 | 9/2012 | Roth et al. |
| 8,273,573 B2 | 9/2012 | Ismagilov et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,329,407 B2 | 12/2012 | Ismagilov et al. |
| 8,592,150 B2 | 11/2013 | Drmanac et al. |
| 8,658,430 B2 | 2/2014 | Miller et al. |
| 8,822,148 B2 | 9/2014 | Ismagliov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,927,218 B2 | 1/2015 | Forsyth |
| 8,975,302 B2 | 3/2015 | Light et al. |
| 9,005,935 B2 | 4/2015 | Belyaev |
| 9,012,390 B2 | 4/2015 | Holtze et al. |
| 9,029,083 B2 | 5/2015 | Griffiths et al. |
| 9,029,085 B2 | 5/2015 | Agresti et al. |
| 9,080,211 B2 | 7/2015 | Grunenwald et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,238,671 B2 | 1/2016 | Goryshin et al. |
| 9,266,104 B2 | 2/2016 | Link |
| 9,290,808 B2 | 3/2016 | Fodor et al. |
| 9,328,382 B2 | 5/2016 | Drmanac et al. |
| 9,347,059 B2 | 5/2016 | Saxonov |
| 9,371,598 B2 | 6/2016 | Chee |
| 9,388,465 B2 | 7/2016 | Hindson et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,574,226 B2 | 2/2017 | Gormley et al. |
| 9,593,365 B2 | 3/2017 | Frisen et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,701,998 B2 | 7/2017 | Hindson et al. |
| 9,764,322 B2 | 9/2017 | Hiddessen et al. |
| 9,822,396 B2 | 11/2017 | Litterst et al. |
| 9,824,068 B2 | 11/2017 | Wong |
| 9,868,979 B2 | 1/2018 | Chee et al. |
| 9,879,313 B2 | 1/2018 | Chee et al. |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,030,261 B2 | 7/2018 | Frisen et al. |
| 10,059,989 B2 | 8/2018 | Giresi et al. |
| 10,221,436 B2 | 3/2019 | Hardenbol et al. |
| 10,221,442 B2 | 3/2019 | Hindson et al. |
| 10,227,646 B2 | 3/2019 | Vaisvila et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 | 9/2019 | Hindson et al. |
| 10,428,326 B2 | 10/2019 | Belhocine et al. |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,590,244 B2 | 3/2020 | Delaney et al. |
| 10,745,742 B2 | 8/2020 | Bent et al. |
| 10,752,949 B2 | 8/2020 | Hindson et al. |
| 10,774,374 B2 | 9/2020 | Frisen et al. |
| 10,815,525 B2 | 10/2020 | Lucero et al. |
| 10,829,815 B2 | 11/2020 | Bharadwaj et al. |
| 10,837,047 B2 | 11/2020 | Delaney et al. |
| 10,874,997 B2 | 12/2020 | Weitz et al. |
| 10,995,333 B2 | 5/2021 | Pfeiffer |
| 11,459,607 B1 | 10/2022 | Terry et al. |
| 11,467,153 B2 | 10/2022 | Belhocine et al. |
| 11,655,499 B1 | 5/2023 | Pfeiffer |
| 2002/0005354 A1 | 1/2002 | Spence et al. |
| 2002/0051971 A1 | 5/2002 | Stuelpnagel et al. |
| 2002/0058332 A1 | 5/2002 | Quake et al. |
| 2002/0092767 A1 | 7/2002 | Bjornson et al. |
| 2002/0119455 A1 | 8/2002 | Chan |
| 2002/0127736 A1 | 9/2002 | Chou et al. |
| 2002/0197639 A1* | 12/2002 | Shia .......... C12Q 1/6827 435/6.12 |
| 2003/0036206 A1 | 2/2003 | Chien et al. |
| 2003/0075446 A1 | 4/2003 | Culbertson et al. |
| 2003/0124509 A1 | 7/2003 | Kenis et al. |
| 2003/0215862 A1 | 11/2003 | Parce et al. |
| 2004/0068019 A1 | 4/2004 | Higuchi et al. |
| 2005/0130188 A1 | 6/2005 | Walt et al. |
| 2005/0250147 A1 | 11/2005 | Macevicz |
| 2005/0266582 A1 | 12/2005 | Modlin et al. |
| 2005/0287572 A1 | 12/2005 | Mathies et al. |
| 2006/0177832 A1 | 8/2006 | Brenner |
| 2006/0275782 A1 | 12/2006 | Gunderson et al. |
| 2007/0020640 A1 | 1/2007 | McCloskey et al. |
| 2007/0042419 A1 | 2/2007 | Barany et al. |
| 2007/0172873 A1 | 7/2007 | Brenner et al. |
| 2007/0190543 A1 | 8/2007 | Livak |
| 2007/0196397 A1 | 8/2007 | Torii et al. |
| 2007/0264320 A1 | 11/2007 | Lee et al. |
| 2008/0056948 A1 | 3/2008 | Dale et al. |
| 2008/0166720 A1 | 7/2008 | Hsieh et al. |
| 2008/0242560 A1 | 10/2008 | Gunderson et al. |
| 2009/0011943 A1 | 1/2009 | Drmanac et al. |
| 2009/0047713 A1 | 2/2009 | Handique |
| 2009/0099041 A1 | 4/2009 | Church et al. |
| 2009/0131543 A1 | 5/2009 | Weitz et al. |
| 2009/0148961 A1 | 6/2009 | Luchini et al. |
| 2009/0155563 A1 | 6/2009 | Petsev et al. |
| 2009/0202984 A1 | 8/2009 | Cantor |
| 2009/0235990 A1 | 9/2009 | Beer |
| 2009/0269248 A1 | 10/2009 | Falb et al. |
| 2009/0286687 A1 | 11/2009 | Dressman et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0105866 A1 | 4/2010 | Fraden et al. |
| 2010/0184928 A1 | 7/2010 | Kumacheva |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0217736 A1 | 9/2011 | Hindson |
| 2011/0305761 A1 | 12/2011 | Shum et al. |
| 2012/0071331 A1 | 3/2012 | Casbon et al. |
| 2012/0156677 A1 | 6/2012 | Bitinaite et al. |
| 2012/0172259 A1 | 7/2012 | Rigatti et al. |
| 2012/0190032 A1 | 7/2012 | Ness et al. |

(56) References Cited

U.S. PATENT DOCUMENTS

| | | |
|---|---|---|
| 2012/0196288 A1 | 8/2012 | Beer |
| 2012/0219947 A1 | 8/2012 | Yurkovetsky et al. |
| 2013/0028812 A1 | 1/2013 | Prieto et al. |
| 2013/0109575 A1 | 5/2013 | Kleinschmidt et al. |
| 2014/0065234 A1 | 3/2014 | Shum et al. |
| 2014/0093916 A1 | 4/2014 | Belyaev |
| 2014/0155295 A1 | 6/2014 | Hindson et al. |
| 2014/0221239 A1 | 8/2014 | Carman et al. |
| 2014/0272996 A1 | 9/2014 | Bemis |
| 2014/0274740 A1 | 9/2014 | Srinivasan et al. |
| 2014/0302503 A1 | 10/2014 | Lowe et al. |
| 2014/0338753 A1 | 11/2014 | Sperling et al. |
| 2014/0378345 A1 | 12/2014 | Hindson et al. |
| 2015/0066385 A1 | 3/2015 | Schnall-Levin et al. |
| 2015/0111788 A1 | 4/2015 | Fernandez et al. |
| 2015/0220532 A1 | 8/2015 | Wong |
| 2015/0267191 A1 | 9/2015 | Steelman et al. |
| 2015/0291942 A1 | 10/2015 | Gloeckner et al. |
| 2015/0292988 A1 | 10/2015 | Bharadwaj et al. |
| 2015/0361418 A1 | 12/2015 | Reed |
| 2015/0368638 A1 | 12/2015 | Steemers et al. |
| 2015/0368694 A1 | 12/2015 | Pan et al. |
| 2015/0376605 A1 | 12/2015 | Xiohua et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0115474 A1 | 4/2016 | Jelinek et al. |
| 2016/0122753 A1 | 5/2016 | Mikkelsen et al. |
| 2016/0122817 A1 | 5/2016 | Jarosz et al. |
| 2016/0203196 A1 | 7/2016 | Schnall-Levin et al. |
| 2016/0208323 A1 | 7/2016 | Bernstein et al. |
| 2016/0232291 A1 | 8/2016 | Sofia et al. |
| 2016/0244809 A1 | 8/2016 | Belgrader et al. |
| 2016/0281160 A1 | 9/2016 | Jarosz et al. |
| 2016/0289769 A1 | 10/2016 | Schwartz et al. |
| 2016/0314242 A1 | 10/2016 | Schnall-Levin et al. |
| 2016/0348093 A1 | 12/2016 | Price et al. |
| 2016/0362724 A1 | 12/2016 | Bailey et al. |
| 2016/0376605 A1 | 12/2016 | Konzak et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0235876 A1 | 8/2017 | Jaffe et al. |
| 2017/0260584 A1 | 9/2017 | Zheng et al. |
| 2018/0030515 A1 | 2/2018 | Regev et al. |
| 2018/0071695 A1 | 3/2018 | Weitz et al. |
| 2018/0080075 A1 | 3/2018 | Brenner et al. |
| 2018/0105808 A1 | 4/2018 | Mikkelsen et al. |
| 2018/0171397 A1* | 6/2018 | Vaisvila ............... C12N 9/0071 |
| 2018/0195112 A1 | 7/2018 | Lebofsky et al. |
| 2018/0216162 A1 | 8/2018 | Belhocine et al. |
| 2018/0312822 A1 | 11/2018 | Lee et al. |
| 2018/0312873 A1 | 11/2018 | Zheng |
| 2018/0334670 A1 | 11/2018 | Bharadwaj et al. |
| 2018/0340169 A1 | 11/2018 | Belhocine et al. |
| 2018/0340171 A1 | 11/2018 | Belhocine et al. |
| 2018/0355348 A1 | 12/2018 | Adey et al. |
| 2018/0371545 A1 | 12/2018 | Wong et al. |
| 2019/0002967 A1 | 1/2019 | Chen et al. |
| 2019/0032128 A1 | 1/2019 | Chen et al. |
| 2019/0040382 A1 | 2/2019 | Steemers et al. |
| 2019/0060890 A1 | 2/2019 | Bharadwaj et al. |
| 2019/0060904 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0085391 A1 | 3/2019 | Hindson et al. |
| 2019/0100632 A1 | 4/2019 | Delaney et al. |
| 2019/0127731 A1 | 5/2019 | McDermott |
| 2019/0134633 A1 | 5/2019 | Bharadwaj et al. |
| 2019/0136316 A1 | 5/2019 | Hindson et al. |
| 2019/0153532 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0249226 A1 | 8/2019 | Bent et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |
| 2019/0367997 A1 | 12/2019 | Bent et al. |
| 2020/0002763 A1 | 1/2020 | Belgrader et al. |
| 2020/0005902 A1 | 1/2020 | Mellen et al. |
| 2020/0032335 A1 | 1/2020 | Alvarado Martinez |
| 2020/0033237 A1 | 1/2020 | Hindson et al. |
| 2020/0033366 A1 | 1/2020 | Alvarado Martinez |
| 2021/0190770 A1 | 6/2021 | Delaney et al. |
| 2021/0270703 A1 | 9/2021 | Abousoud |

FOREIGN PATENT DOCUMENTS

| | | |
|---|---|---|
| EP | 1841879 A4 | 5/2009 |
| EP | 1967592 B1 | 4/2010 |
| EP | 2540389 A1 | 1/2013 |
| EP | 2635679 B1 | 4/2017 |
| GB | 2097692 A | 11/1982 |
| GB | 2097692 B | 5/1985 |
| WO | WO-84/02000 | 5/1984 |
| WO | WO-95/30782 | 11/1995 |
| WO | WO-99/52708 | 10/1999 |
| WO | WO-2000008212 A1 | 2/2000 |
| WO | WO-2001002850 A1 | 1/2001 |
| WO | WO-0114589 A2 | 3/2001 |
| WO | WO-0189787 A2 | 11/2001 |
| WO | WO-0190418 A1 | 11/2001 |
| WO | WO-2001089787 A9 | 11/2001 |
| WO | WO-2004002627 A2 | 1/2004 |
| WO | WO-2004065617 A2 | 8/2004 |
| WO | WO-2004069849 A2 | 8/2004 |
| WO | WO-2004091763 A2 | 10/2004 |
| WO | WO-2004069849 A3 | 3/2005 |
| WO | WO-2005021151 A1 | 3/2005 |
| WO | WO-2005049787 A2 | 6/2005 |
| WO | WO-2005082098 A2 | 9/2005 |
| WO | WO-2005082098 A3 | 12/2005 |
| WO | WO-2006040551 A2 | 4/2006 |
| WO | WO-2004065617 A3 | 6/2006 |
| WO | WO-2006078841 A1 | 7/2006 |
| WO | WO-2006096571 A2 | 9/2006 |
| WO | WO-2007081385 A2 | 7/2007 |
| WO | WO-2007081387 A1 | 7/2007 |
| WO | WO-2007089541 A2 | 8/2007 |
| WO | WO-2007133710 A2 | 11/2007 |
| WO | WO-2007140015 A2 | 12/2007 |
| WO | WO-2007147079 A2 | 12/2007 |
| WO | WO-2008021123 A1 | 2/2008 |
| WO | WO-2007147079 A3 | 3/2008 |
| WO | WO-2008109176 A2 | 9/2008 |
| WO | WO-2008121342 A2 | 10/2008 |
| WO | WO-2008134153 A1 | 11/2008 |
| WO | WO-2008150432 A1 | 12/2008 |
| WO | WO-2009011808 A1 | 1/2009 |
| WO | WO-2009015296 A1 | 1/2009 |
| WO | WO-2009085215 A1 | 7/2009 |
| WO | WO-2009147386 A1 | 12/2009 |
| WO | WO-2009152928 A2 | 12/2009 |
| WO | WO-2010033200 A2 | 3/2010 |
| WO | WO-2010048605 A1 | 4/2010 |
| WO | WO-2010104604 A1 | 9/2010 |
| WO | WO-2010117620 A2 | 10/2010 |
| WO | WO-2010148039 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2010148039 A3 | 7/2011 |
| WO | WO-2012048341 A1 | 4/2012 |

(56) References Cited

FOREIGN PATENT DOCUMENTS

| | | |
|---|---|---|
| WO | WO-2012061832 A1 | 5/2012 |
| WO | WO-2012083225 A2 | 6/2012 |
| WO | WO-2012083225 A3 | 8/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2012116331 A3 | 3/2013 |
| WO | WO-2013036929 A1 | 3/2013 |
| WO | WO-2013055955 A1 | 4/2013 |
| WO | WO-2013096643 A1 | 6/2013 |
| WO | WO-2013126741 A1 | 8/2013 |
| WO | WO-2013134261 A1 | 9/2013 |
| WO | WO-2012106546 A3 | 11/2013 |
| WO | WO-2014028378 A2 | 2/2014 |
| WO | WO 2014/043763 * | 3/2014 |
| WO | WO-2012142531 A3 | 5/2014 |
| WO | WO-2012166425 A3 | 5/2014 |
| WO | WO-2014108810 A2 | 7/2014 |
| WO | WO-2014165559 A2 | 10/2014 |
| WO | WO-2014108810 A3 | 12/2014 |
| WO | WO-2015015199 A2 | 2/2015 |
| WO | WO-2015044428 A1 | 4/2015 |
| WO | WO-2015164212 A1 | 10/2015 |
| WO | WO-2012142611 A3 | 3/2016 |
| WO | WO-2016040476 A1 | 3/2016 |
| WO | WO-2016061517 A2 | 4/2016 |
| WO | WO-2016061517 A3 | 6/2016 |
| WO | WO-2016126871 A2 | 8/2016 |
| WO | WO-2016168584 A1 | 10/2016 |
| WO | WO-2016191618 A1 | 12/2016 |
| WO | WO-2016207647 A1 | 12/2016 |
| WO | WO-2016207653 A1 | 12/2016 |
| WO | WO-2017015075 A1 | 1/2017 |
| WO | WO-2017025594 A1 | 2/2017 |
| WO | WO-2017034970 A1 | 3/2017 |
| WO | WO-2017066231 A1 | 4/2017 |
| WO | WO-2017075265 A1 | 5/2017 |
| WO | WO-2017180949 A1 | 10/2017 |
| WO | WO-2017184707 A1 | 10/2017 |
| WO | WO-2017197343 A2 | 11/2017 |
| WO | WO-2018031631 A1 | 2/2018 |
| WO | WO-2018039338 A1 | 3/2018 |
| WO | WO-2018039969 A1 | 3/2018 |
| WO | WO-2018091676 A1 | 5/2018 |
| WO | WO-2018103025 A1 | 6/2018 |
| WO | WO-2018119301 A1 | 6/2018 |
| WO | WO-2018119447 A2 | 6/2018 |
| WO | WO-2018129368 A2 | 7/2018 |
| WO | WO 2018/140966 * | 8/2018 |
| WO | WO 2018/172726 * | 9/2018 |
| WO | WO-2018172726 A1 | 9/2018 |
| WO | WO-2018191701 A1 | 10/2018 |
| WO | WO-2018213643 A1 | 11/2018 |
| WO | WO-2018217912 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019060907 A1 | 3/2019 |
| WO | WO-2019083852 A1 | 5/2019 |
| WO | WO-2019084043 A1 | 5/2019 |
| WO | WO-2019084165 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020142779 A1 | 7/2020 |
| WO | WO-2020168013 A1 | 8/2020 |
| WO | WO-2020198532 A1 | 10/2020 |
| WO | WO-2021046475 A1 | 3/2021 |
| WO | WO-2021133845 A1 | 7/2021 |
| WO | WO-2021207610 A1 | 10/2021 |
| WO | WO-2021212042 A1 | 10/2021 |
| WO | WO-2021/222302 A1 | 11/2021 |
| WO | WO-2021222301 A1 | 11/2021 |
| WO | WO-2022103712 A1 | 5/2022 |
| WO | WO-2022182682 A1 | 9/2022 |
| WO | WO-2022182785 A1 | 9/2022 |
| WO | WO-2022271908 A1 | 12/2022 |
| WO | WO-2023076528 A2 | 5/2023 |

OTHER PUBLICATIONS

Peters, B.A. et al. Accurate whole-genome sequencing and haplotyping from 10 to 20 human cells. Nature, 487(7406):190-195 (Jul. 11, 2012).
Pushkarev et al. "Single-molecule sequencing of an individual human genome," Nature Biotech (2009) 17:847-850.
Ramsey, J.M. "The burgeoning power of the shrinking laboratory" Nature Biotech (1999) 17:1061-1062.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-7. URL:http://454.com/downloads/my454/documentation/technical-bulletins/TCB-09004 Using MultiplexIdentifierAdaptorsForTheGSFLXTitaniumSeriesChemistry-BasicMIDSet.pdf.
Rotem, A. et al. "Single Cell Chip-Seq Using Drop-Based Microfluidics" Abstract #50. Frontiers of Single Cell Analysis, Stanford University Sep. 5-7, 2013.
Rotem, A. et al., "High-throughput single-cell labeling (Hi-SCL) for RNA-Seq using drop-based microfluidics" PLOS One (May 22, 2015) 0116328 (14 pages).
Schubert, et al. Microemulsifying fluorinated oils with mixtures of fluorinated and hydrogenated surfactants. Colloids and Surfaces A; Physicochemical and Engineering Aspects, 84(1994) 97-106.
Seiffert, et al. Microfluidic fabrication of smart microgels from macromolecular precursors. 2010. Polymer.
Seiffert, S. et al., "Smart microgel capsules from macromolecular precursors" J. Am. Chem. Soc. (2010) 132:6606-6609.
Shah, "Fabrication of mono disperse thermosensitive microgels and gel capsules in micro fluidic devices", Soft Matter, 4:2303-2309 (2008).
Shendure et al. "Accurate Multiplex Polony Sequencing of an Evolved bacterial Genome" Science (2005) 309:1728-1732.
Song, et al. Reactions in droplets in microfluidic channels. Angew Chem Int Ed Engl. Nov. 13, 2006;45(44):7336-56.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thorsen, et al. Dynamic pattern formation in a vesicle-generating microfluidic device. Physical Review Letters. American Physical Society. 2001; 86(18):4163-4166.
Tonelli, et al. Perfluoropolyether functional oligomers: unusual reactivity in organic chemistry. Journal of fluorine chemistry. 2002; 118(1)"107-121.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Weigl, et al. Microfluidic Diffusion-Based Separation and Detection. Science. 1999; pp. 346-347.
Williams, et al. Amplification of complex gene libraries by emulsion PCR. Nature Methods. 2006;3(7):545-50.

(56) References Cited

OTHER PUBLICATIONS

Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhu, et al. Reverse transcriptase template switching: a Smart approach for full-length cDNA library construction. Biotechniques. Apr. 2001;30(4):892-7.
"Lennon et al. A scalable, fully automated process for construction of sequence-ready barcoded libraries for 454. Genome Biology 11:R15 (2010).".
Abate, A.R. et al. "Beating Poisson encapsulation statistics using close-packed ordering" Lab on a Chip (Sep. 21, 2009) 9(18):2628-2631.
Agasti, S.S. et al. "Photocleavable DNA barcode-antibody conjugates allow sensitive and multiplexed protein analysis in single cell" J Am Chem Soc (2012) 134(45):18499-18502.
Amini, S. et al. "Haplotype-resolved whole-genome sequencing by contiguity-preserving transposition and combinatorial indexing" Nature Genetics (2014) 46:1343-1349 doi:10.1038/ng.3119.
Anna et al.: Formation of dispersions using "flow focusing" in microchannels: Applied Physics Letters, vol. 82, No. 3, pp. 364-366 (2003).
Baret, "Surfactants in droplet-based microfluidics" Lab Chip (12(3):422-433 (2012).
Beer et al. On-Chip, Real-Time, Single-Copy Polymerase Chain Reaction in Picoliter Droplets. Anal Chem 79:8471-8475 (2007).
Brenner, et al. "In vitro cloning of complex mixtures of DNA on microbeads: physical separation of differentially expressed cDNAs." Proc Natl Acad Sci U S A. Feb. 15, 2000;97(4):1665-70.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-5. Epub Aug. 9, 2001.
Chien et al. "Multiport flow-control system for lab-on-a-chip microfluidic devices", Fresenius J. Anal Chem, 371:106-111 (Jul. 27, 2001).
Chu, et al. Controllable monodisperse multiple emulsions. Angew Chem Int Ed Engl. 2007;46(47):8970-4.
Clausell-Tormos et al., "Droplet-based microfluidic platforms for the encapsulation and screening of mammalian cells and multicellular organisms", Chem. Biol. 15:427-437 (2008).
Co-pending PCT/US2019/024418, filed Mar. 27, 2019.
Co-pending PCT/US2019/046940, filed Aug. 16, 2019.
Co-pending U.S. Appl. No. 16/410,953, filed May 13, 2019.
Co-pending U.S. Appl. No. 16/415,617, filed May 17, 2019.
Co-pending U.S. Appl. No. 16/434,068, filed Jun. 6, 2019.
Co-pending U.S. Appl. No. 16/434,076, filed Jun. 6, 2019.
Co-pending U.S. Appl. No. 16/434,084, filed Jun. 6, 2019.
Co-pending U.S. Appl. No. 16/434,089, filed Apr. 1, 2019.
Co-pending U.S. Appl. No. 16/434,095, filed Jun. 6, 2019.
Co-pending U.S. Appl. No. 16/434,099, filed Jun. 6, 2019.
Co-pending U.S. Appl. No. 16/434,102, filed Jun. 6, 2019.
Co-pending U.S. Appl. No. 16/434,605, filed Jun. 7, 2019.
Co-pending U.S. Appl. No. 16/435,393, filed Jun. 7, 2019.
Co-pending U.S. Appl. No. 16/439,568, filed Jun. 12, 2019.
Co-pending U.S. Appl. No. 16/439,675, filed Jun. 12, 2019.
Co-pending U.S. Appl. No. 16/454,485, filed Jun. 27, 2019.
Co-pending U.S. Appl. No. 16/530,930, filed Aug. 2, 2019.
Co-pending U.S. Appl. No. 16/575,280, filed Sep. 18, 2019.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Duffy et al., Rapid Protyping of Microfluidic Systems and Polydimethylsiloxane, Anal Chem 70:4974-4984 (1998).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Hug, et al. Measurement of the number of molecules of a single mRNA species in a complex mRNA preparation. J Theor Biol. Apr. 21, 2003;221(4):615-24.
Jarosz, M. et al. "Using 1ng of DNA to detect haplotype phasing and gene fusions from whole exome sequencing of cancer cell lines" Cancer Res (2015) 75(supp15):4742.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Kenis, et al. Microfabrication Inside Capillaries Using Multiphase Laminar Flow Patterning. Science. 1999; 285:83-85.
Kivioja, et al. Counting absolute numbers of molecules using unique molecular identifiers. Nat Methods. Nov. 20, 2011;9(1):72-4.
Klein, et al. Droplet barcoding for single-cell transcriptomics applied to embryonic stem cells. Cell. May 21, 2015; 161:1187-1201.
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chem. 8: 1110-1115 (2008).
Lagally, et al. Single-Molecular DNA Amplification and Analysis in an Integrated Microfluidic Device. Anal Chem. Feb. 1, 2001;73(3):565-70.
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Mair, et al. Injection molded microfluidic chips featuring integrated interconnects. Lab Chip. Oct. 2006;6(10):1346-54. Epub Jul. 31, 2006.
McCoy, R. et al. "Illumina TruSeq Synthetic Long-Reads Empower De Novo Assembly and Resolve Complex, Highly-Repetitive Transposable Elements" PLOS (2014) 9(9):e1016689.
Microfluidic ChipShop. Microfluidic product catalogue. Oct. 2009.
Navin. The first five years of single-cell cancer genomics and beyond. Genome Res. Oct. 2015;25(10):1499-507. doi: 10.1101/gr.191098.115.
Nisisako, et al. Droplet formation in a microchannel network. Lab Chip. Feb. 2002;2(1):24-6. Epub Jan. 18, 2002.
Peters et al., "Accurate whole-genome sequencing and haplotyping from 10 to 20 human cells," Nature, Jul. 12, 2012, vol. 487, pp. 190-195.
10X Genomics, Inc. CG000153 Rev A. Chromium Single Cell DNA Reagent Kits User Guide. 2018.
10X Genomics, Inc. CG000184 Rev A. Chromium Single Cell 3' Reagent Kits v3 User Guide with Feature Barcoding Technology for CRISPR Screening. 2018.
10X Genomics, Inc. CG000185 Rev B. Chromium Single Cell 3' Reagent Kits User Guide with Feature Barcoding Technology for Cell Surface Protein. 2018.
10X Genomics, Inc. CG000208 Rev E. Chromium Next GEM Single Cell V(D)J reagent Kits v1.1 User Guide with Feature Barcode Technology for Cell Surface Protein. 2020.
10X Genomics, Inc. CG000209 Rev D. Chromium Next GEM Single Cell ATAC Reagent Kits v1.1 User Guide. 2020.
10X Genomics, Inc. CG000239 Rev B. Visium Spatial Gene Expression Reagent Kits User Guide. 2020.
10X Genomics, Inc. CG00026. Chromium Single Cell 3' Reagent Kit User Guide. 2016.

(56) References Cited

OTHER PUBLICATIONS

10X Genomics, Inc. LIT00003 Rev B Chromium Genome Solution Application Note. 2017.
Co-pending U.S. Appl. No. 16/708,214, filed Dec. 9, 2019.
Co-pending U.S. Appl. No. 16/737,762, filed Jan. 8, 2020.
Co-pending U.S. Appl. No. 16/737,770, filed Jan. 8, 2020.
Co-pending U.S. Appl. No. 16/789,273, filed Feb. 12, 2020.
Co-pending U.S. Appl. No. 16/789,287, filed Feb. 12, 2020.
Co-pending U.S. Appl. No. 16/800,450, filed Feb. 25, 2020.
Co-pending U.S. Appl. No. 16/814,908, filed Mar. 10, 2020.
Cusanovich, et al. Multiplex single-cell profiling of chromatin accessibility by combinatorial cellular indexing. Sciencexpress. May 7, 2014. p. 1-9. doi: 10.1126/science.aab1601.
PCT/US2020/017785 Application filed on Feb. 11, 2020 by Ziraldo, Solongo B. et al.
PCT/US2020/017789 Application filed on Feb. 11, 2020 by Belhocine, Zahara Kamila et al.
Yu, et al. Base-resolution analysis of 5-hydroxymethylcytosine in the mammalian genome. Cell. Jun. 8, 2012;149(6):1368-80. doi: 10.1016/j.cell.2012.04.027. Epub May 17, 2012.
Co-pending U.S. Appl. No. 17/014,909, inventor Giresi; Paul, filed Sep. 8, 2020.
Co-pending U.S. Appl. No. 17/148,942, inventors McDermott; Geoffrey et al., filed Jan. 14, 2021.
Co-pending U.S. Appl. No. 17/166,982, inventors McDermott; Geoffrey et al., filed Feb. 3, 2021.
Co-pending U.S. Appl. No. 17/175,542, inventors Maheshwari; Arundhati Shamoni et al., filed Feb. 12, 2021.
Co-pending U.S. Appl. No. 17/220,303, inventor Walter; Dagmar, filed Apr. 1, 2021.
Co-pending U.S. Appl. No. 17/381,612, inventor Martinez; Luigi Jhon Alvarado, filed Jul. 21, 2021.
Co-pending U.S. Appl. No. 17/499,039, inventors Pfeiffer; Katherine et al., filed Oct. 12, 2021.
Co-pending U.S. Appl. No. 17/512,241, inventors Hill; Andrew John et al., filed Oct. 27, 2021.
Co-pending U.S. Appl. No. 17/522,741, inventors Zheng; Xinying et al., filed Nov. 9, 2021.
Co-pending U.S. Appl. No. 17/545,862, inventor Katherine; Pfeiffer, filed Dec. 8, 2021.
Co-pending U.S. Appl. No. 17/573,350, inventor Corey; M. Nemec, filed Jan. 11, 2022.
Co-pending PCT application No. PCT/US2022/017558, inventors Dagmar et al., filed on Feb. 23, 2022.
Co-pending PCT application No. PCT/US2022/017377, inventors Pfeiffer et al., filed on Feb. 22, 2022.
Ackermann, et al. Integration of ATAC-seq and RNA-seq identifies human alpha cell and beta cell signature genes. Mol Metab. Jan. 11, 2016;5(3):233-244. doi: 10.1016/j.molmet.2016.01.002. eCollection Mar. 2016.
Adamson et al., "Production of arrays of chemically distinct nanolitre plugs via repeated splitting in microfluidic devices", Lab Chip 6(9): 1178-1186 (Sep. 2006).
Adey, et al. Rapid, low-input, low-bias construction of shotgun fragment libraries by high-density in vitro transposition. Genome Biology 11:R119 (2010).
Adey, et al., "Ultra-low-input, tagmentation-based whole-genome bisulfite sequencing", Genome Research, 2012, 22 ;6): 1139-1143.
Ason et al. DNA sequence bias during Tn5 transposition. Journal of molecular biology 335.5 (2004): 1213-1225.
Berkum, et al. Hi-C: a method to study the three-dimensional architecture of genomes. J Vis Exp. May 6, 2010;(39). pii: 1869. doi: 10.3791/1869.
Boyle, et al. "High-resolution genome-wide in vivo footprinting of diverse transcription factors in human cells", Genome Res. Mar. 2011;21(3):456-64.
Braeckmans et al., Scanning the Code. Modern Drug Discovery. 2003:28-32.

Buchman GW, et al. Selective RNA amplification: a novel method using dUMP-containing primers and uracil DNA glycosylase. PCR Methods Appl. Aug. 1993; 3(1):28-31.
Buenrostro, et al. ATAC-seq: A Method for Assaying Chromatin Accessibility Genome-Wide. Curr Protoc Mol Biol. Jan. 5, 2015;109: 21.29.1-21.29.9. doi:10.1002/0471142727.mb2129s109.
Buenrostro, et al. Single-cell chromatin accessibility reveals principles of regulatory variation. Nature. Jul. 23, 2015;523(7561):486-90. doi: 10.1038/nature14590. Epub Jun. 17, 2015.
Buenrostro, et al. "Transposition of native chromatin for fast and sensitive epigenomic profiling of open chromatin, DNA-binding proteins and nucleosome position." Nat Methods. Dec. 2013;10(12):1213-8. doi: 10.1038/nmeth.2688. Epub Oct. 6, 2013.
Cao, et al. Joint profiling of chromatin accessibility and gene expression in thousands of single cells. Science. Sep. 28, 2018;361(6409):1380-1385. doi: 10.1126/science.aau0730. Epub Aug. 30, 2018.
Caruccio, et al. Nextera Technology for NGS DNA Library Preparation: Simultaneous Fragmentation and Tagging by In Vitro Transposition, Nextera Technology, 2009, 16-3, 1-3. (Year: 2009).
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Chen et al. High-throughput sequencing of the transcriptome and chromatin accessibility in the same cell. Nat Biotechnol. Oct. 14, 2019. doi: 10.1038/s41587-019-0290-0. [Epub ahead of print].
Clark, et al. Single-cell epigenomics: powerful new methods for understanding gene regulation and cell identity. Genome Biol. Apr. 18, 2016;17:72. doi: 10.1186/s13059-016-0944-x.
Craig. Unity in Transposition Reactions. Science. Oct. 13, 1995;270(5234):253-4.
Cusanovich, et al. A Single-Cell Atlas of In Vivo Mammalian Chromatin Accessibility. Cell. Aug. 23, 2018;174(5):1309-1324. e18. doi: 10.1016/j.cell.2018.06.052. Epub Aug. 2, 2018.
Cusanovich, et al. Supplementary materials for Multiplex single-cell profiling of chromatin accessibility by combinatorial cellular indexing. Science. May 22, 2015;348(6237):910-4. doi: 10.1126/science.aab1601. Epub May 7, 2015.
Dekker, et al. Capturing chromosome conformation. Science. Feb. 15, 2002;295(5558):1306-11.
Drmanac et al., Sequencing by hybridization (SBH): advantages, achievements, and opportunities. Adv Biochem Eng Biotechnol. 2002;77 :75-101.
Epicentre., "EZ-Tn5TM Custom Transposome Construction Kits", http://www.epicentre.com, pp. 1-17, 2012.
Esser-Kahn, et al. Triggered release from polymer capsules. Macromolecules. 2011; 44:5539-5553.
Gaiti, et al. Epigenetic evolution and lineage histories of chronic lymphocytic leukaemia. Nature. May 2019;569(7757):576-580. doi: 10.1038/s41586-019-1198-z. Epub May 15, 2019.
Gangadharan et al., DNA transposon Hermes insert into DNA in nucleosome-free regions in vivo, Proc nat Ad Sci, Dec. 21, 2010, vol. 107, No. 51, pp. 1966-1972.
Gaublomme, et al. Nuclei multiplexing with barcoded antibodies for single-nucleus genomics. Nat Commun. Jul. 2, 2019;10(1):2907. doi: 10.1038/s41467-019-10756-2.
Gericke, et al. Functional cellulose beads: preparation, characterization, and applications. Chemical reviews 113.7 (2013): 4812-4836.
Gravina, et al. Single-cell genome-wide bisulfite sequencing uncovers extensive heterogeneity in the mouse liver methylome. Genome Biol. Jul. 5, 2016;17(1):150. doi: 10.1186/s13059-016-1011-3.
Gravina, et al. Single-cell, locus-specific bisulfite sequencing (SLBS) for direct detection of epimutations in DNA methylation patterns. Nucleic Acids Res. Aug. 18, 2015;43(14):e93. doi: 10.1093/nar/gkv366. Epub Apr. 19, 2015.
Green et al. Insertion site preference of Mu, Tn5, and Tn7 transposons. Mobile DNA 3.1 (2012): 3.
Greenleaf, et al. Assaying the epigenome in limited numbers of cells. Methods. Jan. 15, 2015;72:51-6. doi: 10.1016/j.ymeth.2014.10.010. Epub Oct. 22, 2014.

(56) References Cited

OTHER PUBLICATIONS

Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Islam, et al. Highly multiplexed and strand-specific single-cell RNA 5' end sequencing. Nat Protoc. Apr. 5, 2012;7(5):813-28. doi: 10.1038/nprot.2012.022.
Jaitin, et al. Massively parallel single-cell RNA-seq for marker-free decomposition of tissues into cell types. Science. Feb. 14, 2014;343(6172):776-9. doi: 10.1126/science.1247651.
Jia, et al. Single cell RNA-seq and ATAC-seq analysis of cardiac progenitor cell transition states and lineage settlement. Nat Commun. Nov. 199, 2018;9(1):4877. doi: 10.1038/s41467-018-07307-6.
Jin, et al. Genome-wide detection of DNase I hypersensitive sites in single cells and FFPE tissue samples. Nature. Dec. 3, 2015;528(7580):142-6. doi: 10.1038/nature15740.
Kilgore, et al. Single-molecule and population probing of chromatin structure using DNA methyltransferases. Methods. Mar. 2007;41(3):320-32.
Laird et al, Hairpin-bisulfite PCR: Assessing epigenetic methylation patterns on complementary strands of individual DNA molecules, 2004, PNAS, 101, 204-209.
Lake, et al. "Integrative Single-Cell Analysis by Transcriptional and Epigenetic States in Human Adult Brain". Apr. 19, 2017. doi: https://doi.org/10.1101/128520.
Madl, et al. "Bioorthogonal Strategies for Engineering Extracellular matrices", Madal, Chritopher, Adv. Funct. Master. Jan. 19, 2018, vol. 28, 1706046, pp. 1-21.
Nagano, et al. Single-cell Hi-C reveals cell-to-cell variability in chromosome structure. Nature. Oct. 3, 2013;502(7469):59-64. doi: 10.1038/nature12593. Epub Sep. 25, 2013.
Orakdogen, N. "Novel responsive poly(N,N-dimethylaminoethyl methacrylate) gel beads: preparation, mechanical properties and pH-dependent swelling behavior" J Polym Res (2012) 19:9914.
PARK. ChIP-seq: advantages and challenges of a maturing technology. Nature Reviews Genetics vol. 10, pp. 669-680 (2009).
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Ponnaluri, et al. NicE-seq: high resolution open chromatin profiling. Genome Biol. Jun. 28, 2017;18(1):122. doi: 10.1186/s13059-017-1247-6.
Pott, et al. Single-cell ATAC-seq: strength in numbers. Genome Biol. Aug. 21, 2015;16:172. doi: 10.1186/s13059-015-0737-7.
Preissl, et al. Single nucleus analysis of the chromatin landscape in mouse forebrain development. Posted Jul. 4, 2017. bioRxiv 159137; doi: https://doi.org/10.1101/159137.
Priest, et al. Generation of Monodisperse Gel Emulsions in a Microfluidic Device, Applied Physics Letters, 88:024106 (2006).
Ramani, et al. Massively multiplex single-cell Hi-C. Nat Methods. Mar. 2017; 14(3): 263-266. Published online Jan. 30, 2017.doi: 10.1038/nmeth.4155.
Ramskold et al. (2012) "Full-length mRNA-Seq from single-cell levels of RNA and individual circulating tumor cells" Nature Biotechnology 30(8):777-782.
Rotem, et al. Single-cell ChIP-seq reveals cell subpopulations defined by chromatin state. Nat Biotechnol. Nov. 2015;33(11):1165-72. doi: 10.1038/nbt.3383. Epub Oct. 12, 2015.
Saikia, et al. Simultaneous multiplexed amplicon sequencing and transcriptome profiling in single cells. Nat Methods. Jan. 2019; 16(1):59-62. doi: 10.1038/s41592-018-0259-9. Epub Dec. 17, 2018.

Schutsky, et al. APOBEC3A efficiently deaminates methylated, but not TET-oxidized, cytosine bases in DNA. Nucleic Acids Res. Jul. 27, 2017;45(13):7655-7665. doi: 10.1093/nar/gkx345.
Simon, et al., "Using formaldehyde-assisted isolation of regulatory elements (FAIRE) to isolate active regulatory DNA", Nature Protocols, 2012, 7(2): 256-267.
Smallwood, et al. Single-cell genome-wide bisulfite sequencing for assessing epigenetic heterogeneity. Nat Methods. Aug. 2014; 11(8):817-820. doi: 10.1038/nmeth.3035. Epub Jul. 20, 2014.
Smith, et al. Highly-multiplexed barcode sequencing: an efficient method for parallel analysis of pooled samples. Nucleic Acids Research, 38(13): e142 (2010).
Song, et al., "DNase-seq: A High-Resolution Technique for Mapping Active Gene Regulatory Elements across the Senome from Mammalian Cells", Cold Spring Harbor Laboratory Press, 2010, 2010(2), doi:10.1101/pdb.prot5384.
Thaxton, C.S. et al. "A Bio-Bar-Code Assay Based Upon Dithiothreitol Oligonucleotide Release" Anal Chem (2005) 77:8174-8178.
Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.
Ushijima et al., Detection and interpretation of altered methylation patterns in cancer cells, 2005, Nature reviews, 5, 223-231.
Uttamapinant, et al. Fast, cell-compatible click chemistry with copper-chelating azides for biomolecular labeling.Angew. Chem. Int. End. Engl., Jun. 11, 2012: 51(24) pp. 5852-5856.
Wang, et al. CoBatch for High-Throughput Single-Cell Epigenomic Profiling. Mol Cell. Oct. 3, 2019;76(1):206-216.e7. doi: 10.1016/j.molcel.2019.07.015. Epub Aug. 27, 2019.
Xu, et al. Single-cell lineage tracing by endogenous mutations enriched in transposase accessible mitochondrial DNA. Elife. Apr. 9, 2019;8. pii: e45105. doi: 10.7554/eLife.45105.
Zentner, et al. Surveying the epigenomic landscape, one base at a time. Genome Biol. Oct. 22, 2012;13(10):250. doi: 10.1186/gb4051.
Zhang, et al. One-step fabrication of supramolecular microcapsules from microfluidic droplets. Science. Feb. 10, 2012;335(6069):690-4. doi: 10.1126/science.1215416.
Zheng et al. Multiplex chromatin interactions with single-molecule precision. Nature 566(7745):558-562 (Feb. 2019).
Zhu, et al. An ultra high-throughput method for single-cell joint analysis of open chromatin and transcriptome. Nat Struct Mol Biol. Nov. 2019;26(11):1063-1070. doi: 10.1038/s41594-019-0323-x. Epub Nov. 6, 2019.
Corces, et al. Lineage-specific and single cell chromatin accessibility charts human hematopoiesis and leukemia evolution. Nat Genet. Oct. 2016; 48(10): 1193-1203. Published online Aug. 15, 2016. doi: 10.1038/ng.3646.
Co-pending U.S. Appl. No. 17/318,364, inventors Bava; Felice Alessio et al., filed May 12, 2021.
Co-pending U.S. Appl. No. 17/517,408, inventors Salmanzadeh; Alireza et al., filed Nov. 2, 2021.
Co-pending U.S. Appl. No. 17/518,213, inventor Lund; Paul Eugene, filed Nov. 3, 2021.
Co-pending U.S. Appl. No. 17/580,947, inventor Gibbons; Michael, filed Jan. 21, 2022.
Co-pending U.S. Appl. No. 17/831,835, inventor Martinez; Luigi Jhon Alvarado, filed Jun. 3, 2022.
Co-pending U.S. Appl. No. 17/957,781, inventor Bava; Felice Alessio, filed Sep. 30, 2022.
Co-pending U.S. Appl. No. 18/046,843, inventor Toh; Mckenzi, filed Oct. 14, 2022.
Song et al. 5-Hydroxymethylcytosine Signatures in Cell-Free DNA Provide Information about Tumor Types and Stages. Cell Research 27:1231-1242 (2017).

* cited by examiner

| Name | Control Experiment | |
|---|---|---|
| Cells (#) | 10,1112 | 10,8603 |
| Estimated number of cells (hg19) | 722 | 385 |
| Estimated number of cells (mm10) | 1,000 | 413 |
| Inferred multiplet rate | 0.0% | 2.5% |
| Fraction of transposition events in peaks in cell barcodes | 57.4% | 43.6% |
| Peaks detected | 159,825 | 170,905 |
| Median unique fragments per cell after downsampling to 30K high-quality reads per cell (hg19) | 11,210 | 6,678 |
| Median unique fragments per cell after downsampling to 30K high-quality reads per cell (mm10) | 11,155 | 7,897 |
| Median unique fragments per cell after downsampling to 30K raw reads per cell (hg19) | 9,953 | 5,155 |
| Median unique fragments per cell after downsampling to 30K raw reads per cell (mm10) | 7,330 | 6,231 |
| Enrichment score of CTCF motif sites | 1.52 | 1.52 |
| Enrichment score of transcription start sites | 7.58 | 6.83 |
| Fraction of fragments overlapping DNase HS regions (hg19) | 79.4% | 68.4% |
| Fraction of fragments overlapping DNase HS regions (mm10) | 65.8% | 55.5% |
| Fraction of fragments overlapping TSS (hg19) | 37.2% | 25.5% |
| Fraction of fragments overlapping TSS (mm10) | 34.7% | 29.8% |
| Fraction of fragments overlapping any targeted region (hg19) | 83.2% | 74.1% |
| Fraction of fragments overlapping any targeted region (mm10) | 78.1% | 68.6% |
| Fraction of fragments overlapping blacklisted regions (hg19) | 0.1% | 0.1% |
| Fraction of fragments overlapping blacklisted regions (mm10) | 0.4% | 0.2% |
| Fraction of fragments overlapping called peaks (hg19) | 56.2% | 38.4% |
| Fraction of fragments overlapping called peaks (mm10) | 65.1% | 52.6% |
| Fraction of fragments overlapping enhancer regions (hg19) | 21.3% | 19.0% |
| Fraction of fragments overlapping enhancer regions (mm10) | 28.5% | 27.3% |
| Fraction of fragments overlapping promoter regions (hg19) | 26.9% | 23.4% |
| Fraction of fragments overlapping promoter regions (mm10) | 29.4% | 24.8% |
| Fragments flanking a single nucleosome | 41.3% | 39.4% |
| Fragments in nucleosome free regions | 38.5% | 31.6% |
| Fraction of read pairs with a valid barcode | 94.9% | 98.6% |
| Fraction of read pairs with valid barcodes in non-cell barcodes | 15.8% | 8.6% |
| Fraction of total read pairs in mitochondria and in cell barcodes | 0.1% | 0.8% |
| Fraction of total read pairs that are non-duplicate and wasted read pairs | 27.0% | 19.8% |
| Ratio of mitochondrial read pairs in cell barcodes to usable read pairs in cell barcodes | 0.4% | 1.0% |

*FIG. 17*

METHODS AND SYSTEMS FOR CHARACTERIZING NUCLEIC ACID MOLECULES

CROSS-REFERENCE

This application claims the benefit of U.S. Provisional Patent Application No. 62/682,119, filed Jun. 7, 2018, which application is entirely incorporated herein by reference.

BACKGROUND

A sample may be processed for various purposes, such as identification of a type of moiety within the sample. The sample may be a biological sample. Biological samples may be processed, such as for detection of a disease (e.g., cancer) or identification of a particular species. There are various approaches for processing samples, such as polymerase chain reaction (PCR) and sequencing.

Biological samples may be processed within various reaction environments, such as partitions. Partitions may be wells or droplets. Droplets or wells may be employed to process biological samples in a manner that enables the biological samples to be partitioned and processed separately. For example, such droplets may be fluidically isolated from other droplets, enabling accurate control of respective environments in the droplets.

Biological samples in partitions may be subjected to various processes, such as chemical processes or physical processes. Samples in partitions may be subjected to heating or cooling, or chemical reactions, such as to yield species that may be qualitatively or quantitatively processed.

SUMMARY

Recognized herein is a need for the improved methods and systems for characterizing nucleic acid molecules from a single cell or a population of cells. Such cells include, but are not limited to, cancer cells, fetal cells, and immune cells involved in immune responses. Provided herein are methods, compositions and systems for analyzing individual cells or a small population of cells, including the analysis and attribution of the analytes from and to these individual cells or cell populations. Nucleic acid molecules from a single cell or a population of cells may be characterized by assessing epigenome, genome, transcriptome, and/or chromatin accessibility.

In an aspect, the present disclosure provides a method for determining an epigenetic state or characteristic of a nucleic acid molecule from a single cell, comprising: a) providing a cell bead comprising the nucleic acid molecule from the single cell, wherein the nucleic acid molecule contains or is suspected of containing one or more epigenetic features; b) partitioning the cell bead in a single partition among a plurality of partitions; c) in the partition, synthesizing a barcoded nucleic acid molecule from the nucleic acid molecule, which barcoded nucleic acid molecule comprises a cell barcode, wherein the cell barcode is indicative of the single cell from which the nucleic acid molecule originates; d) processing the barcoded nucleic acid molecule or a derivative thereof to identify the one or more epigenetic features and the cell barcode; and e) using the one or more epigenetic features and the cell barcode to determine the epigenetic state or characteristic of the nucleic acid molecule as being associated with the single cell.

In some embodiments of aspects provided herein, the nucleic acid molecule is encapsulated in the cell bead. In some embodiments of aspects provided herein, the method further comprises, prior to (a), lysing the cell to release a content of the cell. In some embodiments of aspects provided herein, the method further comprises, subsequent to the lysing, treating the content with one or more proteases. In some embodiments of aspects provided herein, the method further comprises, prior to (a), encapsulating the cell or a derivative thereof in a mixture comprising a polymer(s) or polymer precursor(s). In some embodiments of aspects provided herein, the method further comprises, prior to (a), producing the cell bead by performing a gelation reaction. In some embodiments of aspects provided herein, the cell bead further comprises one or more reagents for processing the nucleic acid molecule. In some embodiments of aspects provided herein, the method in (a) further comprises providing a plurality of gel beads, and wherein the method in (b) further comprises partitioning the plurality of gel beads into the plurality of partitions, wherein the partition comprises a gel bead of the plurality of gel beads, and wherein the gel bead comprises the cell barcode in (c). In some embodiments of aspects provided herein, the method further comprises, subsequent to (a), performing one or more reactions within the cell bead, the one or more reactions transforming at least a portion of the one or more epigenetic features of the nucleic acid molecule. In some embodiments of aspects provided herein, the one or more reactions are selected from the group consisting of nucleic acid amplification, bisulfite treatment, oxygenase treatment, enzymatic deamination, proteinase treatment, methyltransferase treatment, treatment with methylation-specific restriction enzyme, ligase treatment, template switching treatment, micrococcal nuclease digestion, transposon insertion, cross-linking treatment, restriction digestion, and proximity ligation. In some embodiments of aspects provided herein, the one or more epigenetic features comprise methylation of the nucleic acid molecule, hydroxymethylation of the nucleic acid molecule, modification of histone proteins associated with the nucleic acid molecule, chromatin packaging associated with the nucleic acid molecule, and chromatin accessibility associated with the nucleic acid molecule. In some embodiments of aspects provided herein, the processing in (d) comprises determining locations of a subset of the one or more epigenetic features with respect to the nucleic acid molecule. In some embodiments of aspects provided herein, the plurality of partitions is a plurality of wells, and wherein the single partition is a well. In some embodiments of aspects provided herein, the plurality of partitions is a plurality of wells, and wherein the single partition is a well. In some embodiments of aspects provided herein, the plurality of partitions is a plurality of droplets, and wherein the single partition is a droplet. In some embodiments of aspects provided herein, the epigenetic state or characteristic of the nucleic acid molecule is increased expression level of the nucleic acid molecule, or decreased expression level of the nucleic acid molecule.

Another aspect of the present disclosure provides a system for determining an epigenetic state or characteristic of a nucleic acid molecule from a single cell, comprising: a) a first controller programmed to: (i) direct partitioning of a biological particle in a single partition among a plurality of partitions; and (ii) in the partition, direct synthesis of a barcoded nucleic acid molecule from the nucleic acid molecule, which barcoded nucleic acid molecule comprises a cell barcode, wherein the biological particle comprising the nucleic acid molecule from the single cell, wherein the nucleic acid molecule contains or is suspected of containing one or more epigenetic feature; and b) a second controller programmed to process the barcoded nucleic acid molecule or a derivative thereof to identify the one or more epigenetic features and the cell barcode.

In some embodiments of aspects provided herein, the first controller is the second controller. In some embodiments of aspects provided herein, the system further comprises a third controller programmed to use the one or more epigenetic features and the cell barcode to determine that the epigenetic state or characteristic of the nucleic acid molecule are associated with the single cell. In some embodiments of aspects provided herein, each of the first and second controllers comprises one or more computer processors.

In an aspect, the present disclosure provides a method for determining an epigenetic state or characteristic of a nucleic acid molecule from a single cell, comprising: (a) providing a cell bead comprising the nucleic acid molecule from the single cell, wherein the nucleic acid molecule contains or is suspected of containing one or more epigenetic features; (b) partitioning the cell bead with a nucleic acid barcode molecule comprising a cell barcode sequence in a single partition among a plurality of partitions; (c) in the partition, using the nucleic acid molecule and the nucleic acid barcode molecule to synthesize a barcoded nucleic acid molecule, which barcoded nucleic acid molecule comprises the cell barcode sequence, wherein the cell barcode sequence is indicative of the single cell from which the nucleic acid molecule originates; (d) processing the barcoded nucleic acid molecule or a derivative thereof to identify the one or more epigenetic features and the cell barcode; and (e) using the one or more epigenetic features and the cell barcode sequence to determine the epigenetic state or characteristic of the nucleic acid molecule as being associated with the single cell, wherein, subsequent to (a), one or more reactions selected from the group consisting of oxygenase treatment, enzymatic deamination, proteinase treatment, methyltransferase treatment, treatment with methylation-specific restriction enzyme, micrococcal nuclease (Mnase) digestion, deoxyribonuclease (DNase) digestion, cross-linking treatment, immunoprecipitation, restriction digestion, transposase-mediated fragmentation, and proximity ligation are performed within the cell bead, the one or more reactions transforming at least a portion of the one or more epigenetic features of the nucleic acid molecule.

In some embodiments, the nucleic acid molecule is encapsulated in the cell bead.

In some embodiments, the method further comprises, prior to (a), lysing the single cell to release a content of the single cell. In some embodiments, the method further comprises, subsequent to the lysing, treating the content with one or more proteases.

In some embodiments, the method further comprises, prior to (a), encapsulating the single cell or a derivative thereof in a mixture comprising a polymer(s) or polymer precursor(s). In some embodiments, the method further comprises, prior to (a), producing the cell bead by performing a gelation reaction.

In some embodiments, the cell bead further comprises one or more reagents for processing the nucleic acid molecule.

In some embodiments, (a) further comprises providing a plurality of gel beads, and wherein (b) further comprises partitioning the plurality of gel beads into the plurality of partitions, wherein the partition comprises a gel bead of the plurality of gel beads, and wherein the gel bead comprises the cell barcode sequence in (c).

In some embodiments, the one or more epigenetic features comprise methylation of the nucleic acid molecule, hydroxymethylation of the nucleic acid molecule, modification of histone proteins associated with the nucleic acid molecule, chromatin packaging associated with the nucleic acid molecule, and chromatin accessibility associated with the nucleic acid molecule.

In some embodiments, the processing in (d) comprises determining locations of a subset of the one or more epigenetic features with respect to the nucleic acid molecule.

In some embodiments, the plurality of partitions is a plurality of wells, and wherein the single partition is a well. In some embodiments, the plurality of partitions is a plurality of droplets, and wherein the single partition is a droplet.

In some embodiments, the epigenetic state or characteristic of the nucleic acid molecule is increased expression level of the nucleic acid molecule, or decreased expression level of the nucleic acid molecule.

In another aspect, the present disclosure provides a method for determining an epigenetic state or characteristic of a nucleic acid molecule from a single cell, comprising: (a) providing a cell bead comprising the nucleic acid molecule from the single cell, wherein the nucleic acid molecule contains or is suspected of containing one or more epigenetic features; (b) partitioning the cell bead with a nucleic acid barcode molecule comprising a cell barcode sequence in a single partition among a plurality of partitions; (c) in the partition, using the nucleic acid molecule and the nucleic acid barcode molecule to synthesize a barcoded nucleic acid molecule, which barcoded nucleic acid molecule comprises the cell barcode sequence, wherein the cell barcode sequence is indicative of the single cell from which the nucleic acid molecule originates; (d) processing the barcoded nucleic acid molecule or a derivative thereof to identify the one or more epigenetic features and the cell barcode; and (e) using the one or more epigenetic features and the cell barcode sequence to determine the epigenetic state or characteristic of the nucleic acid molecule as being associated with the single cell, wherein the one or more epigenetic features comprise hydroxymethylation of the nucleic acid molecule or modification of histone proteins associated with the nucleic acid molecule.

In some embodiments, the nucleic acid molecule is encapsulated in the cell bead. In some embodiments, the method further comprises, prior to (a), lysing the cell to release a content of the cell. In some embodiments, the method further comprises, subsequent to the lysing, treating the content with one or more proteases. In some embodiments, the method further comprises, prior to (a), encapsulating the cell or a derivative thereof in a mixture comprising a polymer(s) or polymer precursor(s). In some embodiments, the method further comprises, prior to (a), producing the cell bead by performing a gelation reaction.

In some embodiments, the cell bead further comprises one or more reagents for processing the nucleic acid molecule.

In some embodiments, (a) further comprises providing a plurality of gel beads, and wherein (b) further comprises partitioning the plurality of gel beads into the plurality of partitions, wherein the partition comprises a gel bead of the plurality of gel beads, and wherein the gel bead comprises the cell barcode sequence in (c).

In some embodiments, the method further comprises, subsequent to (a), performing one or more reactions within the cell bead, the one or more reactions transforming at least a portion of the one or more epigenetic features of the nucleic acid molecule. In some embodiments, the one or more reactions are selected from the group consisting of nucleic acid amplification, bisulfite treatment, oxygenase treatment, enzymatic deamination, proteinase treatment, methyltransferase treatment, treatment with methylation-specific restriction enzyme, ligase treatment, template switching treatment, micrococcal nuclease digestion, transposon insertion, cross-linking treatment, restriction digestion, and proximity ligation.

In some embodiments, the processing in (d) comprises determining locations of a subset of the one or more epigenetic features with respect to the nucleic acid molecule.

In some embodiments, the plurality of partitions is a plurality of wells, and wherein the single partition is a well. In some embodiments, the plurality of partitions is a plurality of droplets, and wherein the single partition is a droplet.

In a further aspect, the present disclosure provides a system for determining an epigenetic state or characteristic of a nucleic acid molecule from a single cell, comprising: (a) a cell bead comprising the nucleic acid molecule from the single cell, wherein the nucleic acid molecule contains or is suspected of containing one or more epigenetic features; (b) a nucleic acid barcode molecule comprising a barcode sequence; (c) reagents configured to direct performance of one or more reactions on the nucleic acid molecule in the cell bead, wherein the one or more reactions are selected from the group consisting of oxygenase treatment, enzymatic deamination, proteinase treatment, methyltransferase treatment, treatment with methylation-specific restriction enzyme, micrococcal nuclease (MNase) digestion, deoxyribonuclease (DNase) digestion, cross-linking treatment, immunoprecipitation, restriction digestion, transposase-mediated fragmentation, and proximity ligation, wherein the one or more reactions are configured to transform or isolate at least a portion of the one or more epigenetic features of the nucleic acid molecule; and (d) a device comprising a plurality of partitions, wherein a partition of the plurality of partitions comprises: (i) the cell bead; and (ii) the nucleic acid barcode molecule, wherein the system is configured to generate a barcoded nucleic acid molecule.

In some embodiments, the plurality of partitions is a plurality of aqueous droplets. In some embodiments, the device is a microfluidic device comprising a plurality of channels configured to generate the plurality of aqueous droplets.

In some embodiments, the plurality of partitions is a plurality of microwells. In some embodiments, the device is a microwell array comprising 1,000 microwells.

In some embodiments, the nucleic acid barcode molecule is attached to a bead and wherein the partition comprises the bead. In some embodiments, the nucleic acid barcode molecule is releasable from the bead upon application of a stimulus. In some embodiments, the stimulus is a chemical stimulus and wherein the partition comprises the stimulus. In some embodiments, the bead is a gel bead. In some embodiments, the gel bead is degradable upon application of a stimulus. In some embodiments, the stimulus is a chemical stimulus and wherein the partition comprises the stimulus.

In some embodiments, the system further comprises a sequencing component comprising a sequencing instrument configured to generate sequencing reads corresponding to the barcoded nucleic acid molecule. In some embodiments, the system further comprises a computing component comprising a processor, a user interface, and an electronic display, wherein the computing component is configured to analyze the sequencing reads and display an analysis of nucleic acid sequencing data on the electronic display. In some embodiments, the analysis comprises a representation of the epigenetic features of the epigenetic features.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 15A shows representative ATAC-seq workflows while FIG. 15B shows representative insert size distribution.

FIG. 17 shows representative sequencing metrics from samples tagmented prior to cell bead gelation.

DETAILED DESCRIPTION

Figure 1:
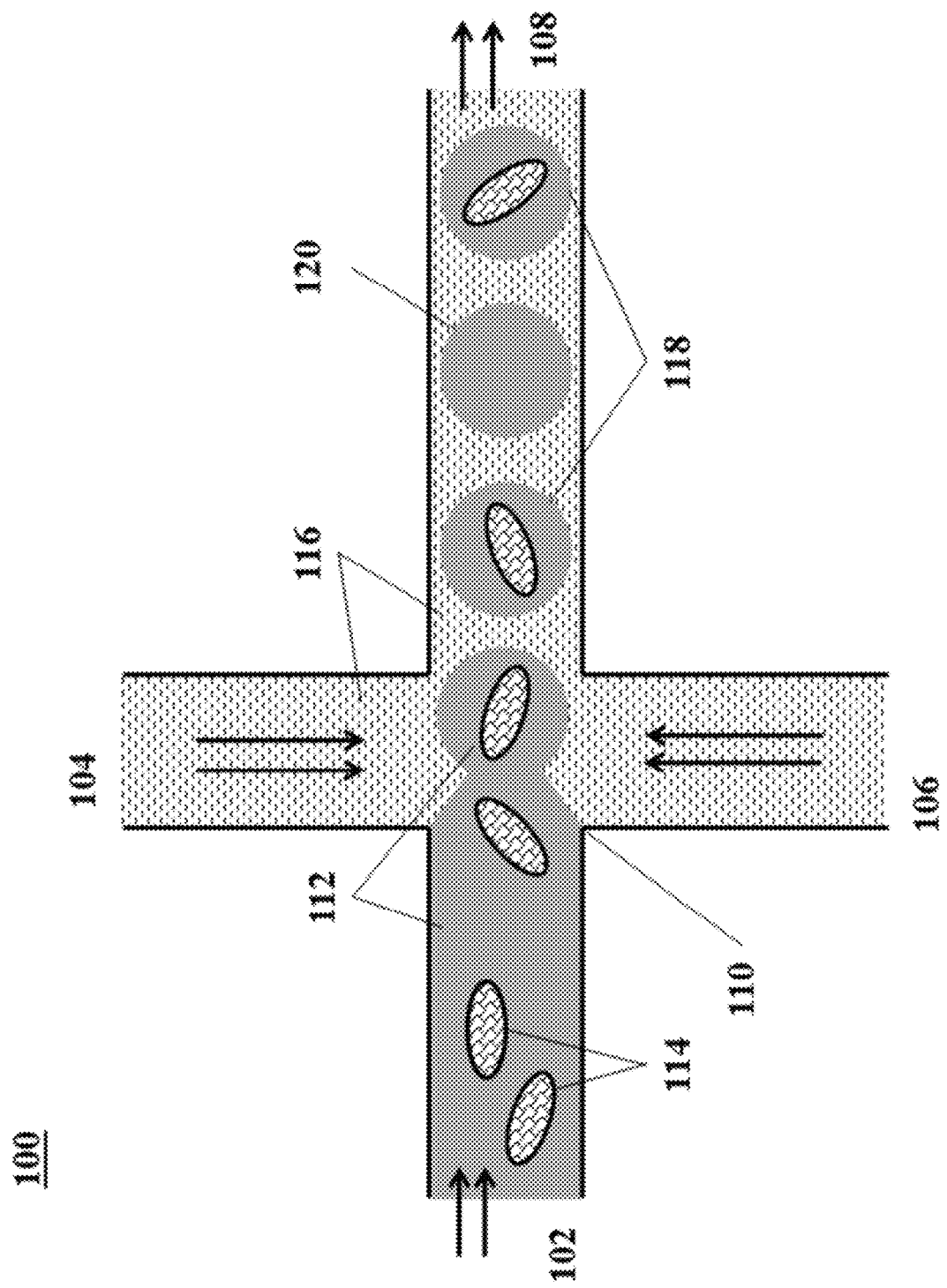
FIG. 1 shows an example of a microfluidic channel structure for partitioning individual biological particles.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver)

covered with a coating comprising one or more polymers. Such coating may be disruptable or dissolvable.

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally, refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

The term "epigenetic state," as used herein, generally refers to the state of alterations to gene structure and function that are not due to changes in the corresponding DNA sequence. An epigenetic state may refer to a state relating to or arising from non-genetic influences on gene expression or genome organization.

The term "epigenetic feature," as used herein, generally refers to a structural alteration or other alteration in the DNA or biological molecules associated with the DNA, excluding alterations in the primary nucleotide sequence of a gene. The epigenetic features, when combined, may result in modification of the DNA functions, including, for example, diminished or enhanced gene expression. For examples, chromatin packaging may be a mechanism of epigenetic gene regulation which can be implicated in cell lineage commitment and lineage-specific gene expression. Transcriptionally inactive, or silenced, heterochromatin can be more tightly packaged around histone proteins than transcriptionally active euchromatin due to differences in DNA methylation patterns and post-translational histone modifications. Due to its accessibility for measurement, DNA methylation can be a marker of chromatin packaging.

Biological samples may be processed en masse without considering heterogeneity of the samples. Such sample processing may represent an average of the cells in the sample. Existing methods lack sample processing methods that reveal cell-to-cell variations in the sample. Further, existing methods can suffer from inefficient sample preparation if relatively large amounts of biological samples are required for analysis.

Provided herein are systems and methods for characterizing nucleic acid molecules from a biological particle such as a cell or cell bead. Nucleic acid molecules may be characterized by assessing the epigenome, genome, transcriptome, and/or chromatin accessibility.

In some examples, entrapment or encapsulation of cells (or cell nuclei) within particles such as cell beads may facilitate the interrogation of epigenetic variations at the single cell level. For example, a single cell (or cell nucleus) may be encapsulated within a particle (e.g., a cell bead). The single cell may be lysed to release nucleic acid molecules included therein, including deoxyribonucleic acid (DNA). Such nucleic acid molecules may remain encapsulated in the particle, which may comprise a polymer network configured to retain nucleic acid molecules (e.g., by restricting certain movements of nucleic acid molecules). For description of cell beads and cell bead encapsulation and polymer compositions, systems, and methodologies that may be useful according to the present disclosure, see, e.g., U.S. Patent Publication Nos. 2018-0216162 and 2019-0100632, both of which are incorporated by reference in their entireties. In some cases, the single cell may be treated with one or more proteinases to release nucleic acid molecules (e.g., DNA) included therein. A cell entrained in a particle need not be lysed. For example, a cell or cell nucleus encapsulated in a particle (e.g., the cell bead) may be encapsulated under conditions sufficient to substantially maintain a structure of the cell, such as its chromatin structure. In some cases, such a cell (or nucleus) may be permeabilized to provide access to the nucleic acid molecules (e.g., DNA, such as chromatin) therein. The structure of chromatin of or derived from a cell (e.g., a cell encapsulated in a cell bead) may be interrogated by, for example, transposon-mediated insertion of tags within the particle (e.g., the cell bead) such that a treated nucleic acid molecule is also encapsulated within the particle. In some cases, a transposon insertion method used to interrogate the structure of chromatin encapsulated in a particle (e.g., a cell bead) may comprise an Assay for Transposase Accessible Chromatin using sequencing (ATAC-seq) method, which is based on direct in vitro transposition of sequencing adapters into native chromatin. For a description of ATAC-seq and ATAC-seq compositions, systems, and methodologies that may be useful according to the present disclosure, see, e.g., U.S. Pat. No. 10,059,989 and U.S. Patent Publication No. 2018-0340171, both of which are incorporated by reference in their entireties. Encapsulated nucleic acid molecules may be used to interrogate epigenetics at the single cell level using methods including, but not limited to: characterization of methylation by bisulfite treatment; characterization of methylation using methylation-specific restriction enzymes; chromatin accessibility assessment by micrococcal nuclease digestion; identification of chromatin accessible regions by transposon insertion; and interrogation of spatial arrangement by crosslinking, restriction digest, proximity ligation followed by barcoding.

In some cases, a particle (e.g., cell bead) comprising an encapsulated nucleic acid molecule (e.g., DNA molecule) can be subjected to bisulfite treatment, which treatment may convert a cytosine base of the nucleic acid molecule into a uracil base unless the cytosine is 5-methylated. The particle (e.g., cell bead) may provide a way to maintain the encapsulated nucleic acid molecule individually packaged without interference from other nucleic acid molecules of other cells to maintain single cell characteristics. Bisulfite-treated particles (e.g., cell beads) can also be co-encapsulated with other particles such as particles containing nucleic acid barcode molecules (e.g., barcode-containing particles such as beads, e.g., gel beads). For example, bisulfite-treated particles and other particles may be co-encapsulated within partitions such as wells of a microwell array or droplets of an emulsion. These partitions (e.g., droplets) can contain all required enzymes for one or more nucleic acid amplification and barcode attachment methods such as amplification by isothermal methods or thermocycling methods, and attachment of barcode by priming and extension or by ligation or by template switching methods.

In some cases, a nucleic acid molecule (e.g., DNA molecule) of a cell that is encapsulated in a particle (e.g., cell bead) may remain encapsulated after the nucleic acid molecule is digested with an enzyme specific for methylated groups. Examples of such enzymes may include, but are not limited to, Mspll restriction enzymes.

Other particle (e.g., cell bead) treatments can be modified to lyse a cell or nucleus encapsulated within a particle (e.g., cell bead) to provide access to a nucleic acid molecule therein without unpackaging the encapsulated nucleic acid molecule (e.g., DNA). Such a treatment may be performed in such a way as to maintain the chromatin structure of the cell of a given particle (e.g., cell bead). The preserved conformation of the chromatin may facilitate the interrogation of DNA accessibility and/or spatial DNA arrangement within the cell.

Methods for Epigenetic Characterization of Nucleic Acid Molecules

In an aspect, the present disclosure provides a method for determining an epigenetic state or characteristic of a nucleic acid molecule from a single cell. The epigenetic state or characteristic may comprise, for example, methylation of said nucleic acid molecule, hydroxymethylation of said nucleic acid molecule, modification of histone proteins associated with said nucleic acid molecule, chromatin packaging associated with said nucleic acid molecule, chromatin accessibility associated with said nucleic acid molecule, and/or DNA-binding protein occupancy. The method comprises providing a biological particle (e.g., a cell or nucleus) comprising the nucleic acid molecule from the single cell. The nucleic acid molecule may contain or be suspected of containing the one or more epigenetic features. The biological particle may be a cell bead (e.g., as described herein). The biological particle may be partitioned in a single partition among a plurality of partitions (e.g., a plurality of droplets or wells). The biological particle may be partitioned with a nucleic acid barcode molecule (e.g., attached to a bead as described elsewhere herein) comprising a cell barcode sequence. In some instances, partitions of said plurality of partitions will comprise a nucleic acid barcode molecule comprising a barcode sequence that is different from other barcode sequences in other partitions of the plurality of partitions. Accordingly, each analyte derived from a biological particle (e.g., cell bead) in an individual partition can be distinguished from other analytes from other biological particles in other partitions using the unique cell barcode. In the partition, a nucleic acid molecule of the biological particle and the nucleic acid barcode molecule may be used to synthesize (e.g., generate) a barcoded nucleic acid molecule corresponding to an epigenetic feature (e.g., methylations status, accessible chromatin, etc.) from said biological particle. The barcoded nucleic acid molecule may comprise the cell barcode sequence of the nucleic acid barcode molecule. The cell barcode sequence may be indicative of (or identify) the single cell (e.g., present in or derived from a single cell bead) from which the nucleic acid molecule originates. Next, the barcoded nucleic acid molecule or a derivative thereof may be processed (e.g., a sequencing library generated) to identify the one or more epigenetic features and the cell barcode sequence (e.g., by nucleic acid sequencing). The one or more epigenetic features and the cell barcode sequence may then be used to determine the epigenetic state or characteristic of the nucleic acid molecule as being associated with the single cell. The method may further comprise performing one or more reactions within a biological particle (e.g., within a cell bead). In some instances, the one or more reactions are performed: (1) prior to any cell bead generation steps (e.g., prior to gelation and encapsulation in a polymer and/or crosslinked matrix); (2) concurrent with any cell bead generation steps; and/or (3) after cell bead generation. In some instances, the one or more reactions are performed: (1) prior to any partitioning and/or barcoding steps; (2) concurrent with any partitioning and/or barcoding steps; and/or (3) after any partitioning and/or barcoding steps. The one or more reactions may transform at least a portion of the one or more epigenetic features of a nucleic acid molecule. Examples of such reactions include, but are not limited to, nucleic acid amplification, bisulfite treatment, oxygenase treatment, enzymatic deamination, proteinase treatment, methyltransferase treatment, treatment with methylation-specific restriction enzyme, ligase treatment, template switching treatment, micrococcal nuclease digestion, transposon insertion, crosslinking treatment, restriction digestion, and proximity ligation.

A cell bead may be prepared by any useful method. Similarly, a bead (e.g., gel bead) used to process one or more components (e.g., nucleic acid molecules) of a cell bead may be prepared by any useful method. In some cases, a cell bead may be prepared by combining a cell, cell nucleus, or component thereof and one or more polymers and/or polymer precursors and subjecting the combination to a polymerization or crosslinking condition. In an example, the one or more polymers and/or polymer precursors may comprise two different polymers and/or polymer precursors and the cell bead is generated by subjecting the combination to a condition sufficient to generate a plurality of linkages between the two different polymers and/or polymer precursors. The plurality of linkages may comprise triazole moieties. In such a system, click chemistry may be used to generate the linkages between the two different polymers and/or polymer precursors. For example, the first polymer or polymer precursor may comprise a plurality of azide moieties and the second polymer or polymer precursor may comprise a plurality of alkyne moieties. Reaction between azide and alkyne moieties may be promoted via a copper catalyst or the use of strained alkynes, for example. For an exemplary description of cell beads and cell bead encapsulation and polymer compositions, systems, and methodologies, see, e.g., U.S. Patent Publication Nos. 2018-0216162 and 2019-0100632, both of which are incorporated by reference in their entireties. A bead used to process components of a cell bead (e.g., a bead comprising a nucleic acid barcode molecule) may be similarly generated, where one or more polymers or polymer precursors may be linked to the nucleic acid barcode molecule prior to generation of the bead. Alternatively, the nucleic acid barcode molecule may be attached to the bead subsequent to its generation.

A bead, a polymer, or polymer precursors (e.g., monomer units that may polymerize and form said polymer) may be coupled to, attached to, functionalized, or otherwise associated with a molecule (e.g., a nucleic acid molecule or a nucleic acid barcode molecule) using conjugation chemistry. Conjugation chemistry as described herein refers to any suitable chemical reaction that links, couples, or attaches a first molecule (e.g., a polymer or a bead) with a second molecule (e.g., a binding agent such as an analyte-specific binding agent, a nucleic acid molecule, a nucleic acid barcode molecule, or any other molecule). Conjugation chemistry may comprise bioconjugation chemistry and click chemistry. Conjugation chemistry may comprise biological interactions (e.g., biotin/strepdavidin interactions) and/or bioorthogonal reactions. In some cases, coupling or attachment of molecules (e.g., nucleic acids, binding agents, etc.) to a bead, cell bead, or polymer as described herein may be performed using click chemistry.

Click chemistry, as described herein, may comprise any type of click reaction suitable for the functionalization of beads, cell beads, polymers, or precursors thereof with various types of molecules such as nucleic acid molecules, nucleic acid barcode molecules, binding agents (e.g., analyte-specific binding agents), etc. Examples of click chemistry reactions (also referred to herein as "click reactions") that may be used in combination with the methods, systems, and kits provided herein include, but are not limited to, transition-metal catalyzed or strain-promoted azide-alkyne cycloadditions (e.g., Huisgen azide-alkyne 1,3-dipolar cycloaddition, copper-catalyzed azide-alkyne cycloaddition (CuAAC), strain-promoted alkyne-azide cycloaddition, and/or ruthenium-catalyzed azide-alkyne cycloaddition (RuAAC)), Diels-Alder reactions such as inverse-electron demand Diels-Alder reaction (e.g., tetrazine-trans-cyclooctene reactions), or photo-click reactions (e.g., alkene-tetrazole photoreactions).

A bead, cell bead, polymer, or precursor thereof may be attached to one or more sets of molecules (e.g., binding agents, nucleic acid molecules, and/or nucleic acid barcode molecules) using such click chemistry. Thus, a bead, cell bead, polymer, or precursor thereof may comprise (e.g., may be functionalized with) a first functional group. The first functional group may be a first reactant for a click reaction. The one or more sets of molecules (e.g., binding agents and/or nucleic acid molecules) that may be attached to the bead, cell bead, polymer, or precursor thereof, may comprise a second functional group. The second functional group may be a second reactant for a click reaction. The click reaction may be a copper-catalyzed azide-alkyne cycloaddition reaction, an inverse-electron demand Diels-Alder reaction, etc. In an example, a bead, cell bead, polymer, or precursor thereof is modified with an analyte-specific binding agent using a copper-catalyzed azide-alkyne cycloaddition click reaction. Such reaction can comprise an azide-functionalized analyte-specific binding agent and an alkyne-functionalized bead, cell bead, polymer, or precursor thereof (e.g., a cell bead comprising a cell encapsulated in a polymer matric (e.g., a hydrogel matrix)). Click reaction may occur between the azide-functionalized analyte-specific binding agent and alkyne-functionalized bead, cell bead, polymer, or precursor thereof, thereby attaching the binding agent to the bead, cell bead, polymer, or precursor thereof.

In addition to using click chemistry, a molecule (e.g., a binding agent or nucleic acid molecule) can be attached to a bead, cell bead, polymer, or precursor thereof, using various other bioconjugation or coupling methods. Such bioconjugation methods can include various conjugation strategies and functional group modifications such as mesylate formation, sulfur alkylation, NHS ester formation, carbamate formation, carbonate formation, amide bond formation, or any combination thereof. Such strategies and functional group modifications can be used for various reaction types such nucleophilic and/or electrophilic substitution reaction, nucleophilic and/or electrophilic addition reaction, and other suitable reaction types. In some cases, activated carboxylic acids can react with nucleophiles such as amines. In some cases, the carboxylic acid can be attached to a bead, cell bead, polymer, or precursor thereof, and the nucleophilic group such as an amine can be attached to the molecule (e.g., a nucleic acid molecule or a binding agent) to be attached to said bead, cell bead, polymer, or precursor thereof. Such amide bond formation reactions can include EDC/NHS (e.g., via 1-ethyl-3-(3-dimethyl-aminopropyl) carbodiimide (EDC) and N-hydroxysuccinimide (NETS) or 4-(4,6-dimethoxy-1,3,5-triazin-2-yl)-4-methylmorpholinium chloride (DMTMM)) mediated coupling reactions, wherein an activated ester (e.g., an NHS ester attached to a bead surface) can react with an amine (e.g., an amine of a nucleic acid molecule) to form an amide bond, thereby attaching said molecule (e.g., a nucleic acid molecule) to said bead (e.g., a gel bead). Any other suitable bioconjugation reactions can be used to attach a molecule to a bead.

A biological particle can be a single biological particle, such as a cell or a cell encapsulated in polymer matrix (e.g., cell bead) as described elsewhere herein. A biological particle can be a plurality of biological particles, such as a plurality of cells. A biological particle can comprise a live or fixed cell, such as a formalin-fixed paraffin-embedded (FFPE) cell. A biological particle can comprise any cellular component or derivative or combination thereof, such as a nucleic acid molecule (e.g., deoxyribonucleic acid (DNA) or ribonucleic acid (RNA), nucleus, etc. A biological particle can be encapsulated, entrapped, or entrained in a gel matrix to preserve the biological particle. The biological particle can be encapsulated prior to or subsequent to partitioning the biological particle into a partition (e.g., a droplet or well). In some cases, the biological particle can comprise a single cell. The single cell can comprise a nucleic acid molecule (e.g., a DNA or RNA molecule). The single cell comprising a nucleic acid molecule can be encapsulated to form a cell bead (e.g., as described herein). The single cell may be encapsulated in a mixture of polymer(s) and/or polymer precursor(s). The mixture of polymer(s) and/or polymer precursor(s) may be allowed to polymerize and/or crosslink in a reaction to yield a cell bead. The single cell can be lysed to release one or more components of the cell, such as one or more nucleic acid molecules (e.g., as described herein). Upon lysis, the contents of the cell may be treated with one or more proteases in order to break down proteins and peptides by hydrolyzing peptide bonds.

Cell beads comprising a nucleic acid molecule attached thereto can be generated using any suitable method(s) described herein. For a description of cell beads and cell bead encapsulation and polymer compositions, systems, and methodologies, see, e.g., U.S. Patent Publications Nos. 2018-0216162 and 2019-0100632, both of which are incorporated by reference in their entireties. For example, in some embodiments, a biological particle (e.g., a cell or cell nucleus) is partitioned into a partition (e.g., a droplet in an emulsion) with polymeric or gel precursors. In some instances, one or more nucleic acid molecules comprising, e.g., one or more functional sequences may be co-partitioned with the cell or nucleus for inclusion within the cell bead. In some instances, the one or more functional sequences include an adapter sequence, a barcode sequence, unique molecular index, a primer or primer binding sequence, a sequencing primer sequence (such as R1 or R2 or partial sequences thereof), a flow cell attachment sequence (such as P5 or P7 or partial sequences thereof), a poly-T sequence, etc. The partition may be subjected to conditions sufficient to polymerize or cross-link the polymeric or gel precursors to generate the cell bead, wherein the cell bead encapsulates the biological particle and, if present, the one or more nucleic acid molecules comprising one or more functional sequences.

In some cases, cell beads can be synthesized in one-step procedures, e.g., polymerization and concurrent cross-linking reactions of multifunctional monomers. In other cases, cell beads can be synthesized in multi-step procedures, e.g., polymerization of monomers first, followed by crosslinking reactions by using, e.g., orthogonal, reactive groups that can respond to different conditions to allow stepwise approaches.

Cell beads can be synthesized by techniques that can create a crosslinked polymer. In some cases, copolymerization/cross-linking free radical polymerizations can be used to produce hydrogels by reacting hydrophilic monomers with multifunctional crosslinking molecules. This can be done by, for example, linking polymer chains via a chemical reaction(s), using ionizing radiation to generate main-chain free radicals which can recombine as crosslinking junctions, or physical interactions such as entanglements, electrostatics, and crystallite formation. Types of polymerization can include, for example, bulk, solution, and suspension polymerization.

Suspension polymerization or dispersion polymerization can be employed in water-in-oil or emulsion processes, sometimes called "inversion suspension." In some cases, the monomers and initiators can be dispersed in the oil or hydrocarbon phase as a homogenous mixture. In some cases, two types of polymer molecules can be first produced, each having a reactive, crosslinking moiety for cross-linking purposes. Then these two types of polymer molecules can be enclosed in an emulsion such that the two reactive, crosslinking moieties can react and form crosslinks between the two types of polymers, thereby completing the synthesis of the hydrogel.

In some cases, cell beads can be synthesized from monomers, polymerization initiators, and crosslinking reagents. After the polymerization reactions are complete, the hydrogels formed can be separated from remaining starting materials, unwanted by-products, etc. The length of the polymer formed can be controlled depending on the desired properties of the hydrogels.

Types of polymerizations employed to synthesize hydrogels can include, but are not limited to, free radical polymerization, controlled radical polymerization, crosslinking polymerization, networks formation of water-soluble polymers, and radiation crosslinking polymerization, etc. Polymerization can be initiated by initiators or free-radical generating compounds, such as, for example, benzoyl peroxide, 2,2-azo-isobutyronitrile (AIBN), and ammonium peroxodisulphate, or by using UV-, gamma- or electron beam-radiation.

Figure 10:
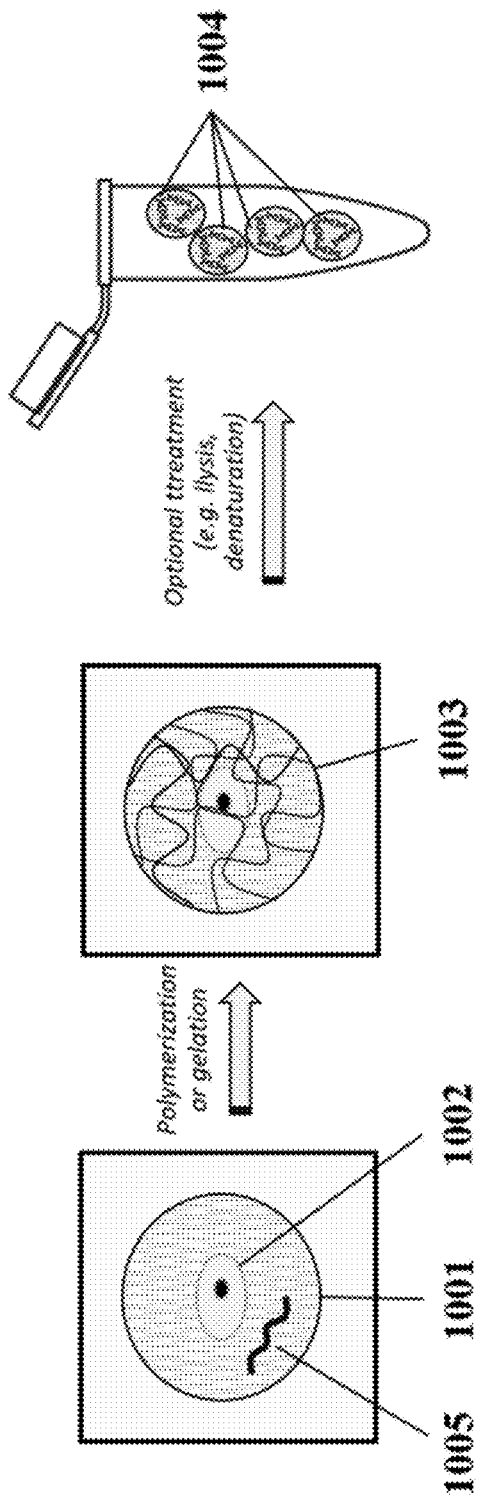
FIG. 10 illustrates a scheme for cell bead generation.

For example, as shown in FIG. 10, cells (or cell nuclei) and polymer or gel precursors are mixed with an immiscible fluid (e.g., an oil), thereby generating a plurality of aqueous droplets, including droplet 1001 comprising a biological particle, in this instance a cell 1002. Droplet 1001 may also comprise a nucleic acid molecule 1005 comprising a functional sequence, as described elsewhere herein. Droplet 1001 is subjected to conditions sufficient for polymerization or gelation of the polymer or gel precursors to generate a cell bead 1003 comprising cell 1002 (or a cell nucleus) and optionally nucleic acid molecule 1005. Gelation may comprise any of the gelation mechanisms and polymers described herein. In some instances, cell bead 1003 is subjected to treatment conditions sufficient to lyse cell 1002 or otherwise process the cell according to the epigenetic analyses disclosed elsewhere herein. In other embodiments, cell 1002 is lysed in droplet 1001 prior to polymerization or gelation of the polymer or gel precursors to generate cell bead 1003. In still other embodiments, cell 1002 is permeabilized before, during, or after polymerization or gelation of the polymer or gel precursors. Cell beads are collected to generate a plurality of cell beads 1004. Cell beads may be stored for further processing, such as the epigenetic analyses described elsewhere herein.

In some cases, where applicable, nucleic acid molecule 1005 may be attached to the cell beads subsequent to polymerization or gelation of the polymer or gel precursor. For instance, polymer or gel precursors may comprise one or more functional groups that facilitate the attachment of nucleic acid molecule 1005 subsequent to polymerization or gelation of the polymer or gel precursors. In other embodiments, the polymer or gel precursors and/or nucleic acid molecule 1005 comprise functional groups, which facilitate the incorporation of nucleic acid molecule 1005 into the cell bead during polymerization or gelation of the polymer or gel precursors. In some embodiments, the functionalized nucleic acid molecule(s) 1005 are entrapped within the cell bead polymeric and/or crosslinked matrix (also referred to herein as a "cell bead matrix"). In other embodiments, the nucleic acid molecule(s) 1005 are functionalized with chemical groups (e.g., acrydite, amine, thiol, etc.) such that the nucleic acid molecule(s) 1005 are incorporated into or otherwise attached to the cell bead matrix. For example, in a cell bead matrix comprising polyacrylamide, the nucleic acid molecule 1005 can comprise an acrydite moiety such that, upon polymerization of acrylamide monomers, the functionalized nucleic acid molecule(s) 1005 are incorporated into the cell bead matrix. In some embodiments, both the nucleic acid molecule 1005 and/or the cell bead matrix comprise one or more functional groups configured to facilitate attachment of the nucleic acid molecule 1005 to the cell bead matrix. For example, in some embodiments, generation of a cell bead comprising a nucleic acid molecule 1005 comprises: (a) providing a plurality of polymer or gel precursors (e.g., in a partition), wherein the polymer or gel precursors comprise a plurality of first crosslink precursors; (b) providing a plurality of functionalized nucleic acid molecules comprising a second crosslink precursor; and (c) crosslinking the polymer or gel precursors and the nucleic acid molecules via a reaction between a first section of the first crosslink precursors and a second section of the second crosslink precursors, thereby forming the cell bead comprising the nucleic acid molecule(s).

In some instances, the functionalized nucleic acid molecules are irreversibly incorporated into the cell bead matrix. In other instances, the functionalized nucleic acid molecules are reversibly incorporated into the cell bead matrix. For example, a functionalized nucleic acid molecule can be functionalized with a labile moiety as described elsewhere herein (e.g., a disulfide bond) such that the functionalized nucleic acid molecule, or a portion thereof, is configured to be released from the cell bead matrix and/or cell bead. In some embodiments, the nucleic acid molecule(s) described herein are attached, entrapped, or otherwise incorporated into the cell bead matrix during cell bead generation (see, e.g., FIG. 10 and FIG. 11). In other embodiments, the nucleic acid molecule(s) described herein are attached, entrapped, or otherwise incorporated into the cell bead matrix subsequent to cell bead generation. For example, in some instances, a cell bead can be generated as described elsewhere herein and a nucleic acid molecule can be attached to the cell bead matrix by a chemical reaction, e.g., between a functional group of the nucleic acid molecule(s) and a functional group in the cell bead matrix.

In some embodiments, the cell bead matrix includes one or more of the following; disulfide crosslinked polyacrylamide, agarose, alginate, polyvinyl alcohol, PEG-diacrylate, PEG-acrylate/thiol, PEG-azide/alkyne, other acrylates, chitosan, hyaluronic acid, collagen, fibrin, gelatin, elastin, a polyolefin, an olefin copolymers, an acrylics, a vinyl polymer, a polyesters, a polycarbonate, a polyamide, a polyimide, a formaldehyde resin, a polyurethane, an ether polymer, a cellulosic, a thermoplastic elastomer, a thermoplastic polyurethane, or any polymeric precursor (e.g., monomer) thereof. In some embodiments, the cell bead matrix comprises polyacrylamide (e.g., disulfide crosslinked polyacrylamide).

In some embodiments, generation of the cell bead matrix comprises (a) providing a first polymer or gel precursor, wherein the first polymer or gel precursor comprises a plurality of first crosslink precursors, for example a moiety comprising an azide group; (b) providing a second polymer or gel precursor, wherein the second polymer or gel precursor comprises a plurality of second crosslink precursors, for example a moiety comprising an alkyne group; and (c) crosslinking the first polymer and the second polymer via a reaction (e.g., a click-chemistry reaction) between a first section of the first crosslink precursors and a second section of the second crosslink precursors, thereby forming the cell bead.

Figure 11:
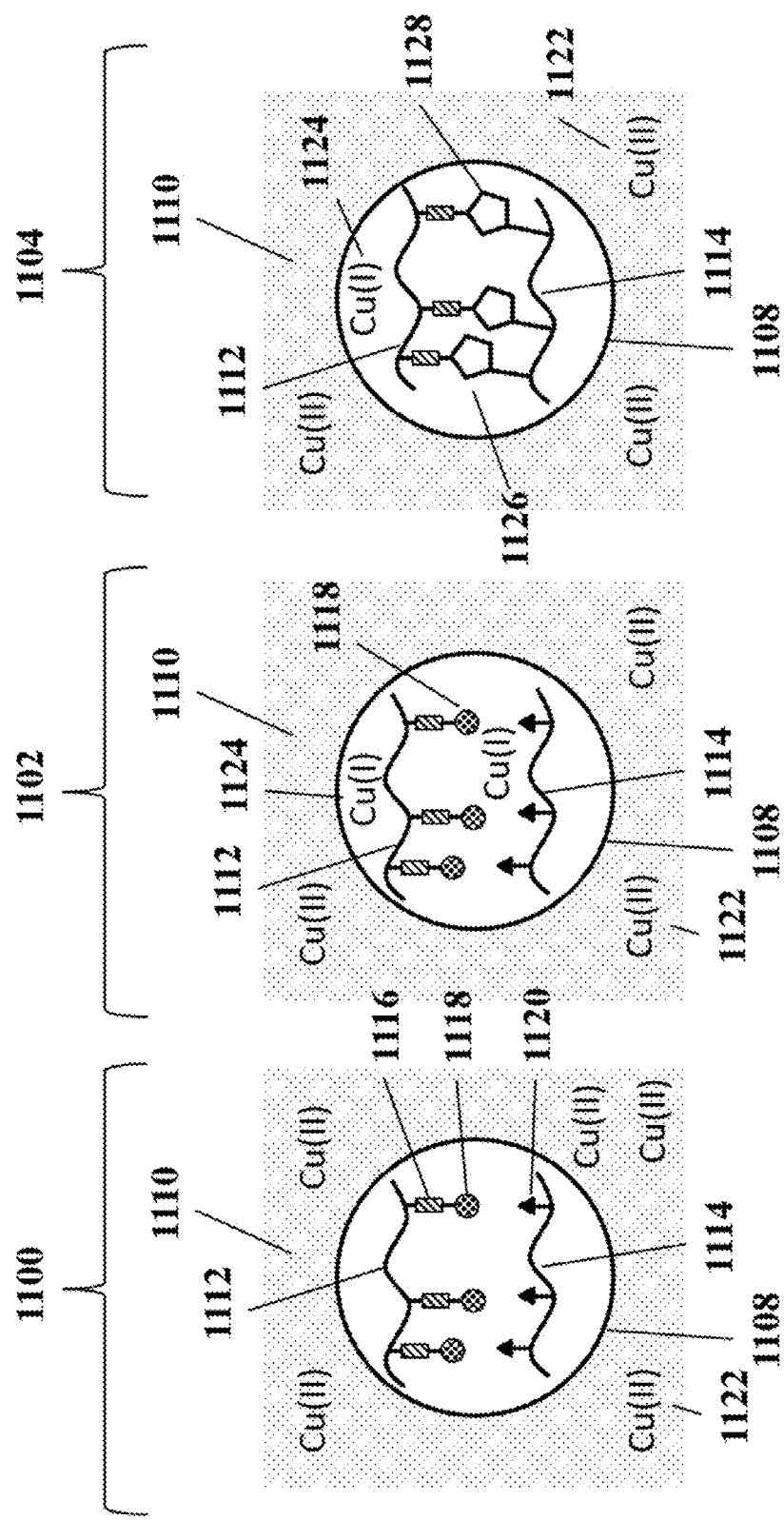
FIG. 11 illustrates a scheme for cell bead generation or functionalization using crosslinks.

For example, as shown in FIG. 11, systems 1100, 1102, and 1104 represent different stages through which polymer molecules or gel precursors are crosslinked to form a cell bead matrix or hydrogel. Emulsion system 1100 can comprise a discrete droplet 1108 (comprising an aqueous phase) immersed in an oil phase 1110. Within the discrete droplet 1108, two polymer molecules 1112 and 1114 and a biological particle (e.g., a single biological particle, such as a single cell or nucleus—not shown) can be partitioned together. In some instances, a nucleic acid molecule is also partitioned with the polymer molecules or gel precursors and the biological particle. In some embodiments, the nucleic acid molecule further comprises an attachment moiety (e.g., a click chemistry moiety such as 1118 or 1120) to facilitate attachment to the cell bead matrix. Polymer molecule 1112 can comprise a first crosslink precursor comprising a first click chemistry moiety 1118 and optionally a labile bond 1116 (e.g., a chemically, thermally, enzymatically, or photolabile bond). Polymer molecule 1114 can comprise a second click chemistry moiety 1120. In the oil phase 1111, there can be other reagents, such as reagent 1122 (shown as a copper (II) reagent), which may be utilized to facilitate the click chemistry reaction between the first click chemistry moiety 1118 and the second click chemistry moiety 1120, either by itself or by a derivative thereof. Because the reagent 1122 remains outside of the discrete droplet 1108, generally no click chemistry reaction happens within the discrete droplet 1108 in the absence of the reagent 1122.

In emulsion system 1102, some of the reagent 1122 can penetrate the discrete droplet 1108, via, e.g., physical or chemical processes. In some instances, reagent 1122 becomes or is otherwise processed to become reagent 1124 (shown as a copper (I) reagent) in the discrete droplet 1108. In some instances, conversion into reagent 1124 requires additional reagents (not shown, e.g., a reducing agent such as sodium ascorbate). In these embodiments, reagent 1124 can be the reagent required to initiate the click chemistry reaction between the first click chemistry moiety 1118 and the second click chemistry moiety 1120. Once in the proximity of both the first click chemistry moiety 1118 and the second click chemistry moiety 1120, the reagent 1124 can initiate a click chemistry reaction, such as a Cu(I)—Catalyzed Azide-Alkyne Cycloaddition (CuAAC), see emulsion system 1104. In embodiments where the functionalized nucleic acid molecules comprise a click-chemistry moiety, the reagent can also catalyze the attachment of nucleic acid molecules to the cell bead matrix.

As shown in the emulsion system 1104 of FIG. 11, in the presence of the reagent 1124, a crosslink 1126 is formed linking the two polymer molecules 1112 and 1114 together, via the newly formed moiety 1128 because of the click chemistry reaction between the first click chemistry moiety 1118 and the second click chemistry moiety 1120. A hydrogel comprising the crosslinked polymer molecules 1112 and 1114 can thus be formed, thereby generating the cell bead. Reagents 1122 and/or 1124 can be removed from the newly formed hydrogel if desired. In some instances, the cell bead matrix comprises a labile bond 1116 (e.g., a disulfide bond) configured to release the crosslinks 1126 and/or degrade the hydrogel upon application of a stimulus (e.g., a chemical, thermal, or photo-stimulus). In some instances, the nucleic acid molecules are attached to the hydrogel via a labile bond 1116 configured to release the nucleic acid molecules from the cell bead matrix.

A nucleic acid molecule (e.g., DNA or RNA molecule in or derived from a cell or nucleus) of a cell bead may comprise one or more epigenetic features. Non-limiting examples of epigenetic features include: methylation of the nucleic acid molecule, hydroxymethylation of the nucleic acid molecule, modification of histone proteins associated with the nucleic acid molecule, presence or abundance of DNA binding proteins, chromatin packaging associated with the nucleic acid molecule, and chromatin accessibility associated with the nucleic acid molecule. Epigenetic features may produce changes which alter gene expression without altering the underlying nucleic acid sequence and thus, may change an epigenetic state or characteristic of the nucleic acid molecule. For example, hypermethylation of DNA may repress gene expression, thus changing the epigenetic state of the DNA molecule from being active to inactive.

One or more epigenetic features can be assessed by subjecting a nucleic acid molecule in or derived from a cell or nucleus to a reaction in order to determine an epigenetic state or characteristic of the nucleic acid molecule. Non-limiting examples of such reactions include: nucleic acid amplification, bisulfite treatment, oxygenase treatment, enzymatic deamination, proteinase treatment, methyltransferase treatment, treatment with methylation-specific restriction enzyme, ligase treatment, template switching treatment, Micrococcal nuclease digestion, transposon insertion, crosslinking treatment, restriction digestion, and proximity ligation.

Figure 13:
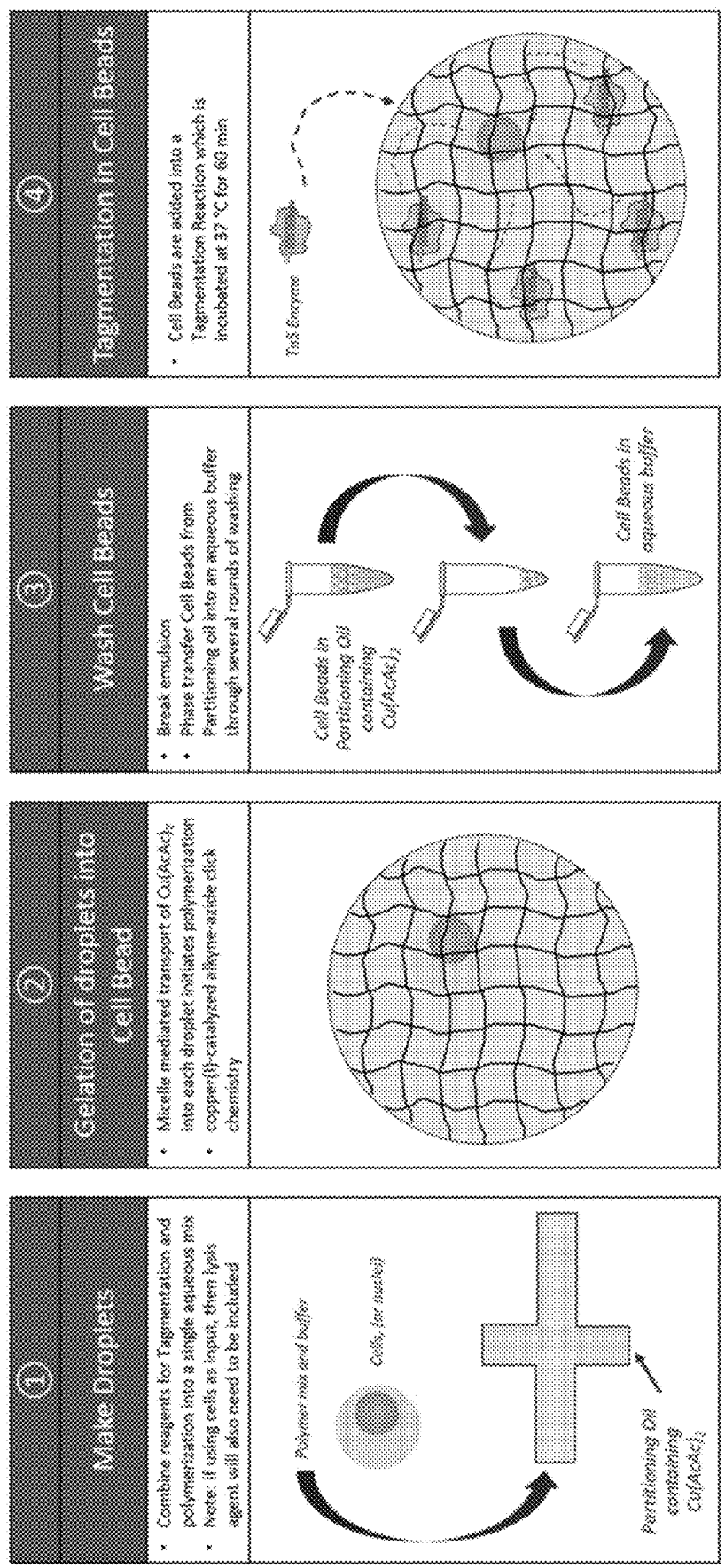
FIG. 13 illustrates a process in which biochemical reactions are performed on a cell or cell nucleus subsequent to cell bead gelation.

In some instances, one or more downstream biochemical reactions (such as the epigenetic analyses described herein) are performed after gelation of a cell bead. See, e.g., FIG. 13. For example, in some embodiments, cells (or nuclei) are encapsulated within partitions (e.g., aqueous droplets) comprising a mixture of polymers or polymer precursors and droplets are surrounded by a partitioning oil comprising a copper catalyst. Copper is micelle mediated transported from the partitioning oil into the aqueous environment of a droplet to initialize polymerization into cell beads which entrap cells (or nuclei) within a polymer matrix. Cell beads are then washed from partitioning oil into an appropriate aqueous buffer for downstream biochemical reactions, such as the epigenetic analyses described elsewhere herein.

Figure 14:
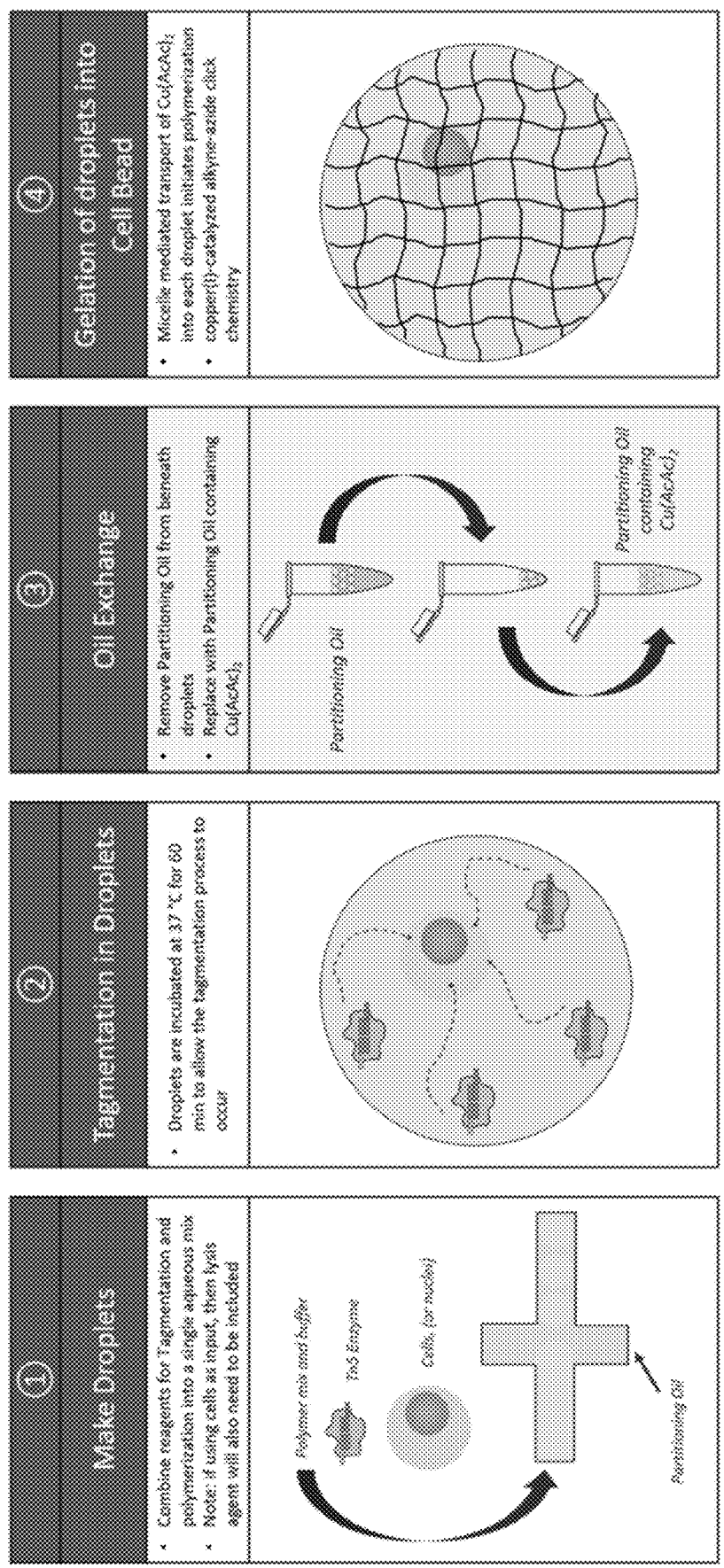
FIG. 14 illustrates a process in which biochemical reactions are performed on a cell or cell nucleus prior to cell bead gelation.

However, in some instances, during the copper-initiated gelation process, oxidative damage to nucleic acids can occurs, impacting downstream biochemical assays. Thus, in some instances, one or more downstream biochemical reactions (such as the epigenetic analyses described herein) are performed prior to gelation of a cell bead. See, e.g., FIG. 14. For example, in some embodiments, cells (or nuclei) are encapsulated within partitions (e.g., aqueous droplets) comprising a mixture of polymers or polymer precursors and droplets are surrounded by a partitioning oil that lacks a copper catalyst. Prior to gelation, one or more biochemical reactions, such as the epigenetic analyses described elsewhere herein, are performed on the cells. In some instances, the reagents for performing epigenetic analyses are co-partitioned with the cells (or nuclei) and polymers or polymer precursors. Subsequent to these biochemical reactions, partitioning oil comprising a copper catalyst can be added to the mixture or at the non-copper containing partitioning oil can be removed (or reduced) and replaced with partitioning oil comprising a copper catalyst. Copper is then micelle mediated transported from the partitioning oil into the aqueous environment of a droplet to initialize polymerization into cell beads.

In some examples, an epigenetic feature can be assessed by subjecting the nucleic acid molecule to deamination, such as, for example, cytosine deamination. In some cases, cytosine deamination may be effected by chemical treatment, such as bisulfite treatment. In some cases, cytosine deamination may be affected by an enzyme, such as cytidine deaminase. In some cases, a cytidine deaminase such as apolipoprotein B mRNA editing enzyme, catalytic polypeptide-like (APOBEC) can be used. Non-limiting examples of APOBEC family proteins include APOBEC1, APOBEC2, APOBEC3A, APOBEC3B, APOBEC3C, APOBEC3D, APOBEC3F, APOBEC3G, APOBEC3H, APOBEC4, and Activation-induced (cytidine) deaminase (AID). In some cases, methylation and hydroxymethylation of DNA may be distinguished by using the APOBEC3 cytidine-deaminase. In some cases, APOBEC-seq for DNA methylation may be used for assaying chromatin accessibility in a single cell. The cytosine deamination of the nucleic acid molecule can deaminate unmethylated cytosine to uracil while leaving 5-methylcytosine intact. The uracils are then amplified as thymines, whereas 5-methylcytosines are amplified as cytosines. Comparison of sequence information between the reference genome and bisulfite- or cytidine deaminase-treated DNA can provide information about an epigenetic state, cytosine methylation, of the DNA molecule.

In some examples, an epigenetic feature can be assessed by subjecting the nucleic acid molecule to a methylation-specific enzyme. For example, methylation-sensitive restriction enzymes that are sensitive to the DNA methylation states may be used. Such restriction enzymes cannot cleave methylated-cytosine residues, leaving methylated DNA intact. As the unmethylated DNA is cleaved by the methylation-sensitive restriction enzyme, the methylated DNA may further be sequenced in the sequencing assay. In this assay, methylated regions in the genome can be determined. In some cases, methylation-sensitive enzymes may be used in conjunction with an isoschizomer that has the same recognition site, but is methylation insensitive. In such an assay, the methylation status of the genome can be obtained by comparing sequence information obtained with the methylation-sensitive enzyme to that with the isoschizomer.

A nucleic acid molecule subjected to a method for assessing an epigenetic feature may be contacted with a nucleic acid barcode molecule (such as in a partition, such as a droplet of a droplet emulsion or well of a microwell array). As described elsewhere herein, the nucleic acid barcode molecule can be attached to a bead, such as a gel bead. The nucleic acid barcode molecule can be releasably attached or coupled to the bead. For example, the nucleic acid barcode molecule can be attached to the bead by a bond (e.g., a covalent bond) that can be broken by a stimulus (e.g., chemical stimulus), thereby releasing the nucleic acid barcode molecule. The nucleic acid barcode molecule may be coupled to the bead via a labile moiety (e.g., as described herein). In an example, the bead (e.g., gel bead) can be degraded or dissolved, which may affect the release of the nucleic acid barcode molecule from the bead. In another example, the nucleic acid barcode molecule may not be releasably attached or coupled to the bead. For example, the nucleic acid barcode molecule can be attached to the bead by bonds that are resistant to a stimulus (e.g., chemical stimulus).

A nucleic acid barcode molecule can comprise a barcode sequence. The barcode sequence can be a cell barcode sequence that is indicative of the cell from which the nucleic acid molecule originates. For example, a given barcode sequence (e.g., cell barcode sequence) may be unique to a given cell (e.g., a given cell bead comprising the given cell). This may be achieved by contacting a nucleic acid molecule of a cell (e.g., within a cell bead) with a unique cell barcode sequence (e.g., by co-partitioning the cell, such as a single cell, and the nucleic acid barcode molecule comprising the cell barcode sequence, such as a single bead comprising the barcode molecule). The nucleic acid barcode molecule can comprise one or more additional sequences. The additional sequences can be useful in downstream assays, such as a sequencing assay. The additional sequences can be selected based on the assay used. For example, the additional sequences can include a primer binding site, such as a sequencing primer site (e.g., R1 or R2 sequence or partial sequences thereof), a flow cell binding sequence (e.g., P5 or P7 sequence or partial sequences thereof), a targeted primer sequence, a random primer sequence, a unique molecular identifier sequence, or any other sequence. A primer binding site can comprise a sequence for a sequencing primer to hybridize to during a sequencing reaction and/or for a primer to hybridize to in an amplification and/or extension reaction. A sequence of a nucleic acid barcode molecule may be a functional sequence. A sequence of a nuclei acid barcode molecule may be, for example, a spacer sequence.

A nucleic acid barcode molecule can interact with a segment of the nucleic acid sequence of a nucleic acid molecule (e.g., a template nucleic acid molecule of or derived from a cell or cell nucleus) subjected to a treatment for assessing an epigenetic feature (e.g., as described herein) to generate a barcoded nucleic acid molecule. In some instances, template nucleic acid molecule is processed to attach one or more adapter sequences suitable for downstream processing steps, such as barcoding. In some cases, the nucleic acid barcode molecule can be attached to a segment of the nucleic acid sequence of the template molecule with the aid of one or more reagents, such as nucleic acid extension reagents or ligation reagents. For example, in some instances, the nucleic acid barcode molecule comprises a functional sequence configured to attach to a complementary segment of the template sequence (such as a template-specific sequence or an adapter sequence added to the template), which can then be processed in a ligation or nucleic acid extension reaction. The extension reaction (such as nucleic acid extension, amplification, and/or PCR) may comprise annealing the nucleic acid barcode molecule to a complementary segment of the template nucleic acid molecule, extending the nucleic acid barcode molecule (and/or the template) to generate a barcoded nucleic acid molecule). In some cases, the resultant barcoded nucleic acid molecule can be denatured. Generation of the barcoded nucleic acid molecule may comprise performing a nucleic acid ligation reaction. The ligation reaction may comprise annealing the nucleic acid barcode molecule to a complementary segment of the template nucleic acid molecule and ligating the nucleic acid barcode molecule to the template nucleic acid molecule to generate a barcoded nucleic acid molecule. Non-limiting examples of the reagents useful in the generation of a barcoded nucleic acid molecule and/or attachment of a nucleic acid barcode molecule to a nucleic acid molecule of interest can include ligases, DNA polymerases, nucleoside triphosphates, and buffers with cofactors (e.g. $Mg^{2+}$). The reagents can be co-partitioned with a biological particle (e.g., cell or cell bead) and/or with a nucleic acid barcode molecule (e.g., a nucleic acid barcode molecule coupled to a bead, such as a gel bead). The nucleic acid barcode molecule can be attached to the template nucleic acid molecule at either one or both ends of the molecule to yield a barcoded nucleic acid molecule.

The nucleic acid molecule subjected to a reaction for assessing an epigenetic feature may be subjected to barcoding and sequencing as described herein. Subjecting a nucleic acid molecule (e.g., a barcoded nucleic acid molecule) to a sequencing assay will provide a plurality of sequencing reads. Sequencing reads can be analyzed to detect one or more sequences included therein, such as a cell barcode sequence. A barcode sequence such as a cell barcode sequence can serve to identify a nucleic acid sequence (e.g., a DNA sequence) as being derived from a given cell, such as a given cell encapsulated in a cell bead (e.g., as described herein). Reads corresponding to a DNA sequence can provide one or more types of information, depending on the nature of a reaction or assay performed to affect an epigenetic feature of a nucleic acid molecule. For example, sequences obtained from DNA that underwent bisulfite treatment and/or enzymatic deamination can be used to obtain methylation information, for example, by using sequencing reads corresponding to unmethylated and methylated cytosine residues to identify regions of methylation in the DNA molecule. In another example, sequences obtained from DNA that underwent methyltransferase treatment can be used to obtain chromatin accessibility information, for example, by using sequencing reads corresponding to methylated cytosine residues to identify regions of chromatin inaccessibility. In some cases, DNA may be subjected to bisulfite treatment prior to DNA sequencing to facilitate identification of methylated DNA residues. In other cases, DNA may be processed to detect 5-hydroxymethylation of cytosine (5hmC). For example, in some embodiments, genomic DNA may be glycosylated to protect 5hmC residues and then subjected to enzymatic oxidation and bisulfite treatment. DNA sequencing libraries can then be generated and sequenced as described herein to reveal hydroxymethylated bases. See, e.g., Yu M., et al., Base-Resolution Analysis of 5-Hydroxymethylcytosine in the Mammalian Genome, Cell. 2012 Jun. 8; 149(6):1368-80.

Figure 9:
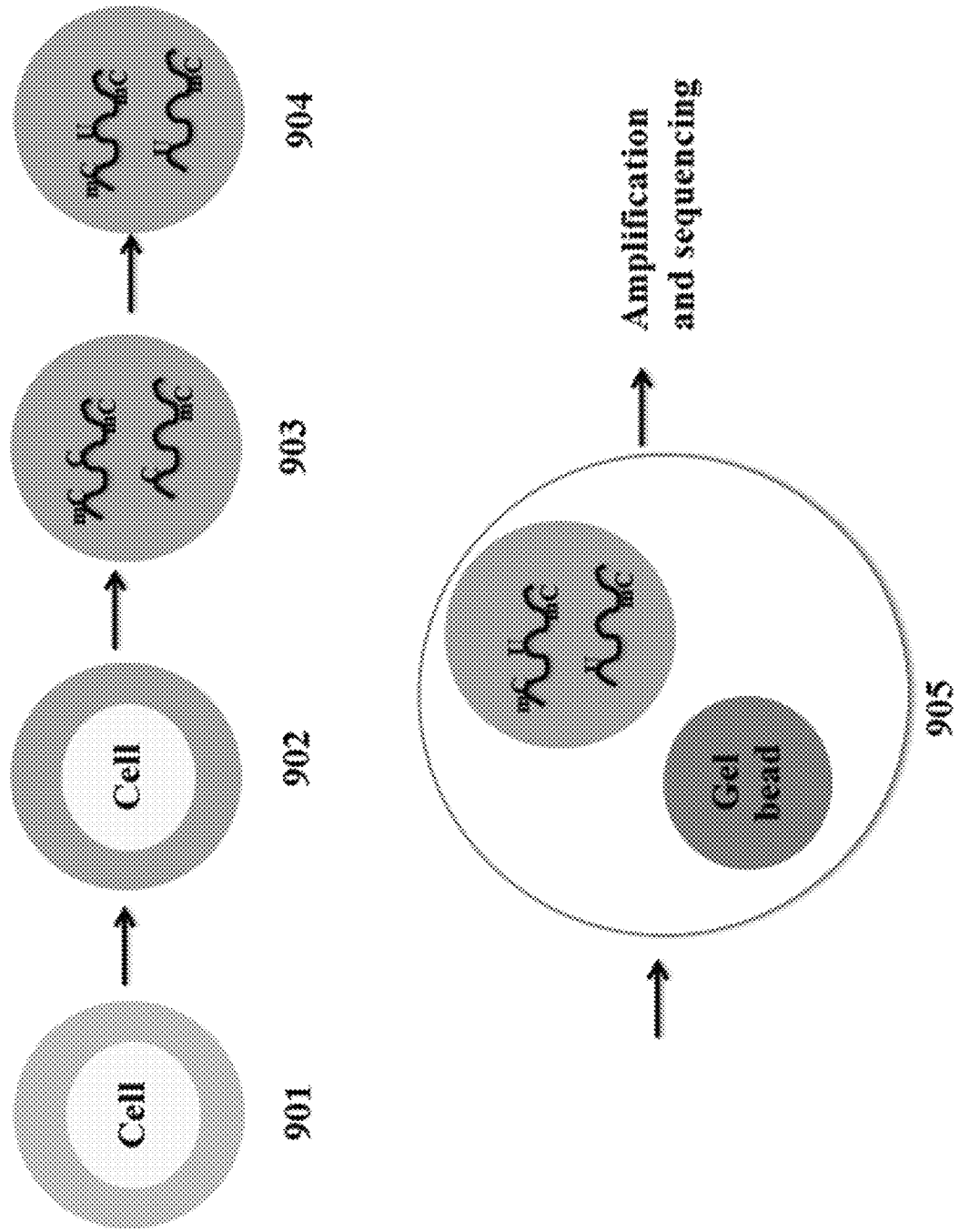
FIG. 9 illustrates an example of a method for epigenetic characterization of nucleic acid molecules from a cell.

An example of a method for epigenetic characterization of nucleic acid molecules from a single cell is illustrated in FIG. 9. A single cell can be encapsulated (e.g., in a droplet) in a mixture of polymer(s) and/or polymer precursor(s) as shown in 901. The mixture of polymer(s) and/or polymer precursor(s) may be allowed to polymerize or otherwise crosslink to yield a cell bead as shown in 902. A shown in 903, the cell in the cell bead may be lysed to release contents (e.g., nucleic acid molecules) of the cell. The contents of the lysed cell may be treated with one or more proteases (e.g., Proteinase K). The epigenetic features of the nucleic acid contents of the lysed cell may be assessed by a reaction, such as bisulfite treatment, as shown in 904. As shown in 905, the bisulfite-treated cell bead can be co-partitioned (e.g., in a droplet) with a barcode bead (e.g., gel bead). As described elsewhere herein, the nucleic acid barcode molecule can be attached (e.g., releasably attached or coupled) to the barcode bead. A nucleic acid molecule of the cell (e.g., bisulfite treated DNA) and the nucleic acid barcode molecule can be used to generate a barcoded nucleic acid molecule (e.g., via a nucleic acid extension or ligation reaction). The barcoded nucleic acid molecule can be sequenced and analyzed in order to determine an epigenetic state of the nucleic acid molecule. For example, subjecting the nucleic acid molecule to the bisulfite treatment, as in 904, can deaminate unmethylated cytosines to generate uracils while leaving 5-methylcytosines intact. The uracils may then be amplified as thymines, whereas 5-methylcytosines are amplified as cytosines. Comparison of sequence information between the reference genome and bisulfite-treated DNA can provide information about epigenetic state (in this case cytosine methylation) of the DNA molecule.

Methods for Assessing Chromatin Accessibility

The methods of the present disclosure may be used for determining one or more epigenetic states or characteristics, such as chromatin accessibility, of a nucleic acid molecule from a biological particle, such as a cell. The methods provided herein may facilitate such analysis on a single cell level. Chromatin accessibility can be assessed by subjecting a native chromatin from a biological particle to an enzymatic (e.g., transposase) or non-enzymatic treatment (e.g., formaldehyde). For example, treatment of chromatin with deoxyribonuclease I (e.g., DNase-seq) or a transposase (e.g., ATAC-seq) can preferentially cleave DNA in an "open" or "accessible" chromatin, releasing a segment of nucleic acid molecules between two nucleosomes and/or occupied by DNA-binding proteins. In some instances, micrococcal nuclease (e.g., MNase-seq) cleavage can be utilized to preferentially enrich DNA in a "closed" conformation or DNA occupied by nucleosomes and other regulatory factors. For methods and systems describing single-cell DNase and MNase analysis that may be used according to the present disclosure, see e.g., U.S. Patent Publication No. 2019-0127731, which is hereby incorporated by reference in its entirety. For a description of ATAC-seq and ATAC-seq compositions, systems, and methodologies, see, e.g., U.S. Pat. No. 10,059,989 and U.S. Patent Publication No. 2018-0340171, both of which are hereby incorporated by reference in their entireties.

A biological particle can be a single biological particle, such as a cell, cell nucleus, or a polymer matrix comprising a cell, a cell nucleus, and/or components of a cell (e.g., cell bead) as disclosed elsewhere herein. A biological particle can be a plurality of biological particles, such as a plurality of cells or cell nuclei. A biological particle can comprise a live or fixed cell, such as a formalin-fixed paraffin-embedded (FFPE) cell. A biological particle can comprise any cellular component or derivative or combination thereof, such as a nucleic acid molecule (e.g., deoxyribonucleic acid (DNA) or ribonucleic acid (RNA), nucleus, etc. A biological particle can be encapsulated or entrapped in a gel matrix to preserve the biological particle. The biological particle can be encapsulated prior to or subsequent to partitioning into the biological particle into a partition (e.g., a droplet or well).

A biological particle can comprise chromatin. Chromatin can be released from a biological particle prior to or subsequent to partitioning the biological particle within a partition (e.g., a droplet or well). Chromatin may be released from a biological particle by, for example, treatment with one or more reagents. For example, the biological particle can be treated with a lysis reagent to release chromatin. The chromatin can comprise one or more nucleic acid molecules wrapped around nucleosomes (e.g., regularly spaced protein complexes). Each nucleosome can comprise, for example, a histone octamer core wrapped around by a nucleosome-associated nucleic acid molecule of length ~147 base pairs (bp). The nucleosomes can be separated by a nucleic acid molecule or a linker DNA. Two nucleosomes can be separated by a segment of nucleic acid molecule having a nucleic acid sequence.

The chromatin can be packaged tightly or loosely based on nucleosome occupancy of the chromatin. For example, chromatin with greater nucleosome occupancy can have a tightly packaged chromatin. Chromatin with a nucleosome depleted region (NDR) or with lower nucleosome occupancy can have a loosely packaged chromatin. The nucleosome occupancy can be correlated with chromatin accessibility. Tightly packaged chromatin can have lower chromatin accessibility; such chromatin can be considered to be in a "closed" configuration. Loosely packaged chromatin can have higher chromatin accessibility; such chromatin can be considered to be in an "open" chromatin configuration. Chromatin in an open configuration can be accessible to various moieties such as DNA-binding factors, DNA endonucleases, transposons, etc.

Chromatin accessibility can be assessed by subjecting a native chromatin from the biological particles to an enzymatic treatment. For example, deoxyribonuclease I (DNase I) can preferentially cleave DNA in an "open" or "accessible" chromatin, releasing a segment of nucleic acid molecules between two nucleosomes. DNase I hypersensitive sites (DHSs) can be generally correlated with an open chromatin configuration. DHSs can be indicative of regulatory DNA, such as promoters, enhancers, insulators, silencers, and locus control regions. Another deoxyribonuclease, Micrococcal nuclease (MNase), can fragment between two nucleosomes, thereby releasing a nucleosome-associated nucleic acid molecule. The nucleosome-associated nucleic acid molecule can generally be associated with a "closed" chromatin configuration.

Enzymatic treatment with DNase molecules or functional variants thereof can catalyze a hydrolytic cleavage of a phosphodiester linkage in a nucleic acid backbone. DNase molecules can catalyze the cleavage of a nucleic acid molecule in a substantially sequence-independent manner (e.g., DNase I) or in a substantially sequence-dependent manner (e.g., cleavage preference of MNase at AT sites). DNase molecules can cleave single-stranded and/or double-stranded nucleic acid molecules. DNase molecules can be endo- and/or exonuclease enzymes. The enzymatic treatment may be controlled using various reaction parameters. For example, the reaction parameters can include a concentration of enzyme and/or duration of treatment. The reaction parameters (e.g., concentration of enzyme) can be determined by using a titration assay. In some examples, DNA in chromatin can be completely digested. For example, DNA can be completely digested when subjected to MNase molecules to ensure fragmentation of DNA segments between nucleosomes. In some examples, DNA can be partially or lightly digested when subjected to the DNase I molecules. DNase molecules can be contained within a bead and/or attached to a bead or to nucleic acid barcode molecules. DNase molecules can be included with a biological particle. For example, DNase molecules can be included within a cell bead. Alternatively or in addition, DNase molecules can be included in a partition (e.g., droplet or well) with a biological particle (e.g., contained within the same fluid). DNase molecules can be provided with reagents, such as lysis reagents.

Chromatin accessibility can be assessed by subjecting a native chromatin from the biological particles to a transposition reaction (e.g., ATAC-seq usingTn5). Similar to DNase I, a transposase can be used to determine "open" or "accessible" chromatin. For example, a transposase can catalyze the movement of a transposon by cleaving DNA in an open chromatin region (or nucleosome depleted region) and ligating the transposon to the ends of the DNA molecule, thereby producing transposon-ligated DNA. The transposon may comprise specific sequences, such as adapter sequences.

Chromatin accessibility can be assessed by subjecting a native chromatin from the biological particles to methyltransferase treatment. This may comprise adding a methyl group to cytosine residues in the accessible or open parts of the chromatin. DNA that has undergone methyltransferase treatment may be subsequently sequenced to obtain sequencing reads corresponding to methylated cytosine residues to identify regions of chromatin inaccessibility, for example, by conducting methylation analysis via deamination of unmethylated cytosine nucleotides. This analysis may rely on the property of methylated cytosine nucleotides' resistance to deamination. In some cases, chromatin proteins may be digested by a proteinase (such as protein K) or a lytic enzyme (such as a lysozyme, cellulose, or zymolase) prior to the methylation analysis. In some cases, DNA may be denatured by alkaline denaturation (such as treatment with NaOH solution) prior to a methylation analysis.

Chromatin accessibility can be assessed by subjecting a native chromatin from the biological particles to non-enzymatic methods, such as by using formaldehyde for cross-linking nucleic acid molecules with the associated proteins.

The nucleic acid molecules treated with any of the methods for assessing chromatin accessibility (e.g., DNase, MNase, ATAC-seq, or ChIP-seq) can come in contact with a nucleic acid barcode molecule. As described elsewhere herein, the nucleic acid barcode molecule can be attached to a bead, such as a gel bead. The nucleic acid barcode molecule can be releasably attached or coupled to the bead. For example, the nucleic acid barcode molecule can be attached the bead by bonds that can be broken by a stimulus (e.g., chemical, thermal, or photo stimulus), thereby releasing the nucleic acid barcode molecule. The nucleic acid barcode molecule may be coupled to the bead via a labile moiety (e.g., as described herein). In an example, the bead (e.g., gel bead) can be degraded or dissolved, which may affect the release of the nucleic acid barcode molecule from the bead. In another example, the nucleic acid barcode molecule may not be releasably attached or coupled to the bead. For example, the nucleic acid barcode molecule can be attached to the bead by bonds that are resistant to a stimulus (e.g., chemical stimulus).

A nucleic acid barcode molecule can comprise a barcode sequence. The barcode sequence can be a cell barcode sequence that is indicative of the cell from which the nucleic acid molecule originates. For example, a given barcode sequence (e.g., cell barcode sequence) may be unique to a given cell (e.g., a given cell bead comprising the given cell). This may be achieved by contacting a nucleic acid molecule of a cell (e.g., within a cell bead) with a unique cell barcode sequence (e.g., by co-partitioning the cell and the nucleic acid barcode molecule comprising the cell barcode sequence). The nucleic acid barcode molecule can comprise additional sequences. The additional sequences can be useful in downstream assays, such as a sequencing assay. The additional sequences can be selected based on the assay used. For example, the additional sequences can include a primer binding site, such as a sequencing primer site (e.g., R1 or R2 sequence, or partial sequences thereof), flow cell binding sequences (e.g., P5 or P7 sequence or partial sequences thereof), a targeted primer sequence, a random primer sequence, a unique molecular identifier sequence, or any other sequence. A primer binding site can comprise a sequence for a sequencing primer to hybridize to during a sequencing or nucleic acid extension reaction and/or for a primer to hybridize to in an amplification and/or extension reaction. A sequence of a nucleic acid barcode molecule may be a functional sequence. A sequence of a nuclei acid barcode molecule may be, for example, a spacer sequence.

A nucleic acid barcode molecule can interact with a segment of the nucleic acid sequence of a nucleic acid molecule released upon subjection to a treatment for assessing chromatin accessibility (e.g., as described herein) to generate a barcoded nucleic acid molecule. In some cases, the nucleic acid barcode molecule can be attached to the segment of nucleic acid sequence of the nucleic acid molecule with the aid of one or more reagents, such as polymerization reagents or ligation reagents. For example, the nucleic acid barcode molecule can be attached to the segment of the nucleic acid sequence in a polymerization reaction. The polymerization reaction can comprise annealing the nucleic acid barcode molecule to the segment of the nucleic acid sequence of the nucleic acid molecule, extending the nucleic acid barcode molecule to generate a sequence complementary to a sequence of the nucleic acid molecule and, in some cases, denaturing the resultant double-stranded nucleic acid molecule to provide the barcoded nucleic acid molecule. Generation of the barcoded nucleic acid molecule may comprise performing a nucleic acid amplification reaction. For example, an amplification reaction may be used to generate a molecule comprising a sequence of the nucleic acid molecule and a sequence complementary to a cell barcode sequence. Non-limiting examples of the reagents useful in the generation of a barcoded nucleic acid molecule and/or attachment of a nucleic acid barcode molecule to a nucleic acid molecule of interest can include DNA polymerases, nucleoside triphosphates, and buffers with co-factors (e.g. $Mg^{2+}$). The reagents can be co-partitioned with a biological particle (e.g., cell or cell bead) and/or with a nucleic acid barcode molecule (e.g., a nucleic acid barcode molecule coupled to a bead, such as a gel bead). The nucleic acid barcode molecule can be attached to the segment of nucleic acid sequence of the nucleic acid molecule at either one or both ends of the segment to yield a barcoded nucleic acid molecule.

In some examples, DNase molecules may be co-partitioned with a single bead (e.g., gel bead) and a single biological particle (e.g., cell bead) in an individual partition (e.g., droplet or well). In other embodiments, a cell (such as a cell in a cell bead) is subjected to DNase treatment prior to co-partitioning a single bead (e.g., gel bead) and a single biological particle (e.g., cell bead) in an individual partition (e.g., droplet or well). The single bead may be releasably attached to a nucleic acid barcode molecule comprising a barcode sequence (e.g., cell barcode sequence). The single biological particle may include a nucleic acid molecule associated with nucleosomes in a chromatin. Occupancy of the nucleosomes in the chromatin may be inversely correlated with accessibility of the chromatin to the DNase molecules. Chromatin with lower nucleosome occupancy may be highly accessible or may be in an "open" configuration. The nucleic acid molecule associated with the open chromatin configuration may include DNase hypersensitive sites (DHS). The DNase molecules may fragment a nucleic acid molecule in the DHS, releasing a segment between the nucleosomes. The segment of the nucleic acid molecule may then be barcoded with the nucleic acid barcode molecule (e.g., subsequent to release of the nucleic acid barcode molecule from the bead) to yield a barcoded nucleic acid molecule (e.g., as described herein). In some cases, the barcoded nucleic acid molecule may be further processed within the individual partition, external to the individual partition, or both. For example, one or more additional sequences (e.g., functional sequences relevant to sequencing, such as sequencing primers, flow cell binding sequences, etc.) may be added to the barcoded nucleic acid molecule (e.g., via a ligation or extension reaction) to provide a derivative of the barcoded nucleic acid molecule. A barcoded nucleic acid molecule or derivative thereof may also be subjected to nucleic acid amplification. The barcoded nucleic acid molecule or derivative thereof (e.g., barcoded nucleic acid molecule comprising a flow cell sequence) may be subsequently sequenced to yield sequencing reads. The sequencing reads may permit mapping of the DHS and DNA footprints on a reference sequence. For example, the DHSs can be determined by assessing coverage of the sequencing reads across the reference genome. The DHSs can include sequences represented by a greater coverage of the sequencing reads. Sequences represented by a lesser coverage of the sequencing reads can be DNase-resistant sites. The DNA footprints can be determined within the DHSs as sites with atypical cleavage patterns, such as lack of cleavage. For example, a DNA footprint can include a sequence within the DHSs that may be represented by a lesser coverage of the sequencing reads, instead of a greater coverage. In some cases, the lesser coverage of the sequencing reads may be due to protein-bound regions, such as transcription factors bound to DNA, protecting DNA from DNase cleavage.

In some examples, MNase molecules may be co-partitioned with a single bead (e.gg., gel bead) and a single biological particle (e.g., cell bead) in an individual partition (e.g., droplet or well). In other embodiments, a cell (such as a cell in a cell bead) is subjected to MNase treatment prior to co-partitioning a single bead (e.g., gel bead) and a single biological particle (e.g., cell bead) in an individual partition (e.g., droplet or well). In some cases, a cross-linking agent (e.g., formaldehyde) may be co-partitioned with the MNase molecules, bead, and biological particle. The cross-linking agent may capture in vivo protein-nucleic acid and protein-protein interactions. This may prevent changes in nucleosome organization during chromatin preparation steps. The single bead (e.g., gel bead) may be releasably attached to a nucleic acid barcode molecule comprising a barcode sequence (e.g., cell barcode sequence). The single biological particle (e.g., cell bead) may include a nucleic acid molecule associated with nucleosomes in a chromatin. Occupancy of the nucleosomes in the chromatin may be directly correlated with accessibility of the chromatin to the MNase molecules. The chromatin with higher nucleosome occupancy may not be accessible or may be in a "closed" configuration. The nucleic acid molecule associated with the closed chromatin configuration may be associated with nucleosomes and other regulatory factors (e.g., transcription factors). The MNase molecules may fragment a nucleic acid molecule in the open configuration, releasing a segment associated with the nucleosomes. The segment of the nucleic acid molecule may then be barcoded with the nucleic acid barcode molecule to yield a barcoded nucleic acid molecule (e.g., subsequent to release of the nucleic acid barcode molecule from the bead). In some cases, the barcoded nucleic acid molecule may be further processed within the individual partition, external to the individual partition, or both. For example, one or more additional sequences (e.g., functional sequences relevant to sequencing, such as sequencing primers, flow cell binding sequences, etc.) may be added to the barcoded nucleic acid molecule (e.g., via a ligation or extension reaction) to provide a derivative of the barcoded nucleic acid molecule. A barcoded nucleic acid molecule or derivative thereof may also be subjected to nucleic acid amplification. The barcoded nucleic acid molecule or derivative thereof (e.g., barcoded nucleic acid molecule comprising a flow cell sequence) may be subsequently sequenced to yield sequencing reads. The sequencing reads may permit mapping of the nucleosome occupancy on a reference sequence.

In some examples, transposase-nucleic acid complexes, which comprise transposase molecules along with transposon end sequence containing nucleic acid molecules, may be co-partitioned with a single bead (e.g., gel bead) and a single biological particle (e.g., cell bead) in an individual partition (e.g., droplet or well). In other cases, transposase molecules and transposon end sequence containing nucleic acid molecules are co-partitioned with a single bead (e.g., gel bead) and a single biological particle (e.g., cell bead) in an individual partition (e.g., droplet or well) and subjected to conditions sufficient to form transposase-nucleic acid complexes in the partition. In other embodiments, a cell or nucleus (such as a cell or nucleus in a cell bead) is subjected to treatment with a transposase-nucleic acid complex prior to co-partitioning a single bead (e.g., gel bead) and a single biological particle (e.g., cell bead) in an individual partition (e.g., droplet or well). The nucleic acid molecules in a transposase-nucleic acid complex may comprise one or more adapter sequences, wherein the transposase-nucleic acid complex is configured to fragment and tag chromatin to generate adapter-flanked nucleic acid molecules representative of regions of open chromatin. For a description of ATAC-seq and ATAC-seq compositions, systems, and methodologies, see, e.g., U.S. Pat. No. 10,059,989 and U.S. Patent Publication No. 2018-0340171, both of which are incorporated by reference in their entireties. The single bead may be releasably attached to a nucleic acid barcode molecule comprising a barcode sequence (e.g., cell barcode sequence). The single biological particle may include a nucleic acid molecule associated with nucleosomes in a chromatin. Occupancy of the nucleosomes in the chromatin may be inversely correlated with accessibility of the chromatin to the transposase molecules. The chromatin with lower nucleosome occupancy may be highly accessible or may be in an "open" configuration. The transposon may comprise the nucleic acid barcode molecule such that this process yields a barcoded nucleic acid molecule. In some cases, the adapter-flanked nucleic acid molecules generated by the transposase are barcoded in a partition to generate a barcoded nucleic acid molecule. In some cases, the barcoded nucleic acid molecule may be further processed within the individual partition, external to the individual partition, or both. For example, one or more additional sequences (e.g., functional sequences relevant to sequencing, such as sequencing primers, flow cell binding sequences, etc.) may be added to the barcoded nucleic acid molecule (e.g., via a ligation or extension reaction) to provide a derivative of the barcoded nucleic acid molecule. A barcoded nucleic acid molecule or derivative thereof may also be subjected to nucleic acid amplification. The barcoded nucleic acid molecule or derivative thereof (e.g., barcoded nucleic acid molecule comprising a flow cell sequence) may be subsequently sequenced to yield sequencing reads. The sequencing reads may permit mapping of regions of open chromatin, nucleosome periodicity, DNA-binding protein occupancy, etc. Sequences represented by a lesser coverage of the sequencing reads can be due to DNA binding protein-bound regions, such as transcription factors bound to DNA, protecting DNA from the transposase activity.

In some examples, formaldehyde molecules may be utilized to crosslink chromatin to capture in vivo protein-DNA interactions. The crosslinked chromatin may be sheared, with sonication, for example, releasing crosslinked protein-bound DNA. In some instances, a segment between the nucleosomes is released due to higher crosslinking efficiency of histones to DNA, compared to other regulatory factors. Optionally, nucleic acid segments associated with specific DNA-binding or other proteins may be captured through immunoprecipitation (ChIP). The segment of the nucleic acid molecule bound by the DNA binding protein may then be optionally processed (e.g., to remove crosslinks and/or bound protein) and barcoded with the nucleic acid barcode molecule to yield a barcoded nucleic acid molecule (e.g., subsequent to release of the nucleic acid barcode molecule from the bead). In some cases, the barcoded nucleic acid molecule may be further processed within the individual partition, external to the individual partition, or both. For example, one or more additional sequences (e.g., functional sequences relevant to sequencing, such as sequencing primers, flow cell binding sequences, etc.) may be added to the barcoded nucleic acid molecule (e.g., via a ligation or extension reaction) to provide a derivative of the barcoded nucleic acid molecule. A barcoded nucleic acid molecule or derivative thereof may also be subjected to nucleic acid amplification. The barcoded nucleic acid molecule or derivative thereof (e.g., barcoded nucleic acid molecule comprising a flow cell sequence) may be subsequently sequenced to yield sequencing reads. The sequencing reads may permit identification of the sequences bound by DNA-binding proteins.

Reactions to generate a barcoded nucleic acid molecule (e.g., as described herein) can occur within a partition (e.g., droplet or well). The partition can be any container or a vessel, such as a well, microwell of a microwell array, tube, nanoarrays or other containers. The partition can be flowable within fluid streams, such as a microcapsule having an inner fluid core surrounded by an outer barrier. The partition can be a droplet of aqueous fluid within a non-aqueous phase, such as an oil phase. The partitioning can be performed by any of the methods disclosed herein.

Kits

The present disclosure also provides kits for characterizing nucleic acid molecules. The kits can include partitioning fluids, such as first liquid phase and second liquid phase, for generating partitions (e.g., droplets) with the microfluidic device as described elsewhere herein. The kits can include one, two, there, four, five, or more fluids as may be required by the microfluidic device. The fluids can comprise liquid phases, such as an aqueous phase. A given fluid can include a phase (e.g., oil phase) that is immiscible with at least one of the other liquids. At least one of the fluids can comprise reagents for assessing one or more epigenetic features of the nucleic acid molecules (e.g., as described herein). For example, the at least one of the fluids can comprise DNase molecules for assessing chromatin accessibility. A fluid may also comprise beads (e.g., gel beads) that may comprise nucleic acid barcode molecules attached thereto (e.g., as described herein). A kit may also comprise polymers and/or polymer precursors for preparing cell beads comprising cells or components thereof (e.g., as described herein). One or more reagents for assessing an epigenetic state of a nucleic acid molecule can be included in a fluid that is separate from a fluid comprising beads or any other fluid. At least one of the fluids included in a kit can be immiscible with the aqueous phase to facilitate co-partitioning (e.g., into droplets) of one or more components (e.g., biological particles, beads, and/or reagents) for a subsequent analysis such as chromatin accessibility treatment.

The kits can also comprise reagents, such as lysis reagents, for disrupting biological particles or components thereof to provide access to nucleic acid molecules therein, extending or amplifying nucleic acid molecules, and hybridizing or ligating various nucleic acid sequences. A kit may also comprise instructions for performing any of the foregoing methods described herein.

Systems

The present disclosure also provides systems for determining an epigenetic state or characteristic of a nucleic acid molecule from a single cell. A system may comprise a first controller programmed to direct partitioning of a biological particle comprising a nucleic acid molecule and a nucleic acid barcode molecule comprising a barcode sequence (e.g., cell barcode sequence) in a single partition (e.g., droplet or well) among a plurality of partitions. The first controller may also be programmed to, within the partition, direct synthesis of a barcoded nucleic acid molecule using the nucleic acid molecule and the nucleic acid barcode molecule. The barcoded nucleic acid molecule may comprise the barcode sequence. The nucleic acid molecule may contain or be suspected of containing one or more epigenetic features. The system may also comprise a second controller programmed to process the barcoded nucleic acid molecule or a derivative thereof to identify the one or more epigenetic features and the barcode sequence. In some cases, the system may comprise a single controller configured to carry out the functions of the first and second controllers (e.g., the first controller may be the second controller or vice versa). The system may further comprise a third controller programmed to use the one or more epigenetic features and the barcode sequence to determine that the epigenetic state or characteristic of the nucleic acid molecule are associated with the single cell.

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. The partition can be a droplet in an emulsion. A partition may comprise one or more other partitions.

A partition may include one or more particles. A partition may include one or more types of particles. For example, a partition of the present disclosure may comprise one or more biological particles and/or macromolecular constituents thereof. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be a biological particle and/or one or more of its macromolecular constituents encased inside of a gel or polymer matrix, such as via polymerization of a droplet containing the biological particle and precursors capable of being polymerized or gelled. Unique identifiers, such as barcodes, may be injected into the droplets previous to, subsequent to, or concurrently with droplet generation, such as via a microcapsule (e.g., bead), as described elsewhere herein. Microfluidic channel networks (e.g., on a chip) can be utilized to generate partitions as described herein. Alternative mechanisms may also be employed in the partitioning of individual biological particles, including porous membranes through which aqueous mixtures of cells are extruded into non-aqueous fluids.

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Publication No. 2010/0105112, which is entirely incorporated herein by reference for all purposes.

In the case of droplets in an emulsion, allocating individual particles to discrete partitions may in one non-limiting example be accomplished by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual biological particles. The channel structure 100 can include channel segments 102, 104, 106 and 108 communicating at a channel junction 110. In operation, a first aqueous fluid 112 that includes suspended biological particles (or cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual biological particle 114 (such as droplets 118). A discrete droplet generated may include more than one individual biological particle 114 (not shown in FIG. 1). A discrete droplet may contain no biological particle 114 (such as droplet 120). Each discrete partition may maintain separation of its own contents (e.g., individual biological particle 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., biological particles, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more biological particles 114, and (2) unoccupied droplets 120, not containing any biological particles 114. Occupied droplets 118 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 114) at the partitioning junction 110, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 2:
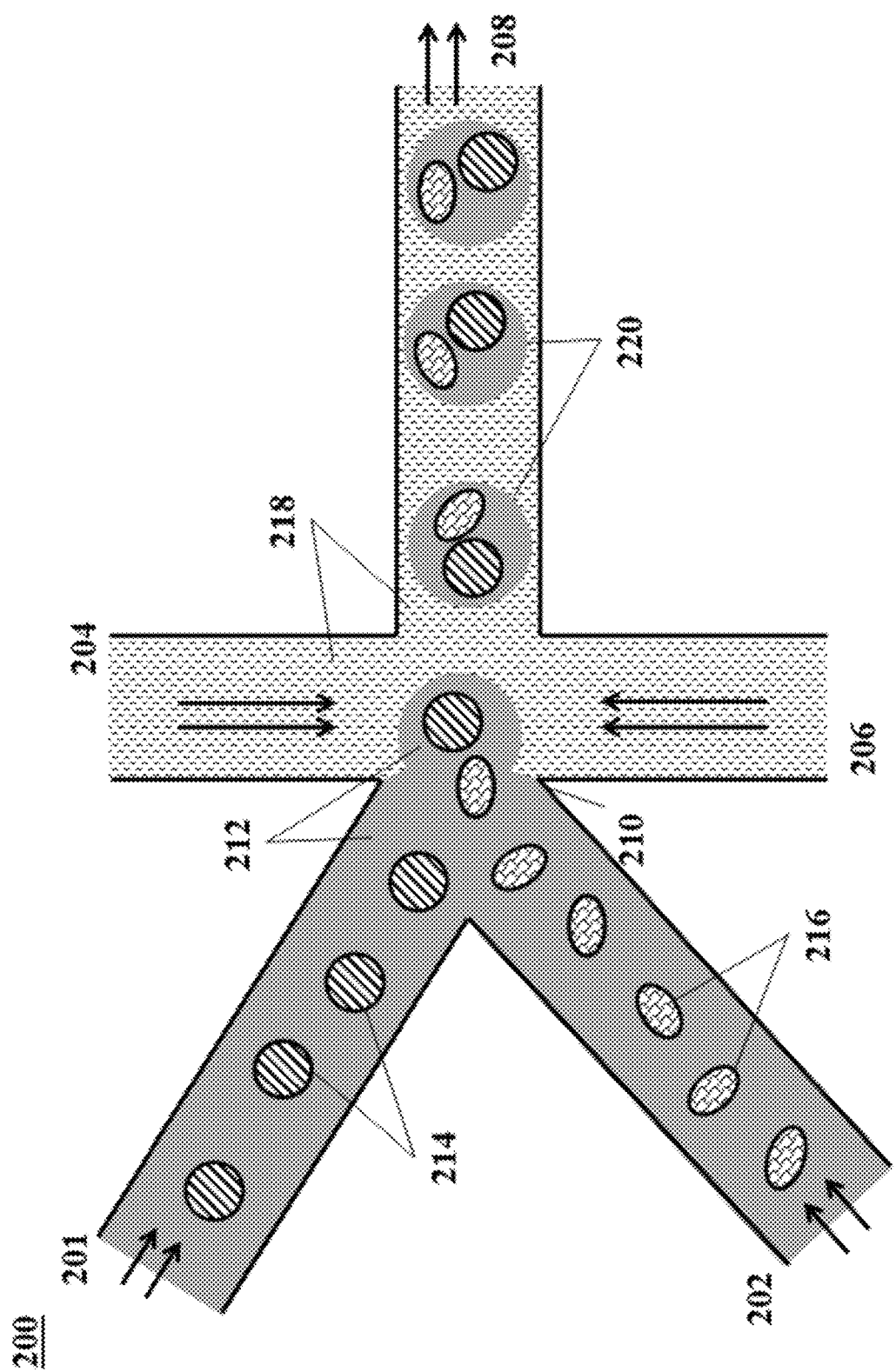
FIG. 2 shows an example of a microfluidic channel structure for delivering barcode carrying beads to droplets.

As will be appreciated, the above-described occupancy rates are also applicable to partitions that include both biological particles and additional reagents, including, but not limited to, microcapsules or beads (e.g., gel beads) carrying barcoded nucleic acid molecules (e.g., oligonucleotides) (described in relation to FIG. 2). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and a biological particle.

In another aspect, in addition to or as an alternative to droplet based partitioning, biological particles may be encapsulated within a microcapsule that comprises an outer shell, layer or porous matrix in which is entrained one or more individual biological particles or small groups of biological particles. The microcapsule may include other reagents. Encapsulation of biological particles may be performed by a variety of processes. Such processes may combine an aqueous fluid containing the biological particles with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through cross-linking, polymerization initiation of the precursor (e.g., through added initiators)), mechanical stimuli, or a combination thereof.

Preparation of microcapsules comprising biological particles may be performed by a variety of methods. For example, air knife droplet or aerosol generators may be used to dispense droplets of precursor fluids into gelling solutions in order to form microcapsules that include individual biological particles or small groups of biological particles. Likewise, membrane based encapsulation systems may be used to generate microcapsules comprising encapsulated biological particles as described herein. Microfluidic systems of the present disclosure, such as that shown in FIG. 1, may be readily used in encapsulating cells as described herein. In particular, and with reference to FIG. 1, the aqueous fluid 112 comprising (i) the biological particles 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained biological particles. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams 116 in channel segments 104 and 106, which can initiate the copolymerization of the acrylamide and BAC into a cross-linked polymer network, or hydrogel.

Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., $Ca^{2+}$ ions), can be used as an encapsulation process using the described processes. Likewise, agarose droplets may also be transformed into capsules through temperature based gelling (e.g., upon cooling, etc.).

In some cases, encapsulated biological particles can be selectively releasable from the microcapsule, such as through passage of time or upon application of a particular stimulus, that degrades the microcapsule sufficiently to allow the biological particles (e.g., cell), or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix.

See, for example, U.S. Patent Application Publication No. 2014/0378345, which is entirely incorporated herein by reference for all purposes.

The biological particle can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle may be surrounded by polyacrylamide strands linked together by disulfide bridges. In this manner, the biological particle may be encased inside of or comprise a gel or matrix (e.g., polymer matrix) to form a "cell bead."

A cell bead can contain biological particles (e.g., a cell) or macromolecular constituents (e.g., RNA, DNA, proteins, etc.) of biological particles. A cell bead may include a single cell or multiple cells, or a derivative of the single cell or multiple cells. For example after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles.

Encapsulated biological particles can provide certain potential advantages of being more storable and more portable than droplet-based partitioned biological particles. Furthermore, in some cases, it may be desirable to allow biological particles to incubate for a select period of time before analysis, such as in order to characterize changes in such biological particles over time, either in the presence or absence of different stimuli. In such cases, encapsulation may allow for longer incubation than partitioning in emulsion droplets, although in some cases, droplet partitioned biological particles may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the biological particles into which other reagents are co-partitioned. Alternatively or in addition, encapsulated biological particles may be readily deposited into other partitions (e.g., droplets) as described above.

Beads

A partition may comprise one or more unique identifiers, such as barcodes. Barcodes may be previously, subsequently or concurrently delivered to the partitions that hold the compartmentalized or partitioned biological particle. For example, barcodes may be injected into droplets previous to, subsequent to, or concurrently with droplet generation. The delivery of the barcodes to a particular partition allows for the later attribution of the characteristics of the individual biological particle to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can comprise a bead. Beads are described in further detail below.

In some cases, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus may disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

FIG. 2 shows an example of a microfluidic channel structure 200 for delivering barcode carrying beads to droplets. The channel structure 200 can include channel segments 201, 202, 204, 206 and 208 communicating at a channel junction 210. In operation, the channel segment 201 may transport an aqueous fluid 212 that includes a plurality of beads 214 (e.g., with nucleic acid molecules, oligonucleotides, molecular tags) along the channel segment 201 into junction 210. The plurality of beads 214 may be sourced from a suspension of beads. For example, the channel segment 201 may be connected to a reservoir comprising an aqueous suspension of beads 214. The channel segment 202 may transport the aqueous fluid 212 that includes a plurality of biological particles 216 along the channel segment 202 into junction 210. The plurality of biological particles 216 may be sourced from a suspension of biological particles. For example, the channel segment 202 may be connected to a reservoir comprising an aqueous suspension of biological particles 216. In some instances, the aqueous fluid 212 in either the first channel segment 201 or the second channel segment 202, or in both segments, can include one or more reagents, as further described below. A second fluid 218 that is immiscible with the aqueous fluid 212 (e.g., oil) can be delivered to the junction 210 from each of channel segments 204 and 206. Upon meeting of the aqueous fluid 212 from each of channel segments 201 and 202 and the second fluid 218 from each of channel segments 204 and 206 at the channel junction 210, the aqueous fluid 212 can be partitioned as discrete droplets 220 in the second fluid 218 and flow away from the junction 210 along channel segment 208. The channel segment 208 may deliver the discrete droplets to an outlet reservoir fluidly coupled to the channel segment 208, where they may be harvested.

As an alternative, the channel segments 201 and 202 may meet at another junction upstream of the junction 210. At such junction, beads and biological particles may form a mixture that is directed along another channel to the junction 210 to yield droplets 220. The mixture may provide the beads and biological particles in an alternating fashion, such that, for example, a droplet comprises a single bead and a single biological particle.

Beads, biological particles and droplets may flow along channels at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 218 can comprise an oil, such as a fluorinated oil, that includes a fluorosurfactant for stabilizing the resulting droplets, for example, inhibiting subsequent coalescence of the resulting droplets 220.

A discrete droplet that is generated may include an individual biological particle 216. A discrete droplet that is generated may include a barcode or other reagent carrying bead 214. A discrete droplet generated may include both an individual biological particle and a barcode carrying bead, such as droplets 220. In some instances, a discrete droplet may include more than one individual biological particle or no biological particle. In some instances, a discrete droplet may include more than one bead or no bead. A discrete droplet may be unoccupied (e.g., no beads, no biological particles).

Beneficially, a discrete droplet partitioning a biological particle and a barcode carrying bead may effectively allow the attribution of the barcode to macromolecular constituents of the biological particle within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 200 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer (μall), 5 μm, 10 μm, 20 μm, 30 μm, 40 μm, 50 μm, 60 μm, 70 μm, 80 μm, 90 μm, 100 μm, 250 μm, 500 μm, 1 mm, or greater. In some cases, a bead may have a diameter of less than about 10 nm, 100 nm, 500 nm, 1μm, 5 μm, 10 μm, 20 μm, 30 μm, 40 μm, 50 μm, 60 μm, 70 μm, 80 μm, 90 μm, 100 μm, 250 μm, 500 μm, 1 mm, or less. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide), which may include a priming sequence (e.g., a primer for amplifying target nucleic acids, random primer, primer sequence for messenger RNA) and/or one or more barcode sequences. The one more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, such as, for example, a P5 sequence for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence for attachment to a sequencing flow cell for Illumina sequencing. In some cases, the nucleic acid molecule can comprise a barcode sequence. In some cases, the primer can further comprise a unique molecular identifier (UMI). In some cases, the primer can comprise an R1 primer sequence for Illumina sequencing. In some cases, the primer can comprise an R2 primer sequence for Illumina sequencing. Examples of such nucleic acid molecules (e.g., oligonucleotides, polynucleotides, etc.) and uses thereof, as may be used with compositions, devices, methods and systems of the present disclosure, are provided in U.S. Patent Pub. Nos.

2014/0378345 and 2015/0376609, each of which is entirely incorporated herein by reference.

Figure 8:
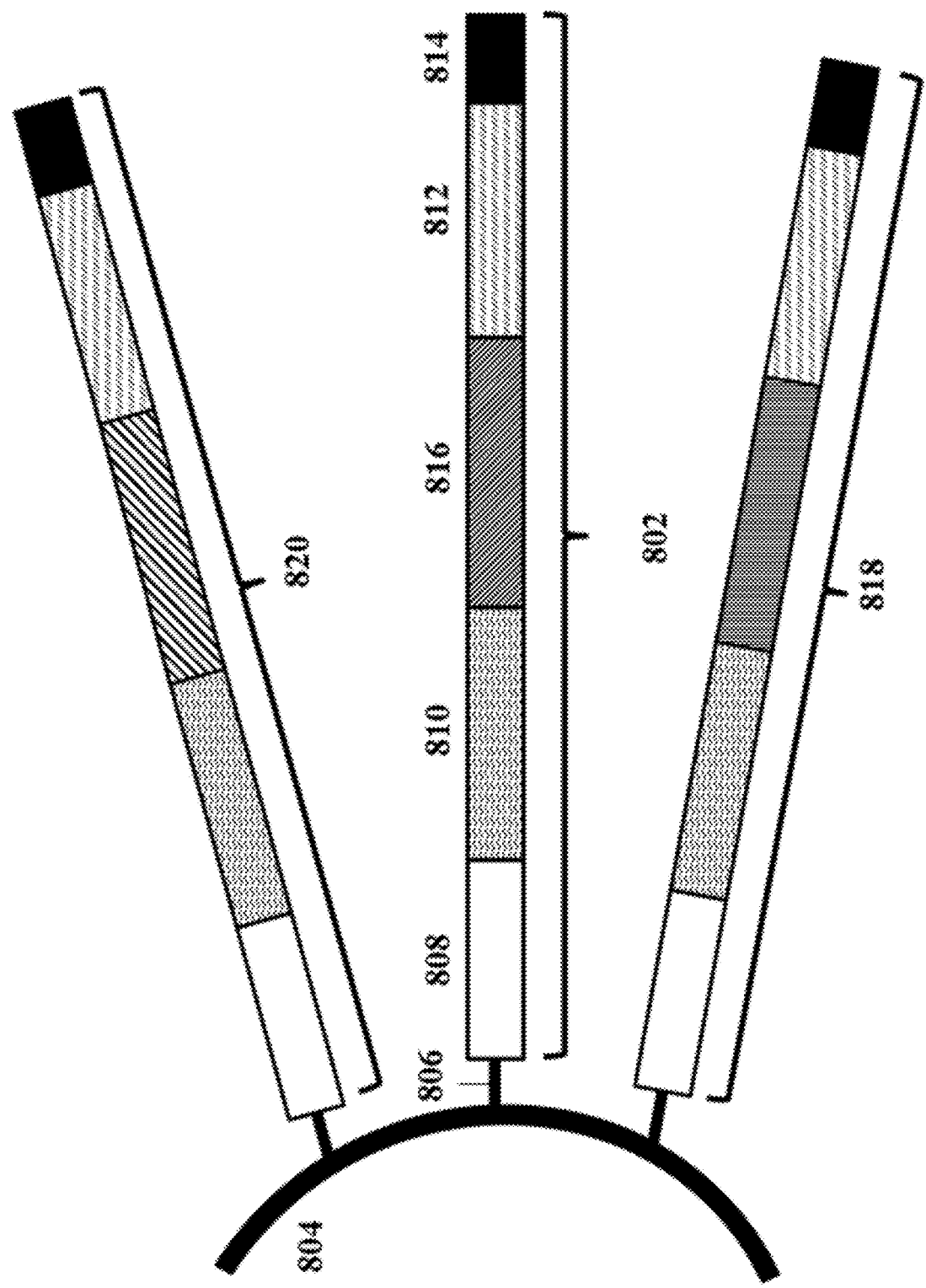
FIG. 8 illustrates an example of a barcode carrying bead.

FIG. 8 illustrates an example of a barcode carrying bead. A nucleic acid molecule 802, such as an oligonucleotide, can be coupled to a bead 804 by a releasable linkage 806, such as, for example, a disulfide linker. The same bead 804 may be coupled (e.g., via releasable linkage) to one or more other nucleic acid molecules 818, 820. The nucleic acid molecule 802 may be or comprise a barcode. As noted elsewhere herein, the structure of the barcode may comprise a number of sequence elements. The nucleic acid molecule 802 may comprise a functional sequence 808 that may be used in subsequent processing. For example, the functional sequence 808 may include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule 802 may comprise a barcode sequence 810 for use in barcoding the sample (e.g., DNA, RNA, protein, etc.). In some cases, the barcode sequence 810 can be bead-specific such that the barcode sequence 810 is common to all nucleic acid molecules (e.g., including nucleic acid molecule 802) coupled to the same bead 804. Alternatively or in addition, the barcode sequence 810 can be partition-specific such that the barcode sequence 810 is common to all nucleic acid molecules coupled to one or more beads that are partitioned into the same partition. The nucleic acid molecule 802 may comprise a specific priming sequence 812, such as an mRNA specific priming sequence (e.g., poly-T sequence), a targeted priming sequence, and/or a random priming sequence. The nucleic acid molecule 802 may comprise an anchoring sequence 814 to ensure that the specific priming sequence 812 hybridizes at the sequence end (e.g., of the mRNA). For example, the anchoring sequence 814 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 802 may comprise a unique molecular identifying sequence 816 (e.g., unique molecular identifier (UMI)). In some cases, the unique molecular identifying sequence 816 may comprise from about 5 to about 8 nucleotides. Alternatively, the unique molecular identifying sequence 816 may compress less than about 5 or more than about 8 nucleotides. The unique molecular identifying sequence 816 may be a unique sequence that varies across individual nucleic acid molecules (e.g., 802, 818, 820, etc.) coupled to a single bead (e.g., bead 804). In some cases, the unique molecular identifying sequence 816 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 8 shows three nucleic acid molecules 802, 818, 820 coupled to the surface of the bead 804, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 808, 810, 812, etc.) and variable or unique sequence segments (e.g., 816) between different individual nucleic acid molecules coupled to the same bead.

In operation, a biological particle (e.g., cell, DNA, RNA, etc.) can be co-partitioned along with a barcode bearing bead 804. The barcoded nucleic acid molecules 802, 818, 820 can be released from the bead 804 in the partition. By way of example, in the context of analyzing sample RNA, the poly-T segment (e.g., 812) of one of the released nucleic acid molecules (e.g., 802) can hybridize to the poly-A tail of a mRNA molecule. Reverse transcription may result in a cDNA transcript of the mRNA, but which transcript includes each of the sequence segments 808, 810, 816 of the nucleic acid molecule 802. Because the nucleic acid molecule 802 comprises an anchoring sequence 814, it will more likely hybridize to and prime reverse transcription at the sequence end of the poly-A tail of the mRNA. Within any given partition, all of the cDNA transcripts of the individual mRNA molecules may include a common barcode sequence segment 810. However, the transcripts made from the different mRNA molecules within a given partition may vary at the unique molecular identifying sequence 812 segment (e.g., UMI segment). Beneficially, even following any subsequent amplification of the contents of a given partition, the number of different UMIs can be indicative of the quantity of mRNA originating from a given partition, and thus from the biological particle (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead.

Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNase, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

Although FIG. 1 and FIG. 2 have been described in terms of providing substantially singly occupied partitions, above, in certain cases, it may be desirable to provide multiply occupied partitions, e.g., containing two, three, four or more cells and/or microcapsules (e.g., beads) comprising barcoded nucleic acid molecules (e.g., oligonucleotides) within a single partition. Accordingly, as noted above, the flow characteristics of the biological particle and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction (e.g., junction 210). In such cases, the flow and frequency of the different beads into the channel or junction may be controlled to provide for a certain ratio of microcapsules from each source, while ensuring a given pairing or combination of such beads into a partition with a given number of biological particles (e.g., one biological particle and one bead per partition).

The partitions described herein may comprise small volumes, for example, less than about 10 microliters (μL), 5 μL, 1 μL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Reagents

In accordance with certain aspects, biological particles may be partitioned along with lysis reagents in order to release the contents of the biological particles within the partition. In such cases, the lysis agents can be contacted with the biological particle suspension concurrently with, or immediately prior to, the introduction of the biological particles into the partitioning junction/droplet generation zone (e.g., junction 210), such as through an additional channel or channels upstream of the channel junction. In accordance with other aspects, additionally or alternatively, biological particles may be partitioned along with other reagents, as will be described further below.

Figure 3:
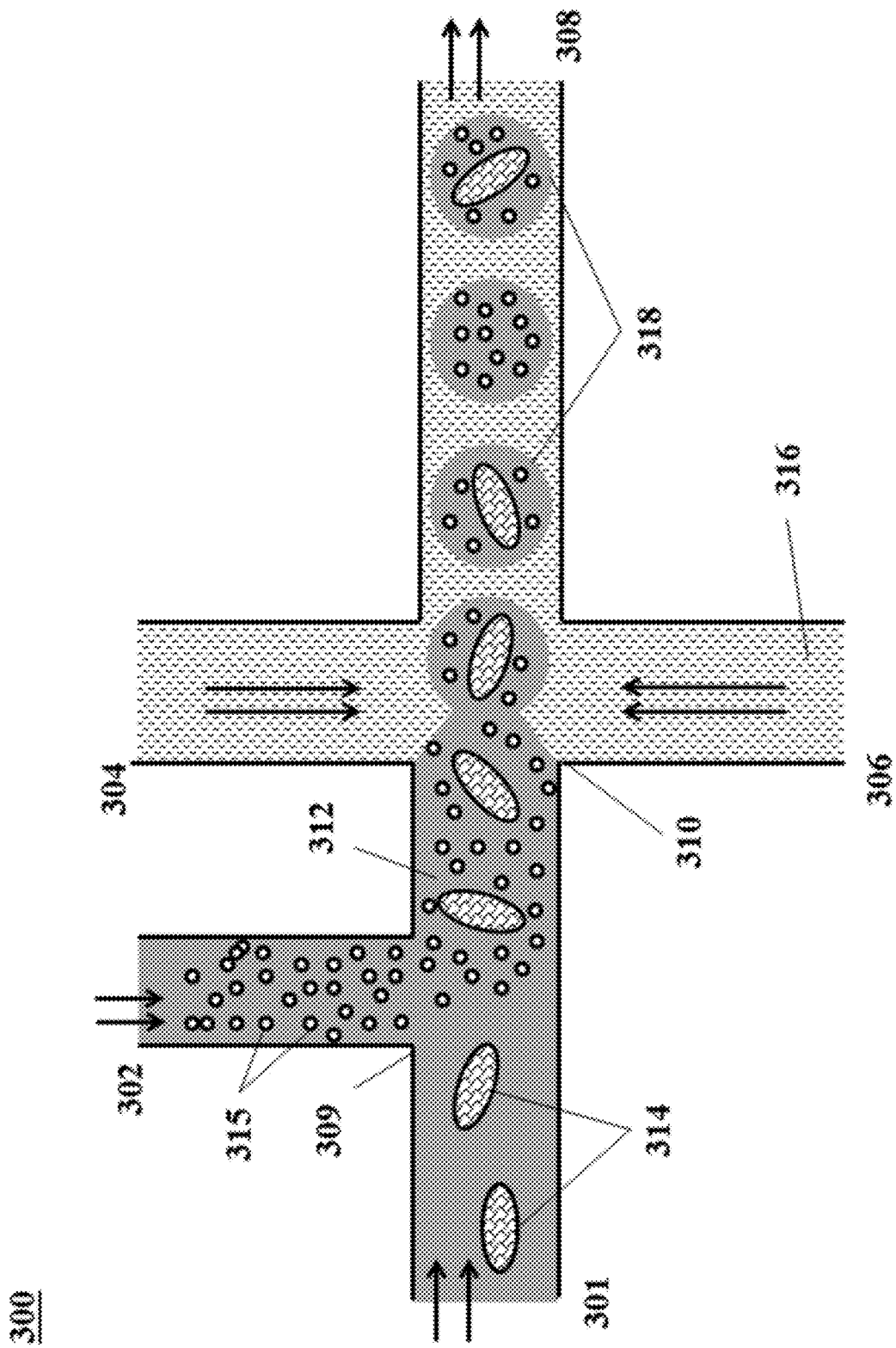
FIG. 3 shows an example of a microfluidic channel structure for co-partitioning biological particles and reagents.

FIG. 3 shows an example of a microfluidic channel structure 300 for co-partitioning biological particles and reagents. The channel structure 300 can include channel segments 301, 302, 304, 306 and 308. Channel segments 301 and 302 communicate at a first channel junction 309. Channel segments 302, 304, 306, and 308 communicate at a second channel junction 310.

In an example operation, the channel segment 301 may transport an aqueous fluid 312 that includes a plurality of biological particles 314 along the channel segment 301 into the second junction 310. As an alternative or in addition to, channel segment 301 may transport beads (e.g., gel beads). The beads may comprise barcode molecules.

For example, the channel segment 301 may be connected to a reservoir comprising an aqueous suspension of biological particles 314. Upstream of, and immediately prior to reaching, the second junction 310, the channel segment 301 may meet the channel segment 302 at the first junction 309. The channel segment 302 may transport a plurality of reagents 315 (e.g., lysis agents) suspended in the aqueous fluid 312 along the channel segment 302 into the first junction 309. For example, the channel segment 302 may be connected to a reservoir comprising the reagents 315. After the first junction 309, the aqueous fluid 312 in the channel segment 301 can carry both the biological particles 314 and the reagents 315 towards the second junction 310. In some instances, the aqueous fluid 312 in the channel segment 301 can include one or more reagents, which can be the same or different reagents as the reagents 315. A second fluid 316 that is immiscible with the aqueous fluid 312 (e.g., oil) can be delivered to the second junction 310 from each of channel segments 304 and 306. Upon meeting of the aqueous fluid 312 from the channel segment 301 and the second fluid 316 from each of channel segments 304 and 306 at the second channel junction 310, the aqueous fluid 312 can be partitioned as discrete droplets 318 in the second fluid 316 and flow away from the second junction 310 along channel segment 308. The channel segment 308 may deliver the discrete droplets 318 to an outlet reservoir fluidly coupled to the channel segment 308, where they may be harvested.

The second fluid 316 can comprise an oil, such as a fluorinated oil, that includes a fluorosurfactant for stabilizing the resulting droplets, for example, inhibiting subsequent coalescence of the resulting droplets 318.

A discrete droplet generated may include an individual biological particle 314 and/or one or more reagents 315. In some instances, a discrete droplet generated may include a barcode carrying bead (not shown), such as via other microfluidics structures described elsewhere herein. In some instances, a discrete droplet may be unoccupied (e.g., no reagents, no biological particles).

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 300 may have other geometries. For example, a microfluidic channel structure can have more than two channel junctions. For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the biological particles to cause the release of the biological particles's contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants such as, for example, Triton™ X-100 and Tween 20™. In some cases, lysis solutions may include ionic surfactants such as, for example, sarcosyl and sodium dodecyl sulfate (SDS). Electroporation, thermal, acoustic or mechanically cellular disruption may also be used in certain cases, e.g., non-emulsion based partitioning such as encapsulation of biological particles that may be in addition to or in place of droplet partitioning, where any pore size of the encapsulate is sufficiently small to retain nucleic acid fragments of a given size, following cellular disruption.

Alternatively or in addition to the lysis agents co-partitioned with the biological particles described above, other reagents can also be co-partitioned with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles, the biological particles may be exposed to an appropriate stimulus to release the biological particles or their contents from a co-partitioned microcapsule. For example, in some cases, a chemical stimulus may be co-partitioned along with an encapsulated biological particle to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative aspects, this may be a different and non-overlapping stimulus, in order to allow an encapsulated biological particle to be released into a partition at a different time from the release of nucleic acid molecules into the same partition.

Additional reagents may also be co-partitioned with the biological particles, such as endonucleases to fragment a biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNase, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of biological particles, such as RNA, DNA, or proteins) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes can be assigned or associated with individual biological particles or populations of biological particles, in order to tag or label the biological particle's macromolecular components (and as a result, its characteristics) with the unique identifiers. These unique identifiers can then be used to attribute the biological particle's components and characteristics to an individual biological particle or group of biological particles.

In some aspects, this is performed by co-partitioning the individual biological particle or groups of biological particles with the unique identifiers, such as described above (with reference to FIG. 2). In some aspects, the unique identifiers are provided in the form of nucleic acid molecules (e.g., oligonucleotides) that comprise nucleic acid barcode sequences that may be attached to or otherwise associated with the nucleic acid contents of individual biological particle, or to other components of the biological particle, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned biological particles. These sequences include, e.g., targeted or random/universal amplification primer sequences for amplifying the genomic DNA from the individual biological particles within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems.

In an example, microcapsules, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules form the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles, and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 4:
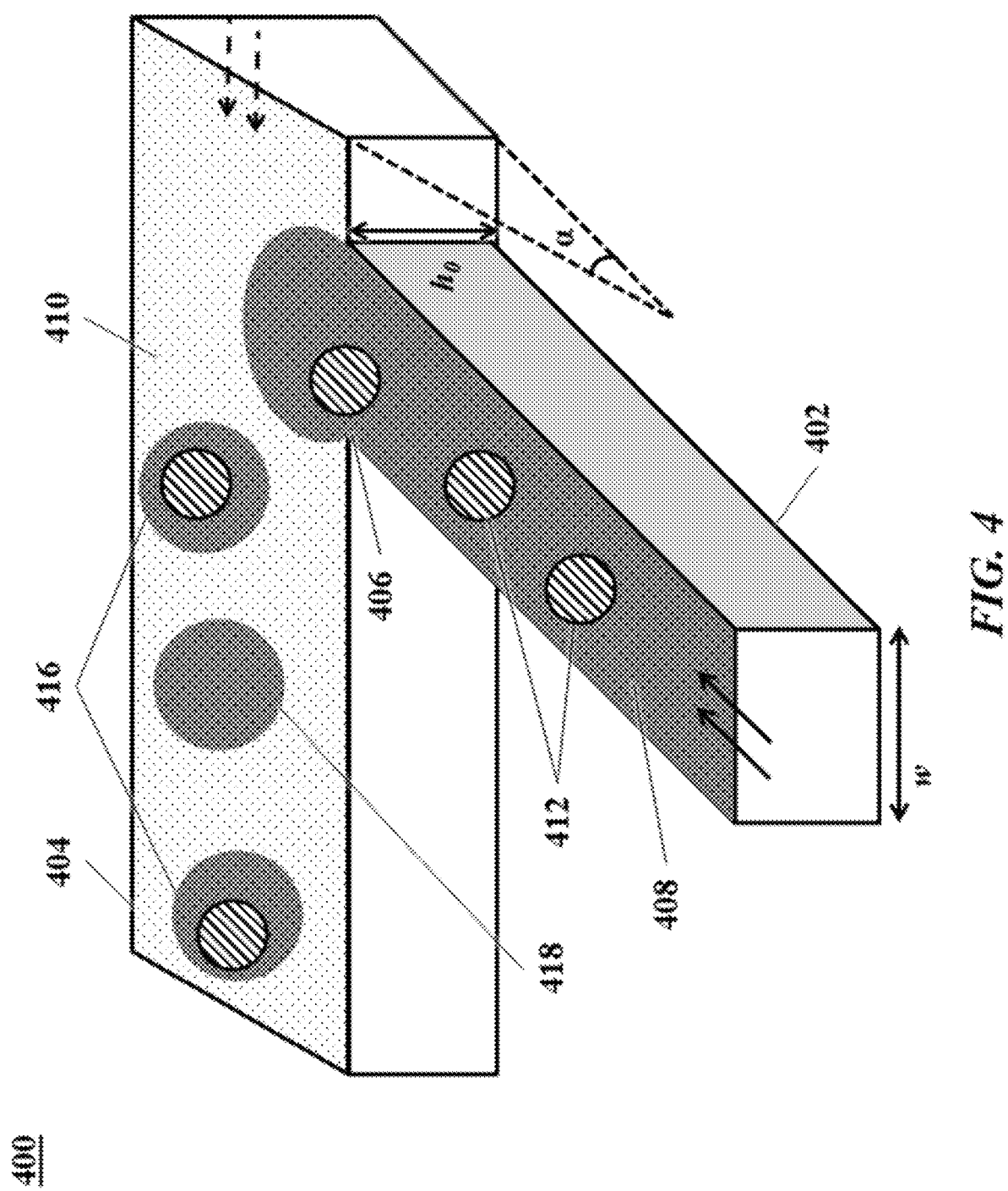
FIG. 4 shows an example of a microfluidic channel structure for the controlled partitioning of beads into discrete droplets.

FIG. 4 shows an example of a microfluidic channel structure for the controlled partitioning of beads into discrete droplets. A channel structure 400 can include a channel segment 402 communicating at a channel junction 406 (or intersection) with a reservoir 404. The reservoir 404 can be a chamber. Any reference to "reservoir," as used herein, can also refer to a "chamber." In operation, an aqueous fluid 408 that includes suspended beads 412 may be transported along the channel segment 402 into the junction 406 to meet a second fluid 410 that is immiscible with the aqueous fluid 408 in the reservoir 404 to create droplets 416, 418 of the aqueous fluid 408 flowing into the reservoir 404. At the junction 406 where the aqueous fluid 408 and the second fluid 410 meet, droplets can form based on factors such as the hydrodynamic forces at the junction 406, flow rates of the two fluids 408, 410, fluid properties, and certain geometric parameters (e.g., w, $h_0$, $\alpha$, etc.) of the channel structure 400. A plurality of droplets can be collected in the reservoir 404 by continuously injecting the aqueous fluid 408 from the channel segment 402 through the junction 406.

A discrete droplet generated may include a bead (e.g., as in occupied droplets 416). Alternatively, a discrete droplet generated may include more than one bead. Alternatively, a discrete droplet generated may not include any beads (e.g., as in unoccupied droplet 418). In some instances, a discrete droplet generated may contain one or more biological particles, as described elsewhere herein. In some instances, a discrete droplet generated may comprise one or more reagents, as described elsewhere herein.

In some instances, the aqueous fluid 408 can have a substantially uniform concentration or frequency of beads 412. The beads 412 can be introduced into the channel segment 402 from a separate channel (not shown in FIG. 4). The frequency of beads 412 in the channel segment 402 may be controlled by controlling the frequency in which the beads 412 are introduced into the channel segment 402 and/or the relative flow rates of the fluids in the channel segment 402 and the separate channel. In some instances, the beads can be introduced into the channel segment 402 from a plurality of different channels, and the frequency controlled accordingly.

In some instances, the aqueous fluid 408 in the channel segment 402 can comprise biological particles (e.g., described with reference to FIGS. 1 and 2). In some instances, the aqueous fluid 408 can have a substantially uniform concentration or frequency of biological particles. As with the beads, the biological particles can be introduced into the channel segment 402 from a separate channel. The frequency or concentration of the biological particles in the aqueous fluid 408 in the channel segment 402 may be controlled by controlling the frequency in which the biological particles are introduced into the channel segment 402 and/or the relative flow rates of the fluids in the channel segment 402 and the separate channel. In some instances, the biological particles can be introduced into the channel segment 402 from a plurality of different channels, and the frequency controlled accordingly. In some instances, a first separate channel can introduce beads and a second separate channel can introduce biological particles into the channel segment 402. The first separate channel introducing the beads may be upstream or downstream of the second separate channel introducing the biological particles.

The second fluid 410 can comprise an oil, such as a fluorinated oil, that includes a fluorosurfactant for stabilizing the resulting droplets, for example, inhibiting subsequent coalescence of the resulting droplets.

In some instances, the second fluid 410 may not be subjected to and/or directed to any flow in or out of the reservoir 404. For example, the second fluid 410 may be substantially stationary in the reservoir 404. In some instances, the second fluid 410 may be subjected to flow within the reservoir 404, but not in or out of the reservoir 404, such as via application of pressure to the reservoir 404 and/or as affected by the incoming flow of the aqueous fluid 408 at the junction 406. Alternatively, the second fluid 410 may be subjected and/or directed to flow in or out of the reservoir 404. For example, the reservoir 404 can be a channel directing the second fluid 410 from upstream to downstream, transporting the generated droplets.

The channel structure 400 at or near the junction 406 may have certain geometric features that at least partly determine the sizes of the droplets formed by the channel structure 400. The channel segment 402 can have a height, $h_0$ and width, w, at or near the junction 406. By way of example, the channel segment 402 can comprise a rectangular cross-section that leads to a reservoir 404 having a wider cross-section (such as in width or diameter). Alternatively, the cross-section of the channel segment 402 can be other shapes, such as a circular shape, trapezoidal shape, polygonal shape, or any other shapes. The top and bottom walls of the reservoir 404 at or near the junction 406 can be inclined at an expansion angle, α. The expansion angle, α, allows the tongue (portion of the aqueous fluid 408 leaving channel segment 402 at junction 406 and entering the reservoir 404 before droplet formation) to increase in depth and facilitate decrease in curvature of the intermediately formed droplet. Droplet size may decrease with increasing expansion angle. The resulting droplet radius, $R_d$, may be predicted by the following equation for the aforementioned geometric parameters of $h_0$, w, and α:

$$R_d \approx 0.44\left(1 + 2.2\sqrt{\tan\alpha}\,\frac{w}{h_0}\right)\frac{h_0}{\sqrt{\tan\alpha}}$$

By way of example, for a channel structure with w=21 μm, h=21 μm, and α=3°, the predicted droplet size is 121 μm. In another example, for a channel structure with w=25 h=25 μm, and α=5°, the predicted droplet size is 123 μm. In another example, for a channel structure with w=28 μm, h=28 μm, and α=7°, the predicted droplet size is 124 μm.

In some instances, the expansion angle, α, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 408 entering the junction 406 can be between about 0.04 microliters (μL)/minute (min) and about 40 μL/min. In some instances, the flow rate of the aqueous fluid 408 entering the junction 406 can be between about 0.01 microliters (μL)/minute (min) and about 100 μL/min. Alternatively, the flow rate of the aqueous fluid 408 entering the junction 406 can be less than about 0.01 μL/min. Alternatively, the flow rate of the aqueous fluid 408 entering the junction 406 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120, 130 μL/min, 140 μL/min, 150 μL/min, or greater. At lower flow rates, such as flow rates of about less than or equal to 10 microliters/minute, the droplet radius may not be dependent on the flow rate of the aqueous fluid 408 entering the junction 406.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 406) between aqueous fluid 408 channel segments (e.g., channel segment 402) and the reservoir 404. Alternatively or in addition, the throughput of droplet generation can be increased by increasing the flow rate of the aqueous fluid 408 in the channel segment 402.

Figure 5:
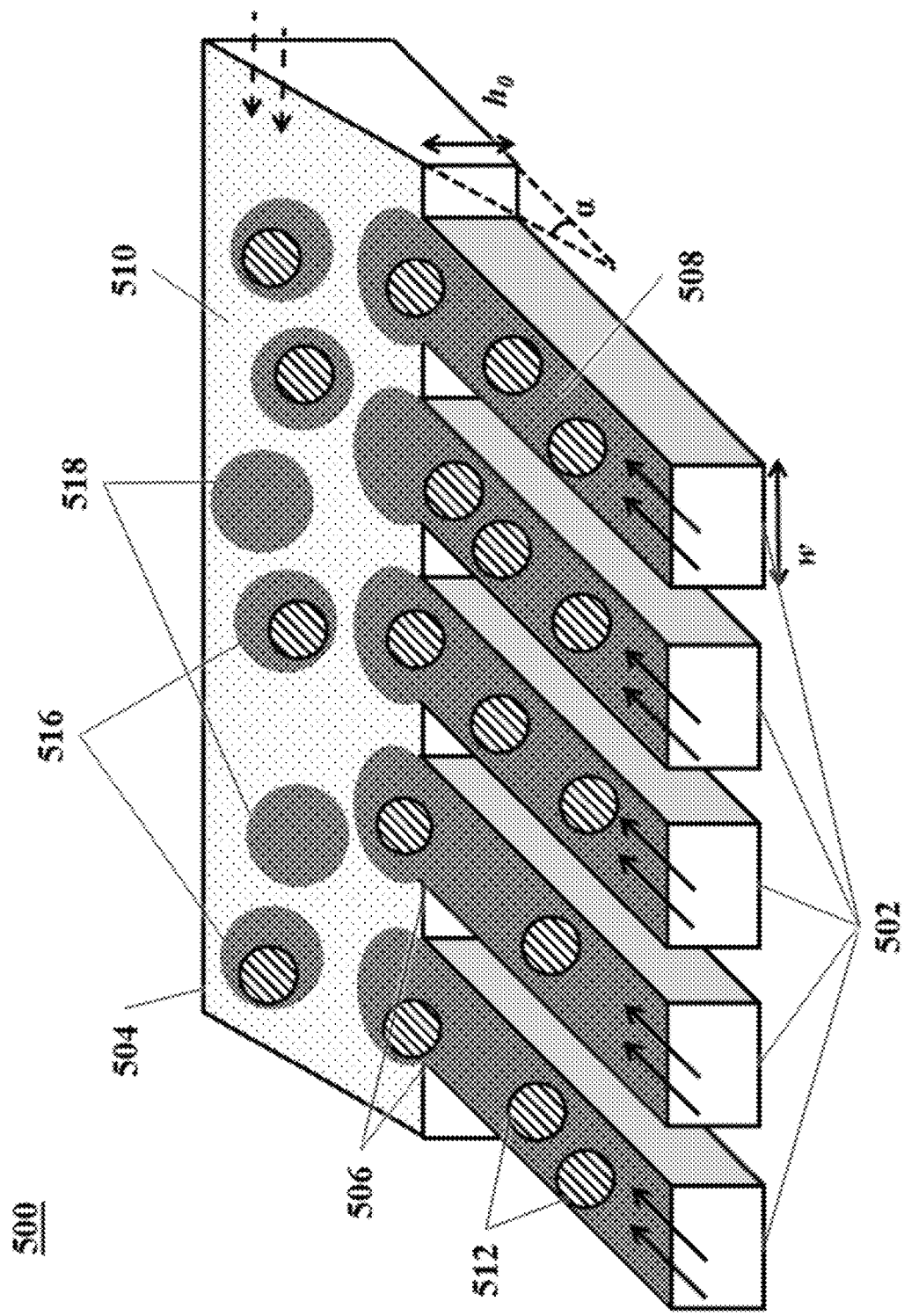
FIG. 5 shows an example of a microfluidic channel structure for increased droplet generation throughput.

FIG. 5 shows an example of a microfluidic channel structure for increased droplet generation throughput. A microfluidic channel structure 500 can comprise a plurality of channel segments 502 and a reservoir 504. Each of the plurality of channel segments 502 may be in fluid communication with the reservoir 504. The channel structure 500 can comprise a plurality of channel junctions 506 between the plurality of channel segments 502 and the reservoir 504. Each channel junction can be a point of droplet generation. The channel segment 402 from the channel structure 400 in FIG. 4 and any description to the components thereof may correspond to a given channel segment of the plurality of channel segments 502 in channel structure 500 and any description to the corresponding components thereof. The reservoir 404 from the channel structure 400 and any description to the components thereof may correspond to the reservoir 504 from the channel structure 500 and any description to the corresponding components thereof.

Each channel segment of the plurality of channel segments 502 may comprise an aqueous fluid 508 that includes suspended beads 512. The reservoir 504 may comprise a second fluid 510 that is immiscible with the aqueous fluid 508. In some instances, the second fluid 510 may not be subjected to and/or directed to any flow in or out of the reservoir 504. For example, the second fluid 510 may be substantially stationary in the reservoir 504. In some instances, the second fluid 510 may be subjected to flow within the reservoir 504, but not in or out of the reservoir 504, such as via application of pressure to the reservoir 504 and/or as affected by the incoming flow of the aqueous fluid 508 at the junctions. Alternatively, the second fluid 510 may be subjected and/or directed to flow in or out of the reservoir 504. For example, the reservoir 504 can be a channel directing the second fluid 510 from upstream to downstream, transporting the generated droplets.

In operation, the aqueous fluid 508 that includes suspended beads 512 may be transported along the plurality of channel segments 502 into the plurality of junctions 506 to meet the second fluid 510 in the reservoir 504 to create droplets 516, 518. A droplet may form from each channel segment at each corresponding junction with the reservoir 504. At the junction where the aqueous fluid 508 and the second fluid 510 meet, droplets can form based on factors such as the hydrodynamic forces at the junction, flow rates of the two fluids 508, 510, fluid properties, and certain geometric parameters (e.g., w, $h_O$, α, etc.) of the channel structure 500, as described elsewhere herein. A plurality of droplets can be collected in the reservoir 504 by continuously injecting the aqueous fluid 508 from the plurality of channel segments 502 through the plurality of junctions 506. Throughput may significantly increase with the parallel channel configuration of channel structure 500. For example, a channel structure having five inlet channel segments comprising the aqueous fluid 508 may generate droplets five times as frequently than a channel structure having one inlet channel segment, provided that the fluid flow rate in the channel segments are substantially the same. The fluid flow rate in the different inlet channel segments may or may not be substantially the same. A channel structure may have as many parallel channel segments as is practical and allowed for the size of the reservoir. For example, the channel structure may have at least about 2, 3, 4, 5, 6, 7, 8, 9, 10, 20, 30, 40, 50, 60, 70, 80, 90, 100, 150, 500, 250, 300, 350, 400, 450, 500, 600, 700, 800, 900, 1000, 1500, 5000 or more parallel or substantially parallel channel segments.

The geometric parameters, w, $h_O$, and α, may or may not be uniform for each of the channel segments in the plurality of channel segments 502. For example, each channel segment may have the same or different widths at or near its respective channel junction with the reservoir 504. For example, each channel segment may have the same or different height at or near its respective channel junction with the reservoir 504. In another example, the reservoir 504 may have the same or different expansion angle at the different channel junctions with the plurality of channel segments 502. When the geometric parameters are uniform, beneficially, droplet size may also be controlled to be uniform even with the increased throughput. In some instances, when it is desirable to have a different distribution of droplet sizes, the geometric parameters for the plurality of channel segments 502 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

Figure 6:
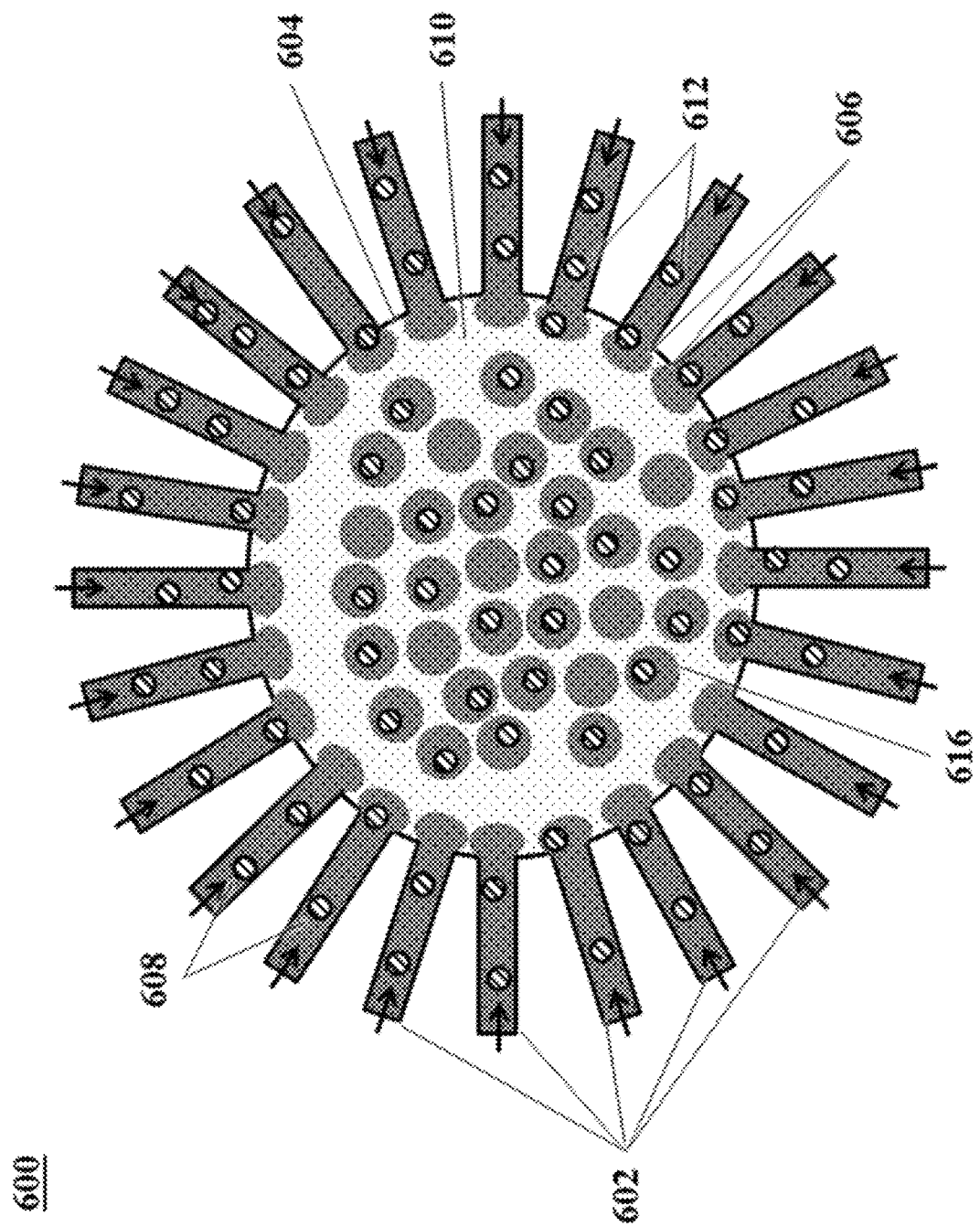
FIG. 6 shows another example of a microfluidic channel structure for increased droplet generation throughput.

FIG. 6 shows another example of a microfluidic channel structure for increased droplet generation throughput. A microfluidic channel structure 600 can comprise a plurality of channel segments 602 arranged generally circularly around the perimeter of a reservoir 604. Each of the plurality of channel segments 602 may be in fluid communication with the reservoir 604. The channel structure 600 can comprise a plurality of channel junctions 606 between the plurality of channel segments 602 and the reservoir 604. Each channel junction can be a point of droplet generation. The channel segment 402 from the channel structure 400 in FIG. 2 and any description to the components thereof may correspond to a given channel segment of the plurality of channel segments 602 in channel structure 600 and any description to the corresponding components thereof. The reservoir 404 from the channel structure 400 and any description to the components thereof may correspond to the reservoir 604 from the channel structure 600 and any description to the corresponding components thereof.

Each channel segment of the plurality of channel segments 602 may comprise an aqueous fluid 608 that includes suspended beads 612. The reservoir 604 may comprise a second fluid 610 that is immiscible with the aqueous fluid 608. In some instances, the second fluid 610 may not be subjected to and/or directed to any flow in or out of the reservoir 604. For example, the second fluid 610 may be substantially stationary in the reservoir 604. In some instances, the second fluid 610 may be subjected to flow within the reservoir 604, but not in or out of the reservoir 604, such as via application of pressure to the reservoir 604 and/or as affected by the incoming flow of the aqueous fluid 608 at the junctions. Alternatively, the second fluid 610 may be subjected and/or directed to flow in or out of the reservoir 604. For example, the reservoir 604 can be a channel directing the second fluid 610 from upstream to downstream, transporting the generated droplets.

In operation, the aqueous fluid 608 that includes suspended beads 612 may be transported along the plurality of channel segments 602 into the plurality of junctions 606 to meet the second fluid 610 in the reservoir 604 to create a plurality of droplets 616. A droplet may form from each channel segment at each corresponding junction with the reservoir 604. At the junction where the aqueous fluid 608 and the second fluid 610 meet, droplets can form based on factors such as the hydrodynamic forces at the junction, flow rates of the two fluids 608, 610, fluid properties, and certain geometric parameters (e.g., widths and heights of the channel segments 602, expansion angle of the reservoir 604, etc.) of the channel structure 600, as described elsewhere herein. A plurality of droplets can be collected in the reservoir 604 by continuously injecting the aqueous fluid 608 from the plurality of channel segments 602 through the plurality of junctions 606. Throughput may significantly increase with the substantially parallel channel configuration of the channel structure 600. A channel structure may have as many substantially parallel channel segments as is practical and allowed for by the size of the reservoir. For example, the channel structure may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 5000 or more parallel or substantially parallel channel segments. The plurality of channel segments may be substantially evenly spaced apart, for example, around an edge or perimeter of the reservoir. Alternatively, the spacing of the plurality of channel segments may be uneven.

The reservoir 604 may have an expansion angle, α (not shown in FIG. 6) at or near each channel junction. Each channel segment of the plurality of channel segments 602 may have a width, w, and a height, $h_O$, at or near the channel junction. The geometric parameters, w, $h_O$, and α, may or may not be uniform for each of the channel segments in the plurality of channel segments 602. For example, each channel segment may have the same or different widths at or near its respective channel junction with the reservoir 604. For example, each channel segment may have the same or different height at or near its respective channel junction with the reservoir 604.

The reservoir 604 may have the same or different expansion angle at the different channel junctions with the plurality of channel segments 602. For example, a circular reservoir (as shown in FIG. 6) may have a conical, dome-like, or hemispherical ceiling (e.g., top wall) to provide the same or substantially same expansion angle for each channel segments 602 at or near the plurality of channel junctions 606. When the geometric parameters are uniform, beneficially, resulting droplet size may be controlled to be uniform even with the increased throughput. In some instances, when it is desirable to have a different distribution of droplet sizes, the geometric parameters for the plurality of channel segments 602 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size. The beads and/or biological particle injected into the droplets may or may not have uniform size.

Figure 7A:
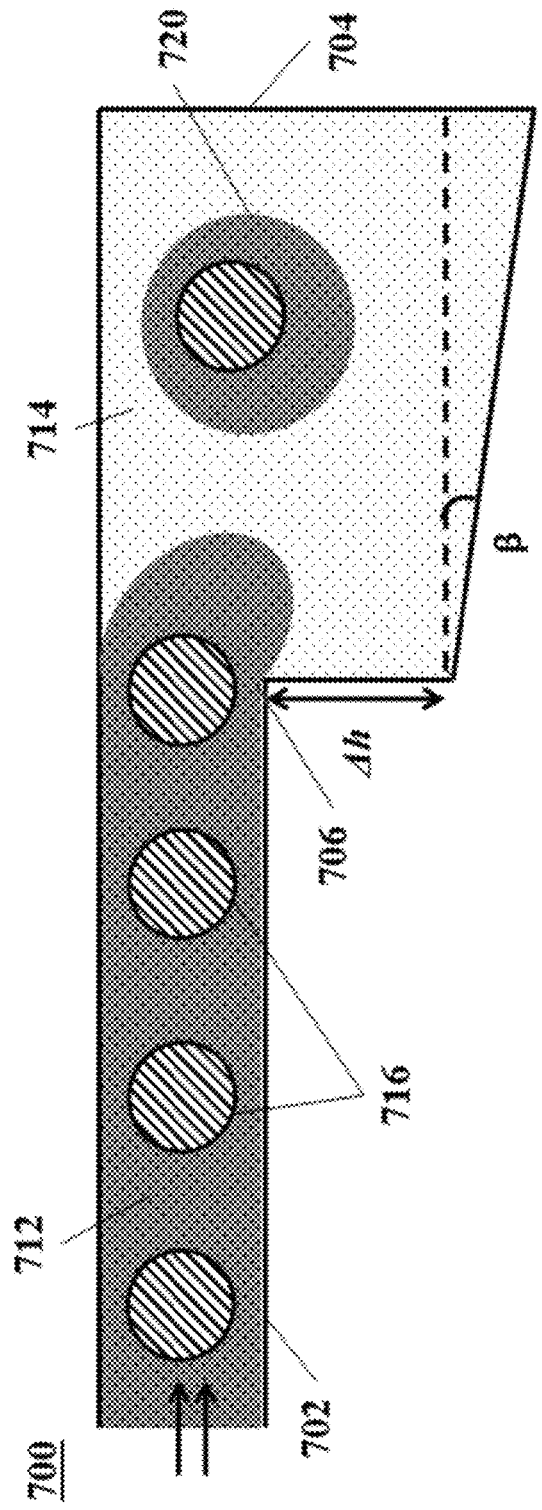
FIG. 7A shows a cross-section view of another example of a microfluidic channel structure with a geometric feature for controlled partitioning.
Figure 7B:
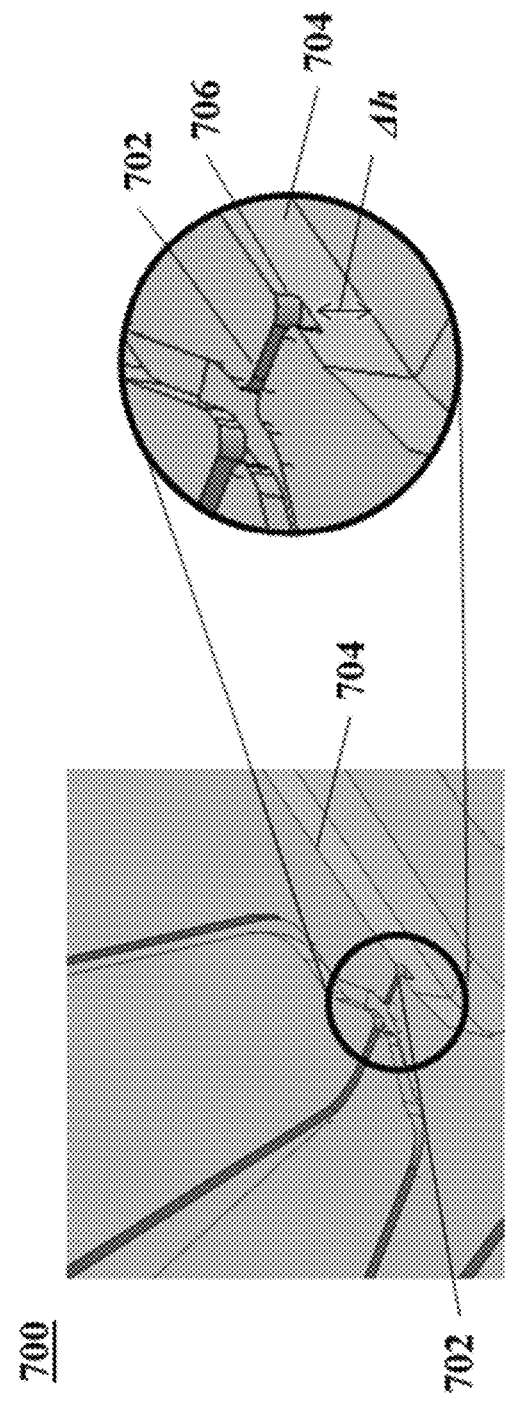
FIG. 7B shows a perspective view of the channel structure of FIG. 7A.

FIG. 7A shows a cross-section view of another example of a microfluidic channel structure with a geometric feature for controlled partitioning. A channel structure 700 can include a channel segment 702 communicating at a channel junction 706 (or intersection) with a reservoir 704. In some instances, the channel structure 700 and one or more of its components can correspond to the channel structure 100 and one or more of its components. FIG. 7B shows a perspective view of the channel structure 700 of FIG. 7A.

An aqueous fluid 712 comprising a plurality of particles 716 may be transported along the channel segment 702 into the junction 706 to meet a second fluid 714 (e.g., oil, etc.) that is immiscible with the aqueous fluid 712 in the reservoir 704 to create droplets 720 of the aqueous fluid 712 flowing into the reservoir 704. At the junction 706 where the aqueous fluid 712 and the second fluid 714 meet, droplets can form based on factors such as the hydrodynamic forces at the junction 706, relative flow rates of the two fluids 712, 714, fluid properties, and certain geometric parameters (e.g., $\Delta h$, etc.) of the channel structure 700. A plurality of droplets can be collected in the reservoir 704 by continuously injecting the aqueous fluid 712 from the channel segment 702 at the junction 706.

A discrete droplet generated may comprise one or more particles of the plurality of particles 716. As described elsewhere herein, a particle may be any particle, such as a bead, cell bead, gel bead, biological particle, macromolecular constituents of biological particle, or other particles. Alternatively, a discrete droplet generated may not include any particles.

In some instances, the aqueous fluid 712 can have a substantially uniform concentration or frequency of particles 716. As described elsewhere herein (e.g., with reference to FIG. 4), the particles 716 (e.g., beads) can be introduced into the channel segment 702 from a separate channel (not shown in FIG. 7). The frequency of particles 716 in the channel segment 702 may be controlled by controlling the frequency in which the particles 716 are introduced into the channel segment 702 and/or the relative flow rates of the fluids in the channel segment 702 and the separate channel. In some instances, the particles 716 can be introduced into the channel segment 702 from a plurality of different channels, and the frequency controlled accordingly. In some instances, different particles may be introduced via separate channels. For example, a first separate channel can introduce beads and a second separate channel can introduce biological particles into the channel segment 702. The first separate channel introducing the beads may be upstream or downstream of the second separate channel introducing the biological particles.

In some instances, the second fluid 714 may not be subjected to and/or directed to any flow in or out of the reservoir 704. For example, the second fluid 714 may be substantially stationary in the reservoir 704. In some instances, the second fluid 714 may be subjected to flow within the reservoir 704, but not in or out of the reservoir 704, such as via application of pressure to the reservoir 704 and/or as affected by the incoming flow of the aqueous fluid 712 at the junction 706. Alternatively, the second fluid 714 may be subjected and/or directed to flow in or out of the reservoir 704. For example, the reservoir 704 can be a channel directing the second fluid 714 from upstream to downstream, transporting the generated droplets.

The channel structure 700 at or near the junction 706 may have certain geometric features that at least partly determine the sizes and/or shapes of the droplets formed by the channel structure 700. The channel segment 702 can have a first cross-section height, $h_1$, and the reservoir 704 can have a second cross-section height, $h_2$. The first cross-section height, $h_1$, and the second cross-section height, $h_2$, may be different, such that at the junction 706, there is a height difference of $\Delta h$. The second cross-section height, $h_2$, may be greater than the first cross-section height, $h_1$. In some instances, the reservoir may thereafter gradually increase in cross-section height, for example, the more distant it is from the junction 706. In some instances, the cross-section height of the reservoir may increase in accordance with expansion angle, $\beta$, at or near the junction 706. The height difference, $\Delta h$, and/or expansion angle, $\beta$, can allow the tongue (portion of the aqueous fluid 712 leaving channel segment 702 at junction 706 and entering the reservoir 704 before droplet formation) to increase in depth and facilitate decrease in curvature of the intermediately formed droplet. For example, droplet size may decrease with increasing height difference and/or increasing expansion angle.

The height difference, $\Delta h$, can be at least about 1 μm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 μm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 μm or less. In some instances, the expansion angle, $\beta$, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

In some instances, the flow rate of the aqueous fluid 712 entering the junction 706 can be between about 0.04 microliters (μL)/minute (min) and about 40 μL/min. In some instances, the flow rate of the aqueous fluid 712 entering the junction 706 can be between about 0.01 microliters (μL)/minute (min) and about 100 μL/min. Alternatively, the flow rate of the aqueous fluid 712 entering the junction 706 can be less than about 0.01 µL/min. Alternatively, the flow rate of the aqueous fluid 712 entering the junction 706 can be greater than about 40 µL/min, such as 45 µL/min, 50 µL/min, 55 µL/min, 60 µL/min, 65 µL/min, 70 µL/min, 75 µL/min, 80 µL/min, 85 µL/min, 90 µL/min, 95 µL/min, 100 µL/min, 110 µL/min, 120 µL/min, 130 µL/min, 140 µL/min, 150 µt/min, or greater. At lower flow rates, such as flow rates of about less than or equal to 10 microliters/minute, the droplet radius may not be dependent on the flow rate of the aqueous fluid 712 entering the junction 706. The second fluid 714 may be stationary, or substantially stationary, in the reservoir 704. Alternatively, the second fluid 714 may be flowing, such as at the above flow rates described for the aqueous fluid 712.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

While FIGS. 7A and 7B illustrate the height difference, Δh, being abrupt at the junction 706 (e.g., a step increase), the height difference may increase gradually (e.g., from about 0 µm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 706, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIGS. 7A and 7B illustrate the expanding reservoir cross-section height as linear (e.g., constant expansion angle, β), the cross-section height may expand non-linearly. For example, the reservoir may be defined at least partially by a dome-like (e.g., hemispherical) shape having variable expansion angles. The cross-section height may expand in any shape.

The channel networks, e.g., as described above or elsewhere herein, can be fluidly coupled to appropriate fluidic components. For example, the inlet channel segments are fluidly coupled to appropriate sources of the materials they are to deliver to a channel junction. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like. Likewise, the outlet channel segment (e.g., channel segment 208, reservoir 604, etc.) may be fluidly coupled to a receiving vessel or conduit for the partitioned cells for subsequent processing. Again, this may be a reservoir defined in the body of a microfluidic device, or it may be a fluidic conduit for delivering the partitioned cells to a subsequent process operation, instrument or component.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

Computer Systems

Figure 12:
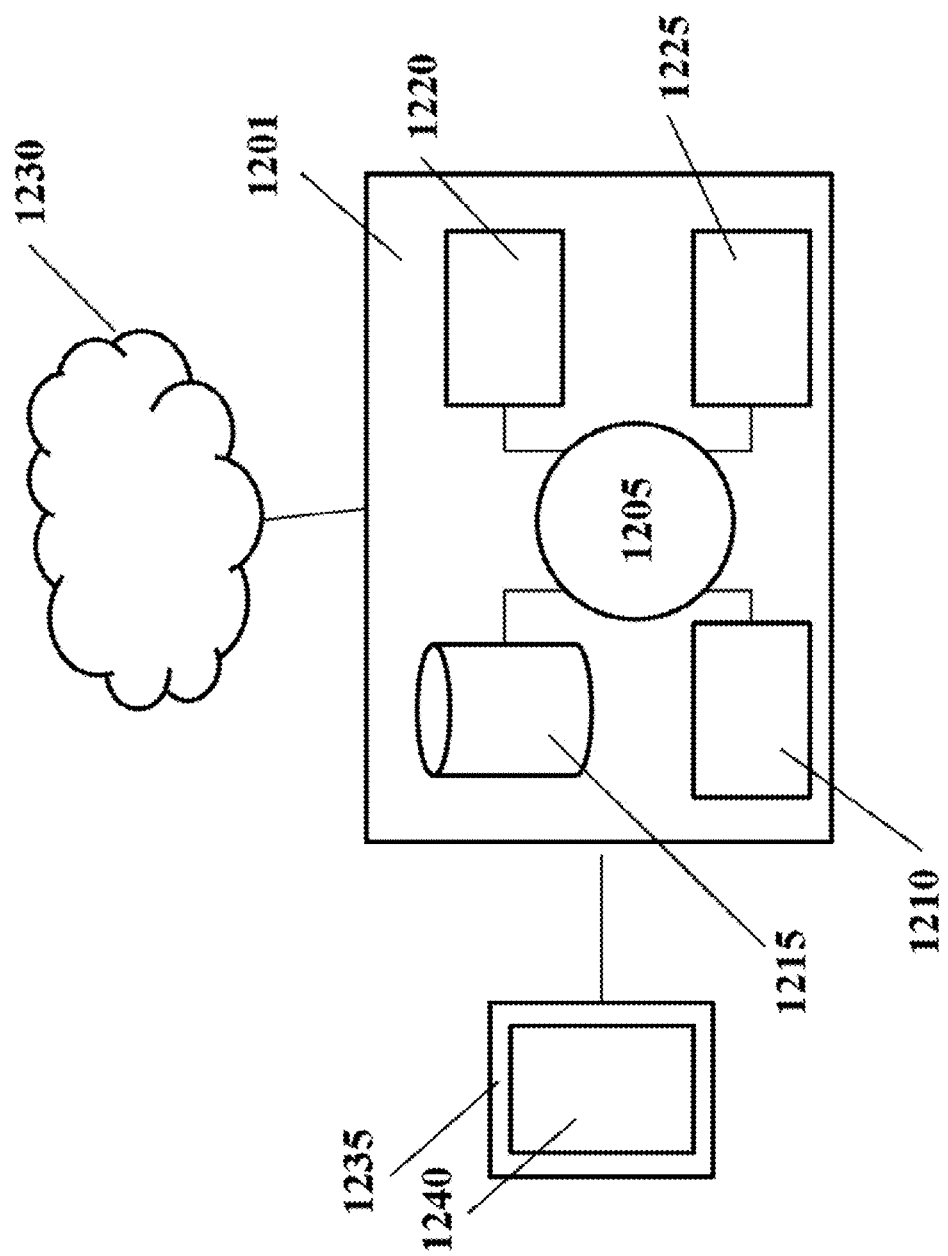
FIG. 12 shows a computer system that is programmed or otherwise configured to implement methods provided herein.

The present disclosure provides computer systems that are programmed to implement methods of the disclosure. FIG. 12 shows a computer system 1201 that is programmed or otherwise configured to (i) control a microfluidics system (e.g., fluid flow), (ii) sort occupied droplets from unoccupied droplets, (iii) polymerize droplets, (iv) perform sequencing applications, (v) generate and maintain a library of barcoded nucleic acid molecules, (vi) analyze sequencing data, (vii) mapping sequencing data to a reference genome, (viii) assessing epigenetic state or characteristics based on the sequencing data, (ix) identifying nucleosomal positions across the genome, (x) identifying DNA footprints, (xi) generate regulatory networks based on epigenetic state of the DNA molecules, (xii) comparing epigenetic states among cells or populations of cells. The computer system 1201 can regulate various aspects of the present disclosure, such as, for example, a microfluidic system, droplet formation, gel bead preparation, sequencing, and analysis of sequencing data. The computer system 1201 can be an electronic device of a user or a computer system that is remotely located with respect to the electronic device. The electronic device can be a mobile electronic device.

The computer system 1201 includes a central processing unit (CPU, also "processor" and "computer processor" herein) 1205, which can be a single core or multi core processor, or a plurality of processors for parallel processing. The computer system 1201 also includes memory or memory location 1210 (e.g., random-access memory, read-only memory, flash memory), electronic storage unit 1215 (e.g., hard disk), communication interface 1220 (e.g., network adapter) for communicating with one or more other systems, and peripheral devices 1225, such as cache, other memory, data storage and/or electronic display adapters. The memory 1210, storage unit 1215, interface 1220 and peripheral devices 1225 are in communication with the CPU 1205 through a communication bus (solid lines), such as a motherboard. The storage unit 1215 can be a data storage unit (or data repository) for storing data. The computer system 1201 can be operatively coupled to a computer network ("network") 1230 with the aid of the communication interface 1220. The network 1230 can be the Internet, an internet and/or extranet, or an intranet and/or extranet that is in communication with the Internet. The network 1230 in some cases is a telecommunication and/or data network. The network 1230 can include one or more computer servers, which can enable distributed computing, such as cloud computing. The network 1230, in some cases with the aid of the computer system 1201, can implement a peer-to-peer network, which may enable devices coupled to the computer system 1201 to behave as a client or a server.

The CPU 1205 can execute a sequence of machine-readable instructions, which can be embodied in a program or software. The instructions may be stored in a memory location, such as the memory 1210. The instructions can be directed to the CPU 1205, which can subsequently program or otherwise configure the CPU 1205 to implement methods of the present disclosure. Examples of operations performed by the CPU 1205 can include fetch, decode, execute, and writeback.

The CPU 1205 can be part of a circuit, such as an integrated circuit. One or more other components of the system 1201 can be included in the circuit. In some cases, the circuit is an application specific integrated circuit (ASIC).

The storage unit 1215 can store files, such as drivers, libraries and saved programs. The storage unit 1215 can store user data, e.g., user preferences and user programs. The computer system 1201 in some cases can include one or more additional data storage units that are external to the computer system 1201, such as located on a remote server that is in communication with the computer system 12001 through an intranet or the Internet.

The computer system 1201 can communicate with one or more remote computer systems through the network 1230. For instance, the computer system 1201 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1201 via the network 1230.

Methods as described herein can be implemented by way of machine (e.g., computer processor) executable code stored on an electronic storage location of the computer system 1201, such as, for example, on the memory 1210 or electronic storage unit 1215. The machine executable or machine readable code can be provided in the form of software. During use, the code can be executed by the processor 1205. In some cases, the code can be retrieved from the storage unit 1215 and stored on the memory 1210 for ready access by the processor 1205. In some situations, the electronic storage unit 1215 can be precluded, and machine-executable instructions are stored on memory 1210.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1201 can include or be in communication with an electronic display 1235 that comprises a user interface (UI) 1240 for providing, for example, results of sequencing analysis, results of epigenetic state of nucleic acid molecules, comparison among cells or populations of cells with respect to their epigenetic states, results showing nucleosomal occupancy in the genome based on the sequencing data, etc.]. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 1205. The algorithm can, for example, perform sequencing, align sequence reads to a reference sequence, determine epigenetic features in order to determine epigenetic state, determine nucleosomal occupancy in the genome, determine DNA footprint, etc.].

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) from a single cell. For example, a biological particle (e.g., a cell or cell bead) is partitioned in a partition (e.g., droplet), and multiple analytes from the biological particle are processed for subsequent processing. The multiple analytes may be from the single cell. This may enable, for example, simultaneous proteomic, transcriptomic and genomic analysis of the cell.

EXAMPLES

Figure 15A:
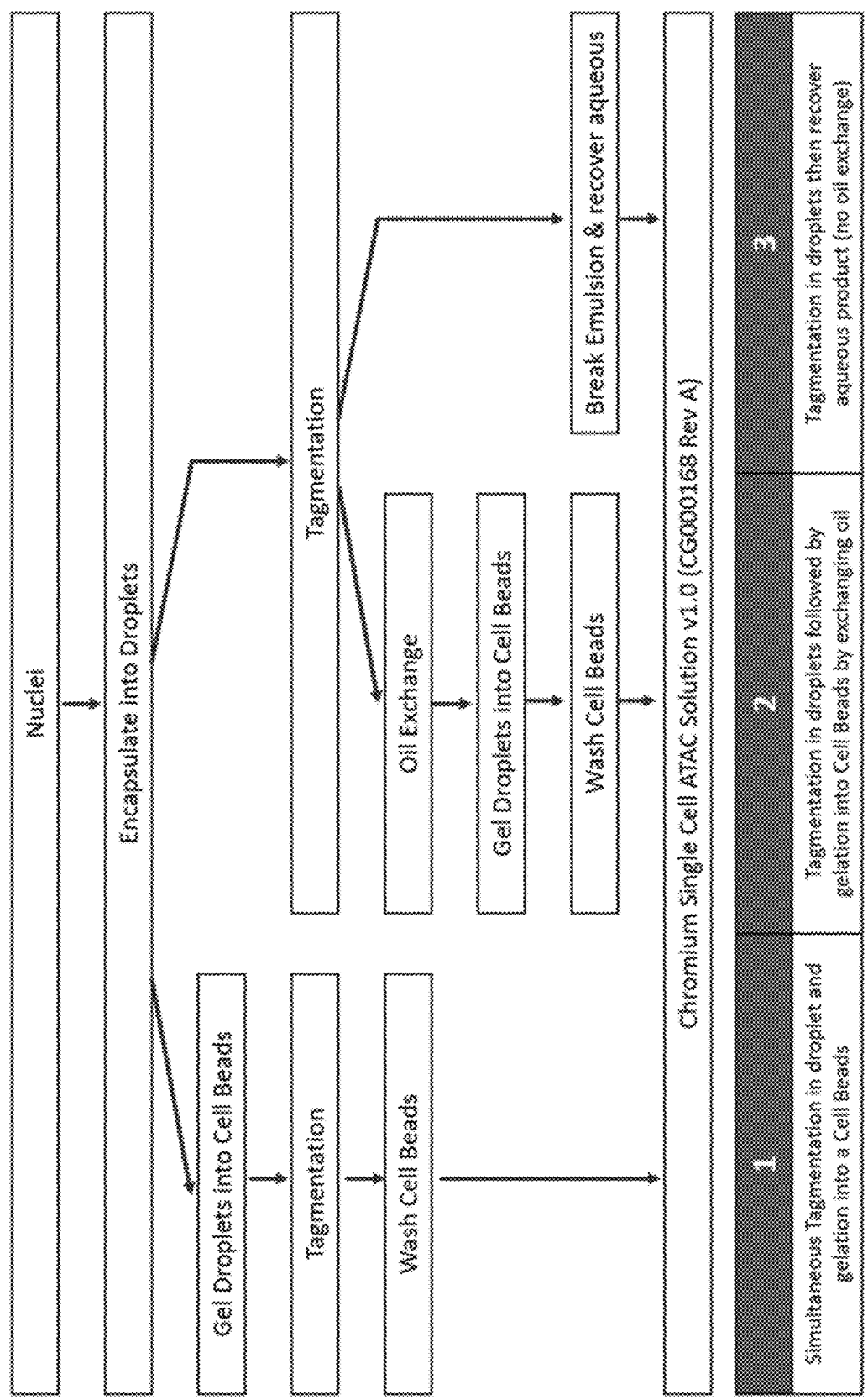
FIGS. 15A-15B shows ATAC-seq reactions performed on cell bead samples.

Example 1: Tagmentation of Samples Prior to Copper-Mediated Gelation of Cell Beads To assess the performance of ATAC-seq (Assay for Transposase-Accessible Chromatin using sequencing) in nuclei-containing cell beads formed via copper-mediated gelation of polymers (click chemistry cell beads), three workflows were tested as shown in FIG. 15A: (1) simultaneous tagmentation and gelation; (2) tagmentation prior to gelation; and (3) tagmentation in droplets with no gelation. See also, e.g., FIG. 14. Nuclei were harvested from cells and partitioned into aqueous droplets with reagents for tagmentation (tagging and fragmentation) and polymer precursors using a microfluidic device as generally described elsewhere herein. For a general description of the ATAC-seq protocol employed, see Example 12 of U.S. Patent Publication No. 2018-0340171, which is incorporated by reference herein in its entirety.

Figure 15B:
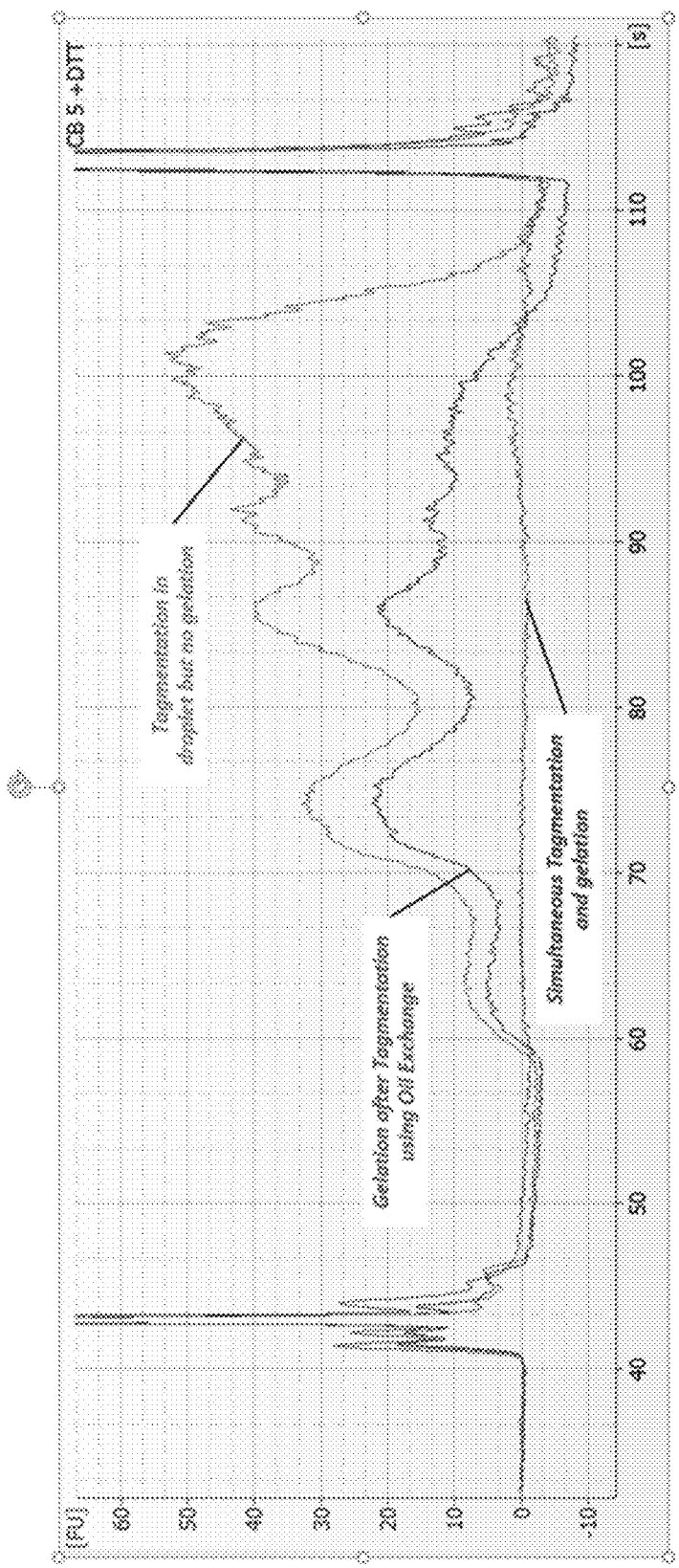
Figure 16:
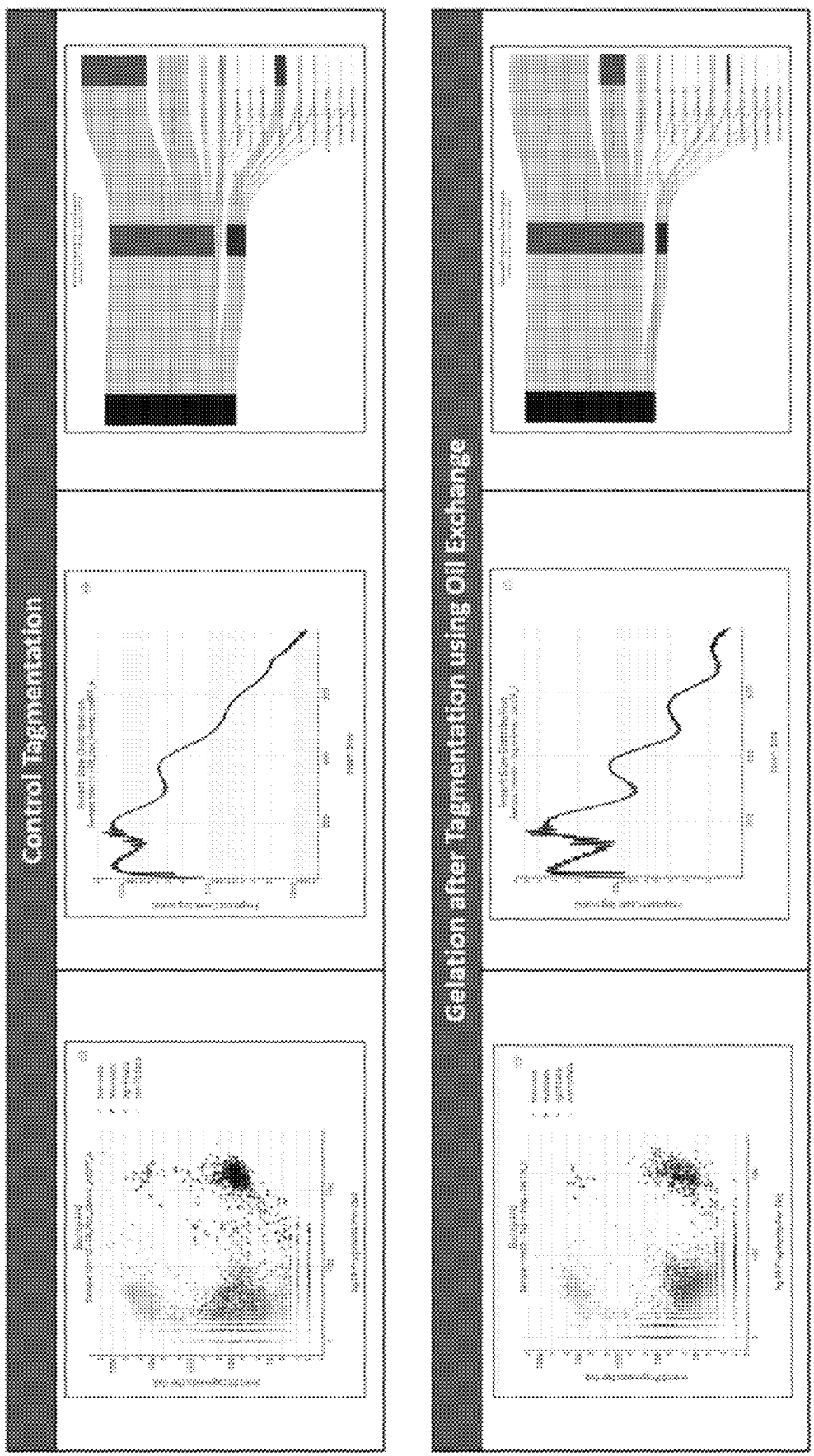
FIG. 16 shows an analysis of the ATAC-seq sequencing data generated from samples tagmented prior to cell bead gelation.

As seen in FIG. 15B, (1) simultaneous tagmentation and copper-mediated cell bead gelation failed to generate any detectable product; while (2) tagmentation in a droplet followed by copper-mediated gelation yielded insert size distributions that closely resembles expected nucleosome profiling and (3) the non-gelled control. As seen in FIG. 16 and FIG. 17, sequencing results confirmed that (2) gelation after droplet tagmentation produced data closely resembling expected nucleosome profiling and Barnyard distribution.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for determining an epigenetic characteristic of a nucleic acid molecule from a cell, comprising:
   (a) providing a cell bead comprising the cell, the cell comprising the nucleic acid molecule from the cell, wherein the nucleic acid molecule contains or is suspected of containing one or more epigenetic features;
   (b) partitioning the cell bead with a nucleic acid barcode molecule comprising a cell barcode sequence in a partition among a plurality of partitions;
   (c) in the partition, using the nucleic acid molecule and the nucleic acid barcode molecule to synthesize a barcoded nucleic acid molecule, which barcoded nucleic acid molecule comprises the cell barcode sequence, wherein the cell barcode sequence is indicative of the cell from which the nucleic acid molecule originates;
   (d) processing the barcoded nucleic acid molecule or a derivative thereof to identify the one or more epigenetic features and the cell barcode sequence; and
   (e) using the one or more epigenetic features and the cell barcode sequence to determine the epigenetic characteristic of the nucleic acid molecule as being associated with the cell,
   wherein, subsequent to (a), an enzymatic deamination reaction is performed within the cell bead, and wherein the enzymatic deamination reaction transforms at least a portion of a sequence of the nucleic acid molecule.

2. The method of claim 1, wherein the nucleic acid molecule is encapsulated in the cell bead.

3. The method of claim 1, further comprising, prior to (a), lysing the cell to release contents of the cell.

4. The method of claim 3, further comprising, subsequent to the lysing, treating the contents with one or more proteases.

5. The method of claim 1, further comprising, prior to (a), encapsulating the cell in a mixture comprising a polymer(s) or polymer precursor(s).

6. The method of claim 5, further comprising, subsequent to encapsulating the cell, producing the cell bead by performing a gelation reaction.

7. The method of claim 1, wherein the cell bead further comprises one or more reagents for processing the nucleic acid molecule.

8. The method of claim 1, wherein (a) further comprises providing a plurality of gel beads, and wherein (b) further comprises partitioning the plurality of gel beads into the plurality of partitions, wherein the partition comprises a gel bead of the plurality of gel beads, and wherein the gel bead comprises the cell barcode sequence.

9. The method of claim 1, wherein the one or more epigenetic features comprise methylation of the nucleic acid molecule, hydroxymethylation of the nucleic acid molecule, modification of histone proteins associated with the nucleic acid molecule, chromatin packaging associated with the nucleic acid molecule, or chromatin accessibility associated with the nucleic acid molecule.

10. The method of claim 1, wherein the processing in (d) comprises determining locations of a subset of the one or more epigenetic features with respect to the nucleic acid molecule.

11. The method of claim 1, wherein the plurality of partitions is a plurality of wells, and wherein the partition is a well.

12. The method of claim 1, wherein the plurality of partitions is a plurality of droplets, and wherein the partition is a droplet.

13. The method of claim 1, wherein the epigenetic characteristic of the nucleic acid molecule is an increased expression level of the nucleic acid molecule, or a decreased expression level of the nucleic acid molecule.

14. A method for determining an epigenetic characteristic of a nucleic acid molecule from a cell, comprising:
   (a) providing a cell bead comprising the cell, the cell comprising the nucleic acid molecule from the cell, wherein the nucleic acid molecule contains or is suspected of containing one or more hydroxymethylated bases;
   (b) partitioning the cell bead with a nucleic acid barcode molecule comprising a cell barcode sequence in a partition among a plurality of partitions;
   (c) in the partition, using the nucleic acid molecule and the nucleic acid barcode molecule to synthesize a barcoded nucleic acid molecule, which barcoded nucleic acid molecule comprises the cell barcode sequence, wherein the cell barcode sequence is indicative of the cell from which the nucleic acid molecule originates;
   (d) processing the barcoded nucleic acid molecule or a derivative thereof to identify the one or more hydroxymethylated bases as hydroxymethylated and the cell barcode sequence; and
   (e) using the one or more hydroxymethylated bases and the cell barcode sequence to determine the epigenetic characteristic of the nucleic acid molecule as being associated with the cell.

15. The method of claim 14, wherein the nucleic acid molecule is encapsulated in the cell bead.

16. The method of claim 14, further comprising, prior to (a), lysing the cell to release contents of the cell.

17. The method of claim 16, further comprising, subsequent to the lysing, treating the contents with one or more proteases.

18. The method of claim 14, further comprising, prior to (a), encapsulating the cell in a mixture comprising a polymer(s) or polymer precursor(s).

19. The method of claim 14, wherein (a) further comprises providing a plurality of gel beads, and wherein (b) further comprises partitioning the plurality of gel beads into the plurality of partitions, wherein the partition comprises a gel bead of the plurality of gel beads, and wherein the gel bead comprises the cell barcode sequence.

20. The method of claim 14, further comprising, subsequent to (a), performing one or more reactions within the cell bead, wherein the one or more reactions transform at least a portion of a sequence of the nucleic acid molecule.

21. The method of claim 14, wherein, subsequent to (a), an enzymatic deamination reaction is performed within the cell bead, and wherein the enzymatic deamination reaction transforms at least a portion of a sequence of the nucleic acid molecule.

* * * * *